US007785591B2

(12) United States Patent
Menrad et al.

(10) Patent No.: US 7,785,591 B2
(45) Date of Patent: Aug. 31, 2010

(54) IDENTIFICATION AND CHARACTERIZATION OF FUNCTION-BLOCKING ANTI-ED-B-FIBRONECTIN ANTIBODIES

(75) Inventors: Andreas Menrad, Oranienburg (DE); Josef Prassler, Germering (DE); Armin Weidmann, Diesser a. Ammersee (DE)

(73) Assignee: MorphoSys AG, Martinsried/Planegg (DE)

( * ) Notice: Subject to any disclaimer, the term of this patent is extended or adjusted under 35 U.S.C. 154(b) by 0 days.

(21) Appl. No.: 11/249,296

(22) Filed: Oct. 14, 2005

(65) Prior Publication Data

US 2006/0115428 A1 Jun. 1, 2006

Related U.S. Application Data

(60) Provisional application No. 60/697,565, filed on Jul. 11, 2005.

(30) Foreign Application Priority Data

Oct. 14, 2004 (DE) ....................... 10 2004 050 101

(51) Int. Cl.

| | |
|---|---|
| ***A61K 39/395*** | (2006.01) |
| ***G01N 33/53*** | (2006.01) |
| ***C07K 16/46*** | (2006.01) |
| ***C07K 16/28*** | (2006.01) |
| ***C07K 16/00*** | (2006.01) |

(52) U.S. Cl. ............................. 424/133.1; 530/388.24; 530/391.3; 530/391.5; 530/391.7; 530/387.3; 435/7.1

(58) Field of Classification Search ....................... None
See application file for complete search history.

(56) References Cited

U.S. PATENT DOCUMENTS

| | | | | |
|---|---|---|---|---|
| 5,859,205 | A * | 1/1999 | Adair et al. | 530/387.3 |
| 5,877,397 | A | 3/1999 | Lonberg et al. | |
| 6,300,129 | B1 | 10/2001 | Lonberg et al. | |
| 6,632,927 | B2 * | 10/2003 | Adair et al. | 530/387.3 |
| 7,273,924 | B1 | 9/2007 | Neri et al. | |
| 2002/0049247 | A1 | 4/2002 | Chen | |
| 2002/0197700 | A1 | 12/2002 | Menrad et al. | |
| 2003/0045681 | A1 * | 3/2003 | Neri et al. | 530/350 |
| 2003/0176663 | A1 | 9/2003 | Neri et al. | |
| 2004/0001790 | A1 | 1/2004 | Hilger et al. | |
| 2004/0013640 | A1 | 1/2004 | Zardi et al. | |
| 2005/0037402 | A1 * | 2/2005 | Schirner et al. | 435/6 |
| 2005/0074401 | A1 | 4/2005 | Borsi et al. | |
| 2005/0112690 | A1 | 5/2005 | Heldmann | |
| 2005/0221434 | A1 | 10/2005 | Menrad et al. | |
| 2006/0057146 | A1 | 3/2006 | Borsi et al. | |
| 2007/0189963 | A1 | 8/2007 | Neri et al. | |

FOREIGN PATENT DOCUMENTS

| | | | |
|---|---|---|---|
| DE | 101 23 133 | A1 | 11/2002 |
| EP | 0 344 134 | B1 | 1/1994 |
| EP | 1 262 193 | A1 | 12/2002 |
| WO | WO 97/45544 | A1 | 12/1997 |
| WO | WO 99/58570 | A | 11/1999 |
| WO | WO 01/44291 | A2 | 6/2001 |
| WO | WO 01/62298 | A2 | 8/2001 |
| WO | WO 01/62800 | A1 | 8/2001 |
| WO | WO 02/20563 | A | 3/2002 |
| WO | WO 02/46455 | A2 | 6/2002 |
| WO | WO 03/031475 | A2 | 4/2003 |
| WO | WO 03/055917 | A2 | 7/2003 |

OTHER PUBLICATIONS

Hahn et al. Antibody-Based Targeting of Angiogenesis. News Physiol. Sci. 16:191-194, 2001.*

Rudikoff et al Single amino acid substitution altering antigen-binding specificity. Proc Natl Acad Sci U S A. Mar. 1982;79(6):1979-83.*

Panka et al. Variable region framework differences result in decreased or increased affinity of variant anti-digoxin antibodies. Proc Natl Acad Sci U S A. 85(9):3080-3084, 1988.*

Padlan EA.. Anatomy of the antibody molecule. Mol Immunol. Feb. 1994;31(3):169-217.*

Portolano et al., Lack of promiscuity in autoantigen-specific H and L chain combinations as revealed by human H and L chain "roulette". J Immunol. Feb. 1, 1993;150(3):880-7.*

Menrad A et al., "molecular and functional characterization of ED-B fibronectin selective function blocking antibodies and the evaluation of phage angiomics for target identification and validation," Human Antibodies, 2004, p. 33, vol. 13 No. 1-2, & 11$^{th}$ International Conference on Human Antibodies and Hybridomas, Dublin, Ireland, Oct. 6-8, 2004.

Ebbinghaus C et al., "diagnostic and therapeutic applications of recombinant antibodies: targeting the extra-domain B of fibronectin, a marker of tumor angiogenesis," Current Pharmaceutical Design 2004, 2004, p. 1540 col. 1547, vol. 10, No. 13, Netherlands.

Menrad A et al., "ED-B fibronectin as a target for antibody-based cancer treatments," Expert Opinion on Therapeutic Targets, Jun. 2005, pp. 491-500, vol. 9 No. 3, Ashley Publications, London.

Fattorusso Roberto et al., "NMR structure of the human oncofoetal fibronectin ED-B domain, a specific marker for angiogenesis," Structure, Apr. 15, 1999, pp. 381-390, vol. 7 No. 4, London.

J. Biol. Chem., (1998), vol. 273, (34): 21769-21776, Pini et al.

http://www.clunet.edu/BioDev/omm/fibro/frames/fibrotxt.htm (2001).

Medline Abstract AN 2004214642, Weinreb et al, JBC, 2004, 279(17) :17875.

Medline Abstract AN 2002698166, Samu et al Int. j. radiat. oncol. 2002, vol. 54, No. 5, pp. 1485.

NCBI AN CAA06866 , 1998, pp. 1-3.

Austrian Patent Office Service and Information Center; Search Report for Turkish Patent Institute dated Jun. 25, 2007.

U.S. Appl. No. 10/088,866, filed Jul. 2, 2002.

* cited by examiner

*Primary Examiner*—Maher M Haddad

(57) ABSTRACT

The invention relates to recombinant polypeptides, in particular antibodies or antibody fragments that bind Ed-B-isoforms of fibronectin and can block their function. In addition, the diagnostic and pharmaceutical application of the polypeptides according to the invention is disclosed.

26 Claims, 19 Drawing Sheets

[Key to Figure 4:]

% Hemmung der HDMVEc-Adhäsion an ED-B = % Inhibition of the HDMVEc Adhesion to ED-B negative Kontrolle = Negative control

[Key to Figure 10:]

Kontrolle = Control

200µg MOR03255 in MATRIGEL; tägliche i.v. Injektionen von 100µg/Tier MOR03255 von Tag 3-9 = 200 µg of MOR03255 in MATRIGEL; Daily I.V. Injections of 100 µg/Animal of MOR03255 of Days 3-9

100µg (i.v.)MOR03255/Tier/Tag von Tag 3-9 = 100 µg (I.V.) of MOR03255/Animal/Day of Days 3-9

Tumorfläche = Tumor Surface Area

Zeit (Tage nach Tumorimplantation) = Time (Days After Tumor Implant)

Figure 11A

Parent Clone

MOR02610:
VH VH 1B
caggtgcaattggttcagagcggcgcggaagtgaaaaaaccgggcgcgagcgtgaaagtgagctgcaaagcc
tccggatataccttttactggttttatattaattgggtccgccaagcccctgggcagggtctcgagtggatg
ggctggatcaatccgtattctggcaatacgcgttacgcgcagaagtttcagggccgggtgaccatgacccgt
gataccagcattagcaccgcgtatatggaactgagcagcctgcgtagcgaagatacggccgtgtattattgc
gcgcgttctcctgtttatattaagtatgattattggggccaaggcaccctggtgacggttagctca VL VL lambda1
gatatcgtgctgacccagccgccttcagtgagtggcgcaccaggtcagcgtgtgaccatctcgtgtagcggc
agcagcggcaacattggtattaattttgtgaattggtaccagcagttgcccgggacggcgccgaaacttctg
atttataagaataataagcgtccctcaggcgtgccggatcgtttagcggatccaaaagcggcaccagcgcg
agccttgcgattacgggcctgcaaagcgaagacgaagcggattattattgccagtcttatgataagacttct
tctactatgtgtttggcggcggcacgaagttaaccgttcttggccag MOR02611:
VH VH 1B
caggtgcaattggttcagagcggcgcggaagtgaaaaaaccgggcgcgagcgtgaaagtgagctgcaaagcc
tccggatataccttttctggttcttatatgcattgggtccgccaagcccctgggcagggtctcgagtggatg
ggcattatcaatccgggtctggcaagacgcgttacgcgcagaagtttcagggccgggtgaccatgacccgt
gataccagcattagcaccgcgtatatggaactgagcagcctgcgtagcgaagatacggccgtgtattattgc
gcgcgtggtcttattatcgttttgcttcttggggccaaggcaccctggtgacggttagctca VL VL lambda2
gatatcgcactgacccagccagcttcagtgagcggctcaccaggtcagagcattaccatctcgtgtacgggt
actagcagcgatattggtggttatcattctgtgtcttggtaccagcagcatcccgggaaggcgccgaaactt
atgatttatcgttctaatcgtccctcaggcgtgagcaaccgttttagcggatccaaaagcggcaacaccgcg
agcctgaccattagcggcctgcaagcggaagacgaagcggattattattgcgctgctgctactggtggttgg
gtgtttggcggcggcacgaa t ttaaccgttcttggccag

Key:
MOR02610: VH (SEQ ID NO: 1); VL (SEQ ID NO: 3)
MOR02611: VH (SEQ ID NO: 5); VL (SEQ ID NO: 7)

Note: In VL mutation at nt 309

MOR02613:
VH VH 3
caggtgcaattggtggaaagcggcggcggcctggtgcaaccgggcggcagcctgcgtctgagctgcgcggcc
tccggatttacctttctaattatactatgacttgggtgcgccaagcccctgggaagggtctcgagtgggtg
agctttatcattggtctggtagcaatacctcttatgcggatagcgtgaaaggccgttttaccatttcacgt
gataattcgaaaaacaccctgtatctgcaaatgaacagcctgcgtgcggaagatacggccgtgtattattgc
gcgcgttatgttaatggttttgatatttggggccaaggcaccctggtgacggttagctca VL VL lambda2
gatatcgcactgacccagccagcttcagtgagcggctcaccaggtcagagcattaccatctcgtgtacgggt
actagcagcgatgttggtggttattattatgtgtcttggtaccagcagcatcccgggaaggcgccgaaactt
atgatttatgatctaagcgtccctcaggcgtgagcaaccgttttagcggatccaaaagcggcaacaccgcg
gcgagcctgaccattagcggcctgcaagcggaagacgaagcggattattattgccagacttatgctaagaag
gattatcttgtgtttggcggcggcacgaagttaaccgttcttggccag MOR02614:
VH VH 3
caggtgcaattggtggaaagcggcggcggcctggtgcaaccgggcggcagcctgcgtctgagctgcgcggcc
tccggatttacctttaataatatttggatgcattgggtgcgccaagcccctgggaagggtctcgagtgggtg
agctttatctctggttctggtagccatacctattatgcggatagcgtgaaaggccgttttaccatttcacgt
gataattcgaaaaacaccctgtatctgcaaatgaacagcctgcgtgcggaagatacggccgtgtattattgc
gcgcgtgcttatgatgtttggggccaaggcaccctggtgacggttagctca

Key:
MOR02613: VH (SEQ ID NO: 9); VL (SEQ ID NO: 11)
MOR02614: VH (SEQ ID NO: 13)

Figure 11B

VL VL lambda1
gatatcgtgctgacccagccgccttcagtgagtggcgcaccaggtcagcgtgtgaccatctcgtgtagcggc
agcagcagcaacattggtttaattatgtgaattggtaccagcagttgcccgggacggcgccgaaacttctg
atttatggtaattctaagcgtccctcaggcgtgccggatcgttttagcggatccaaaagcggcaccagcgcg
agccttgcgattacgggcctgcaaagcgaagacgaagcggattattattgcgctatgtttcctgagggt
gtgtttggcggcggcacgaagttaaccgttcttggccag MOR02616:
VH VH 3
caggtgcaattggtggaaagcggcggcggcctggtgcaaccgggcggcagcctgcgtctgagctgcgcggcc
tccggatttacctttcgtaatatgctatgcattgggtgcgccaagcccctgggaagggtctcgagtgggtg
agcgctatctcttcttctggtagcggtacctatttatgcggatagcgtgaaaggccgttttaccatttcacgt
gataattcgaaaaacaccctgtatctgcaaatgaacagcctgcgtgcggaagatacggccgtgtattattgc
gcgcgtggttattgttctttgattattggggccaaggcaccctggtgacggttagctca VL VL kappa3a
gatatcgtgctgacccagagcccggcgaccctgagcctgtctccgggcgaacgtgcgaccctgagctgcaga
gcgagccagagtgttcgttctaatctggcttggtaccagcagaaaccaggtcaagcaccgcgtctattaatt
tatggtgcttctaatcgtgcaactggggtcccggcgcgttttagcggctctggatccggcacggatttacc
ctgaccattagcagcctggaacctgaagactttgcggtttattattgccttcagaagtactctattcctttt
acctttggccagggtacgaaagttgaaattaaacgtacg MOR02618:
VH VH 3
caggtgcaattggtggaaagcggcggcggcctggtgcaaccgggcggcagcctgcgtctgagctgcgcggcc
tccggatttacctttaataattatggtatgacttgggtgcgccaagcccctgggaagggtctcgagtgggtg
agctctatctctggtatggtagcaatacctattatgcggatagcgtgaaaggccgttttaccatttcacgt
gataattcgaaaaacaccctgtatctgcaaatgaacagcctgcgtgcggaagatacggccgtgtattattgc
gcgcgtaattatgggttttgcttattggggccaaggcaccctggtgacggttagctca VL VL lambda3
gatatcgaactgacccagccgccttcagtgagcgttgcaccaggtcagaccgcgcgtatctcgtgtagcggc
gataatattcctggtaagtctgttcattggtaccagcagaaacccgggcaggcgccagttcttgtgatttat
ggtaagtctgaatcgtccctcaggcatcccggaacgctttagcggatccaacagcggcaacaccgcgaccctg
accattagcggcactcaggcggaagacgaagcggattattattgccagtctttatgataatttaatgatttct
gtgtgtttggcggcggcacgaagttaaccgttcttggccag MOR02619:
VH VH 4a_3a
caggtgcaattgcaagaaagtggtccgggcctggtgaaaccgggcgaaaccctgagcctgacctgcaccgtt
tccggaggcagcatttcttcttattattggtcttggattcgccaggcccctgggaagggtctcgagtggatt
ggcatcggtcattggggctctacccagtataatccgagcctgaaaggccgggtgaccattagcgttgatact
tcgaaaaaccagtttagcctgaaactgagcagcgtgacggcggaagatacggccgtgtattattgcgcgcgt
ttttgatgtttggggccaaggcaccctggtgacggttagctca VL VL lambda1
gatatcgtgctgacccagccgccttcagtgagtggcgcaccaggtcagcgtgtgaccatctcgtgtagcggc
agcagcagcaacattggttctaatactgtgcgttggtaccagcagttgcccgggacggcgccgaaacttctg
atttatctaataatagcgtccctcaggcgtgccggatcgttttagcggatccaaaagcggcaccagcgcg
agccttgcgattacgggcctgcaaagcgaagacgaagcggattattattgccagtcttgggatggtgctct
actggtgtgtttggcggcggcacgaagttaaccgttcttggccag

Key:
MOR02614: VL (SEQ ID NO: 15)
MOR02616: VH (SEQ ID NO: 17); VL (SEQ ID NO: 19)
MOR02618: VH (SEQ ID NO: 21); VL (SEQ ID NO: 23)
MOR02619: VH (SEQ ID NO: 25); VL (SEQ ID NO: 27)

Figure 11C

MOR02622:
VH VH 3
caggtgcaattggtggaaagcggcggcggcctggtgcaaccgggcggcagcctgcgtctgagctgcgcggcc
tccggatttaccttttctaattatgctatgacttgggtgcgccaagcccctgggaagggtctcgagtgggtg
agcggtatctcttacaagtctagctctacctattatgcggatagcgtgaaaggccgttttaccatttcacgt
gataattcgaaaaacaccctgtatctgcaaatgaacagcctgcgtgcggaagatacggccgtgtattattgc
gcgcgtggtctgttactttgataattggggccaaggcaccctggtgacggttagctca VL VL lambda2
gatatcgcactgacccagccagcttcagtgagcggctcaccaggtcagagcattaccatctcgtgtacgggt
actagcagcgatggtggttacttataattttgtgtcttggtaccagcagcatcccgggaaggcgccgaaactt
atgatttatggtttcaatcgtccctcaggcgtgagcaaccgttttagcggatccaaaagcggcaacacc
gcgagcctgaccattagcggcctgcaagcggaagacgaagcggattattattgcgtcttcttggactcattct
ttactgattatgtgtttggcggcggcacgaagttaaccgttcttggccag MOR02715:
VH VH 3
caggtgcaattggtggaaagcggcggcggcctggtgcaaccgggcggcagcctgcgtctgagctgcgcggcc
tccggatttacctttctcttatggtatgcattgggtgcgccaagcccctgggaagggtctcgagtgggtg
agcgttatctcttctcggtagctatatctattatgcggatagcgtgaaaggccgttttaccatttcacgt
gataattcgaaaaacaccctgtatctgcaaatgaacagcctgcgtgcggaagatacggccgtgtattattgc
gcgcgtaataaggttggttttgatgtttggggccaaggcaccctggtgacggttagctca VL VL lambda2
gatatcgcactgacccagccagcttcagtgagcggctcaccaggtcagagcattaccatctcgtgtacgggt
actagcagcgatggtggtggttataatactgtgtcttggtaccagcagcatcccgggaaggcgccgaaactt
atgatttatgttcataagcgtccctcaggcgtgagcaaccgttttagcggatccaaaagcggcaacacc
gcgagcctgaccattagcggcctgcaagcggaagacgaagcggattattattgccaggcttgggataatcag
ggtatgaagtatgtgtttggcggcggcacgaagttaaccgttcttggccag MOR02718:
VH VH 3
caggtgcaattggtggaaagcggcggcggcctggtgcaaccgggcggcagcctgcgtctgagctgcgcggcc
tccggatttacctttaatcttaatgctatgcattgggtgcgccaagcccctgggaagggtctcgagtgggtg
agctttatctctggttctggtagctctacctattatgcggatagcgtgaaaggccgttttaccatttcacgt
gataattcgaaaaacaccctgtatctgcaaatgaacagcctgcgtgcggaagatacggccgtgtattattgc
gcgcgtggttggtttttgctcattggggccaaggcaccctggtgacggttagctca VL VL kappa3_3a
gatatcgtgctgacccagagcccggcgaccctgagcctgtctccgggcgaacgtgcgaccctgagctgcaga
gcgagccagtctgtttcgtggtaatctggcttggtaccagcagaaaccaggtcaagcaccgcgtctattaatt
tatgatgcttctaatcgtgcaactggggtcccggcgcgttttagcggctctggatccggcacggattttacc
ctgaccattagcagcctggaacctgaagactttgcggtttattattgccttcagtattctctgttcctcttt
acctttggccagggtacgaaagttgaaattaaacgtacg MOR02721:
VH VH 5
caggtgcaattggttcagagcggcgcggaagtgaaaaaaccgggcgaaagcctgaaaattagctgcaaaggt
tccggatattcctttacttcttattatattagttgggtgcgccagatgcctgggaagggtctcgagtggatg
ggcattatctatccgtctactagccgtaccatttattctccgagctttcagggccaggtgaccattagcgcg
gataaaagcattagcaccgcgtatcttcaatggagcagcctgaaagcgagcgatacggccatgtattattgc
gcgcgttatcatggtgcttttggggccaaggcaccctggtgacggttagctca

Key:
MOR02622: VH (SEQ ID NO: 29); VL (SEQ ID NO: 31)
MOR02715: VH (SEQ ID NO: 33); VL (SEQ ID NO: 35)
MOR02718: VH (SEQ ID NO: 37); VL (SEQ ID NO: 39)
MOR02721: VH (SEQ ID NO: 41)

Figure 11D

VL VL lambda1
gatatcgtgctgacccagccgccttcagtgagtggcgcaccaggtcagcgtgtgaccatctcgtgtagcggc
agcagcagcaacattggttctcattatgtgtattggtaccagcagttgcccgggacggcgccgaaacttctg
atttatcgtaattctgagcgtccctcaggcgtgccggatcgttttagcggatccaaaagcggcaccagcgcg
agccttgcgattacgggcctgcaaagcgaagacgaagcggattattattgccaggcttatactactggtct
attgtgtttggcggcggcacgaagttaaccgttcttggccag MOR02722:
VH VH 3
caggtgcaattggtggaaagcggcggcggcctggtgcaaccgggcggcagcctgcgtctgagctgcgcggcc
tccggatttacctttcttcttaatgctattcattgggtgcgccaagcccctgggaagggtctcgagtgggtg
agctctatctctggttctggtagcaatacctattatgcggatagcgtgaaaggccgttttaccatttcacgt
gataattcgaaaaacaccctgtatctgcaaatgaacagcctgcgtgcggaagatacggccgtgtattattgc
gcgcgttttatgcttctggggccaaggcaccctggtgacggttagctca VL VL kappa2
gatatcgtgatgacccagagcccactgagcctgccagtgactccgggcgagcctgcgagcattagctgcaga
agcagccaaagcctgcttcattctaatggctataactatctgaattggtaccttcaaaaaccaggtcaaagc
ccgcagctattaatttatcttggttctaatcgtgccagtggggtcccggatcgttttagcggctctggatcc
ggcaccgattttaccctgaaaattagccgtgtggaagctgaagacgtgggcgtgtattattgccagcagtat
tctaatttccttttaccttggccagggtacgaaagttgaaattaaacgtacg

Key:
MOR02721: VL (SEQ ID NO: 43)
MOR02722: VH (SEQ ID NO: 45); VL (SEQ ID NO: 47)

First Maturation: LCDR3 Maturation

Derivatives of MOR02619:

VH: All Fabs:

VH4_3a
caggtgcaattgcaagaaagtggtccgggcctggtgaaaccgggcgaaaccctgagcctgacctgcaccgtt
tccggaggcagcatttcttcttattattggtcttggattcgccaggccccctgggaagggtctcgagtggatt
ggcatcggtcattgggggctctacccagtataatccgagcctgaaaagccgggtgaccattagcgttgatact
tcgaaaaaccagtttagcctgaaactgagcagcgtgacggcggaagatacggccgtgtattattgcgcgcgt
tttttgatgttttggggccaaggcaccctggtgacggttagctca VL:
MOR03055:
VL Vlambda1_3
gatatcgtgctgacccagccgccttcagtgagtggcgcaccaggtcagcgtgtgaccatctcgtgtagcggc
agcagcagcaacattggttctaatactgtgcgttggtaccagcagttgcccgggacggcgccgaaacttctg
atttatctaataataagcgtccctcaggcgtgccggatcgttttagcggatccaaaagcggcaccagcgcg
agccttgcgattacgggcctgcaaagcgaagacgaagcggattattattgccaggcttggactcgtgctcat
cgtatcctgtgtttggcggcggcacgaagttaaccgttcttggccag MOR03066:
VL Vlambda1_3
gatatcgtgctgacccagccgccttcagtgagtggcgcaccaggtcagcgtgtgaccatctcgtgtagcggc
agcagcagcaacattggttctaatactgtgcgttggtaccagcagttgcccgggacggcgccgaaacttctg
atttatctaataataagcgtccctcaggcgtgccggatcgttttagcggatccaaaagcggcaccagcgcg
agccttgcgattacgggcctgcaaagcgaagacgaagcggattattattgctcttctatgatactcaggtt
actcgtgtgtttggcggcggcacgaagttaaccgttcttggccag

Key:
MOR02619: VH (SEQ ID NO: 25)
MOR03055: VL (SEQ ID NO: 49)
MOR03066: VL (SEQ ID NO: 51)

Figure 11E

MOR03075:
VL Vlambda1_3
gatatcgtgctgacccagccgccttcagtgagtggcgcaccaggtcagcgtgtgaccatctcgtgtagcggc
agcagcagcaacattggttctaatactgtgcgttggtaccagcagttgcccgggacggcgccgaaacttctg
atttattctaataataagcgtccctcaggcgtgccggatcgttttagcggatccaaaagcggcaccagcgcg
agccttgcgattacgggcctgcaaagcgaagacgaagcggattattattgccagtcttgggatcctcgtctt
tttactgtgtttggcggcggcacgaagttaaccgttcttggccag MOR03069:
VL Vlambda1_3
gatatcgtgctgacccagccgccttcagtgagtggcgcaccaggtcagcgtgtgaccatctcgtgtagcggc
agcagcagcaacattggttctaatactgtgcgttggtaccagcagttgcccgggacggcgccgaaacttctg
atttattctaataataagcgtccctcaggcgtgccggatcgttttagcggatccaaaagcggcaccagcgcg
agccttgcgattacgggcctgcaaagcgaagacgaagcggattattattgctggactggtatgtcttatcat
tttgtgtttggcggcggcacgaagttaaccgttcttggccag MOR03071:
VL Vlambda1_3
gatatcgtgctgacccagccgccttcagtgagtggcgcaccaggtcagcgtgtgaccatctcgtgtagcggc
agcagcagcaacattggttctaatactgtgcgttggtaccagcagttgcccgggacggcgccgaaacttctg
atttattctaataataagcgtccctcaggcgtgccggatcgttttagcggatccaaaagcggcaccagcgcg
agccttgcgattacgggcctgcaaagcgaagacgaagcggattattattgccttgctctatattcagctaag
ggtcatgtgtttggcggcggcacgaagttaaccgttcttggccag

Key:
MOR03075: VL (SEQ ID NO: 53)
MOR03069: VL (SEQ ID NO: 55)
MOR03071: VL (SEQ ID NO: 57)

Derivatives of MOR02715:

VH: All Fabs:

VH3_3a
caggtgcaattggtggaaagcggcggcggcctggtgcaaccgggcggcagcctgcgtctgagctgcgcggcc
tccggatttacctttcttcttatggtatgcattgggtgcgccaagcccctgggaagggtctcgagtgggtg
agcgttatctcttctctggtagctatatctattatgcggatagcgtgaaaggccgttttaccatttcacgt
gataattcgaaaaacaccctgtatctgcaaatgaacagcctgcgtgcggaagatacggccgtgtattattgc
gcgcgtaatagaggttggtttgatgtttggggccaaggcaccctggtgacggttagctca VL:
MOR03064:
Vlambda2_3
gatatcgcactgacccagccagcttcagtgagcggctcaccaggtcagagcattaccatctcgtgtacgggt
actagcagcgatgtgggtggttataattacgtgtcttggtaccagcagcatcccgggaaggcgccgaaactt
atgatttattatgttcataagcgtccctcaggcgtgagcaaccgttttagcggatccaaaagcggcaacacc
gcgagcctgaccattagcggcctgcaagcggaagacgaagcggattattattgccagtcttgggatcttctt
gctccttctgttgtgtttggcggcggcacgaagttaaccgttcttggccag MOR03062:
Vlambda2_3
gatatcgcactgacccagccagcttcagtgagcggctcaccaggtcagagcattaccatctcgtgtacgggt
actagcagcgatgtgggtggttataattacgtgtcttggtaccagcagcatcccgggaaggcgccgaaactt
atgatttatgatgttcataagcgtccctcaggcgtgagcaaccgttttagcggatccaaaagcggcaacacc
gcgagcctgaccattagcggcctgcaagcggaagacgaagcggattattattgccagtcttgggatctttct
gttcatcaggttgtgtttggcggcggcacgaagttaaccgttcttggccag

Key:
MOR02715: VH (SEQ ID NO: 33)
MOR03064: VL (SEQ ID NO: 59)
MOR03062: VL (SEQ ID NO: 61)

Figure 11F

2. Maturation: HCDR2

Derivatives of MOR03055:

MOR03243 VH VH4_3a
caggtgcaattgcaagaaagtggtccgggcctggtgaaaccgggcgaaaccctgagcctgacctgcaccgt
ttccggaggcagcatttctctattattggtcttggattcgccaggcccctgggaagggtctcgagtggatt
ggcgagattcatcgtggtggttatactcagtataatccttctcttaagtctcgggtcaccattagcgtggat
acttcgaaaaaccagtttagcctgaaactgagcagcgtgacggcggcggatacggccgtgtattattgcgcg
cgtttttgatgtttggggccaaggcaccctggtgacggttagctca VL Vlambda1_3
gatatcgtgctgacccagccgccttcagtgagtggcgcaccaggtcagcgtgtgaccatctcgtgtagcggc
agcagcagcaacattggttctaatactgtgcgttggtaccagcagttgcccgggacggcgccgaaacttctg
atttatctaataataagcgtccctcaggcgtgccggatcgttttagcggatccaaaagcggcaccagcgcg
agccttgcgattacgggcctgcaaagcgaagacgaagcggattattattgccaggcttggactcgtgctcat
cgttatcctgtgtttggcggcggcacgaagttaaccgttcttggccag

Key:
MOR03243: VH (SEQ ID NO: 63); VL (SEQ ID NO: 65)

Derivatives of MOR03069:

MOR03245 VH VH4_3a
caggtgcaattgcaagaaagtggtccgggcctggtgaaaccgggcgaaaccctgagcctgacctgcaccgt
ttccggaggcagcatttctctattatttggtcttggattcgccaggcccctgggaagggtctcgagtggatt
ggcgttattcataagtgggggttttactaattctaatccttctcttaagtctcgggtcaccattagcgtggat
acttcgaaaaaccagtttagcctgaaactgagcagcgtgacggcggcggatacggccgtgtattattgcgcg
cgtttttgatgtttggggccaaggcaccctggtgacggttagctca VL Vlambda1_3
gatatcgtgctgacccagccgccttcagtgagtggcgcaccaggtcagcgtgtgaccatctcgtgtagcggc
agcagcagcaacattggttctaatactgtgcgttggtaccagcagttgcccgggacggcgccgaaacttctg
atttatctaataataagcgtccctcaggcgtgccggatcgttttagcggatccaaaagcggcaccagcgcg
agccttgcgattacgggcctgcaaagcgaagacgaagcggattattattgctggactggtatgtcttatcat
ttgtgtttggcggcggcacgaagttaaccgttcttggccag

Key:
MOR03245: VH (SEQ ID NO: 67); VL (SEQ ID NO: 69)

Derivatives of MOR03075:

MOR03246 VH VH4_3a
caggtgcaattgcaagaaagtggtccgggcctggtgaaaccgggcgaaaccctgagcctgacctgcaccgt
ttccggaggcagcatttcttctattattggtcttggattcgccaggcccctgggaagggtctcgagtggatt
ggctatattcataagtatggtggaactaagtataatccttctcttaagtctcgggtcaccattagcgttgat
acttcgaaaaaccagtttagcctgaaactgagcagcgtgacggcggcggatacggccgtgtattattgcgcg
cgttttttgatgtttggggc
caaggcaccctggtgacggttagctca VL Vlambda1_3
gatatcgtgctgacccagccgccttcagtgagtggcgcaccaggtcagcgtgtgaccatctcgtgtagcggc
agcagcagcaacattggttctaatactgtgcgttggtaccagcagttgcccgggacggcgccgaaacttctg
atttatctaataataagcgtccctcaggcgtgccggatcgttttagcggatccaaaagcggcaccagcgcg
agccttgcgattacgggcctgcaaagcgaagacgaagcggattattattgccagtcttgggatcctcgttct
ttactgtgtttggcggcggcacgaagttaaccgttcttggccag

Key:
MOR03246: VH (SEQ ID NO: 71); VL (SEQ ID NO: 73)

Note: VH4_3a sequences were back-mutated in FR2 of HuCAL GOLD to Fab2 with use of a Fab2 maturation cassette

Figure 11G

Derivatives of MOR03062:

MOR03251 VH VH3_3 caggtgcaattggtggaaagcggcggcggcctggtgcaaccgggcggcagcctgcgtctgagctgcgcggcc
tccggatttacctttcttcttatggtatgcattgggtgcgccaagcccctgggaagggtctcgagtgggtg
agcgttatttctaatatgtcttatactattattatgctgattctgttaagggtcgttttaccatttcacgt
gataattcgaaaaacaccctgtatctgcaaatgaacagcctgcgtgcggaagatacggccgtgtattattgc
gcgcgtaataaggttggtttgatgtttggggccaaggcaccctggtgacggttagctca VL Vlambda2_3 gatatcgcactgacccagccagcttcagtgagcggctcaccaggtcagagcattaccatctcgtgtacgggt
actagcagcgatggtggtggttataactatgtgtcttggtaccagcagcatcccgggaaggcgccgaaactt
atgatttatgttcataagcgtccctcaggcgtgagcaaccgttttagcggatccaaaagcggcaacacc
gcgagcctgaccattagcggcctgcaagcggaagacgaagcggattattattgccagtcttgggatctttct
gttcatcaggtgtgtttggcggcggcacgaagttaaccgttcttggccag

MOR03252 VH VH3_3 caggtgcaattggtggaaagcggcggcggcctggtgcaaccgggcggcagcctgcgtctgagctgcgcggcc
tccggatttacctttcttcttatggtatgcattgggtgcgccaagcccctgggaagggtctcgagtgggtg
agcgttatttctaatatctctggcaatattattatgctgattctgttaagggtcgttttaccatttcacgt
gataattcgaaaaacaccctgtatctgcaaatgaacagcctgcgtgcggaagatacggccgtgtattattgc
gcgcgtaataaggttggtttgatgtttggggccaaggcaccctggtgacggttagctca

Key:
MOR03251: VH (SEQ ID NO: 75); VL (SEQ ID NO: 77)
MOR03252: VH (SEQ ID NO: 79)

VL Vlambda2_3 such as 3251

MOR03253 VH VH3_3 caggtgcaattggtggaaagcggcggcggcctggtgcaaccgggcggcagcctgcgtctgagctgcgcggcc
tccggatttacctttcttcttatggtatgcattgggtgcgccaagcccctgggaagggtctcgagtgggtg
agcgttatttctaatatgggttttgagattattatgctgattctgttaagggtcgttttaccatttcacgt
gataattcgaaaaacaccctgtatctgcaaatgaacagcctgcgtgcggaagatacggccgtgtattattgc
gcgcgtaataaggttggtttgatgtttggggccaaggcaccctggtgacggttagctca

Key:
MOR03253: VH (SEQ ID NO: 81)

VL Vlambda2_3 such as 3251

MOR03255 VH VH3_3 caggtgcaattggtggaaagcggcggcggcctggtgcaaccgggcggcagcctgcgtctgagctgcgcggcc
tccggatttacctttcttcttatggtatgcattgggtgcgccaagcccctgggaagggtctcgagtgggtg
agcgttatttctaatcgttctcttatattattatgctgattctgttaagggtcgttttaccatttcacgt
gataattcgaaaaacaccctgtatctgcaaatgaacagcctgcgtgcggaagatacggccgtgtattattgc
gcgcgtaataaggttggtttgatgtttggggccaaggcaccctggtgacggttagctca

Key:
MOR03255: VH (SEQ ID NO: 83)

VL Vlambda2_3 such as 3251

MOR03257 VH VH3_3 caggtgcaattggtggaaagcggcggcggcctggtgcaaccgggcggcagcctgcgtctgagctgcgcggcc
tccggatttacctttcttcttatggtatgcattgggtgcgccaagcccctgggaagggtctcgagtgggtg
agcgttatttctaatcgtggtaattatattattatgctgattctgttaagggtcgttttaccatttcacgt
gataattcgaaaaacaccctgtatctgcaaatgaacagcctgcgtgcggaagatacggccgtgtattattgc
gcgcgtaataaggttggtttgatgtttggggccaaggcaccctggtgacggttagctca

Key:
MOR03257: VH (SEQ ID NO: 85)

VL Vlambda2_3 such as 3251

Figure 11H

Derivatives of MOR03075:

MOR03258 VH VH3_3
caggtgcaattggtggaaagcggcggcggcctggtgcaaccgggcggcagcctgcgtctgagctgcgcggcc
tccggatttacctttctcttatggtatgcattgggtgcgccaagcccctgggaagggtctcgagtgggtg
agcgttatttctaatcagtctaatattattatgctgattctgttaagggtcgttttaccatttcacgt
gataattcgaaaaacaccctgtatctgcaaatgaacagcctgcgtgcggaagatacggccgtgtattattgc
gcgcgtaatatgggtggttttgatgtttggggccaaggcaccctggtgacggttagctca VL Vlambda2_3
gatatcgcactgacccagccagcttcagtgagcggctcaccaggtcagagcattaccatctcgtgtacgggt
actagcagcgatgtgggtggttataatactgtgtcttggtaccagcagcatcccgggaaggcgccgaaactt
atgatttatgatgtcaataagcgtccctcaggcgtgagcaaccgttttagcggatccaaaagcggcaacacc
gcgagcctgaccattagcggcctgcaagcggaagacgaagcggattattattgccagtcttgggatcttctt
gctccttctgttgtgtttggcggcggcacgaagttaaccgttcttggccag

Key:
MOR03258: VH (SEQ ID NO: 87); VL (SEQ ID NO: 59)

SEQUENCE LISTING

```
<160> NUMBER OF SEQ ID NOS: 90

<210> SEQ ID NO 1
<211> LENGTH: 354
<212> TYPE: DNA
<213> ORGANISM: human
<220> FEATURE:
<221> NAME/KEY: CDS
<222> LOCATION: (1)..(354)
<223> OTHER INFORMATION: Antibody-VH-Region; MOR02610

<400> SEQUENCE: 1

cag gtg caa ttg gtt cag agc ggc gcg gaa gtg aaa aaa ccg ggc gcg       48
Gln Val Gln Leu Val Gln Ser Gly Ala Glu Val Lys Lys Pro Gly Ala
  1               5                  10                  15

agc gtg aaa gtg agc tgc aaa gcc tcc gga tat acc ttt act ggt ttt       96
Ser Val Lys Val Ser Cys Lys Ala Ser Gly Tyr Thr Phe Thr Gly Phe
             20                  25                  30

tat att aat tgg gtc cgc caa gcc cct ggg cag ggt ctc gag tgg atg      144
Tyr Ile Asn Trp Val Arg Gln Ala Pro Gly Gln Gly Leu Glu Trp Met
         35                  40                  45

ggc tgg atc aat ccg tat tct ggc aat acg cgt tac gcg cag aag ttt      192
Gly Trp Ile Asn Pro Tyr Ser Gly Asn Thr Arg Tyr Ala Gln Lys Phe
     50                  55                  60

cag ggc cgg gtg acc atg acc cgt gat acc agc att agc acc gcg tat      240
Gln Gly Arg Val Thr Met Thr Arg Asp Thr Ser Ile Ser Thr Ala Tyr
 65                  70                  75                  80

atg gaa ctg agc agc ctg cgt agc gaa gat acg gcc gtg tat tat tgc      288
Met Glu Leu Ser Ser Leu Arg Ser Glu Asp Thr Ala Val Tyr Tyr Cys
                 85                  90                  95

gcg cgt tct cct gtt tat tat aag tat gat tat tgg ggc caa ggc acc      336
Ala Arg Ser Pro Val Tyr Tyr Lys Tyr Asp Tyr Trp Gly Gln Gly Thr
            100                 105                 110

ctg gtg acg gtt agc tca                                              354
Leu Val Thr Val Ser Ser
        115


<210> SEQ ID NO 2
<211> LENGTH: 118
<212> TYPE: PRT
<213> ORGANISM: human

<400> SEQUENCE: 2

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Phe
             20                  25                  30

Tyr Ile Asn Trp Val Arg Gln Ala Pro Gly Gln Gly Leu Glu Trp Met
         35                  40                  45

Gly Trp Ile Asn Pro Tyr Ser Gly Asn Thr Arg Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
```

-continued

```
                85                  90                  95

Ala Arg Ser Pro Val Tyr Tyr Lys Tyr Asp Tyr Trp Gly Gln Gly Thr
            100                 105                 110

Leu Val Thr Val Ser Ser
        115


<210> SEQ ID NO 3
<211> LENGTH: 336
<212> TYPE: DNA
<213> ORGANISM: human
<220> FEATURE:
<221> NAME/KEY: CDS
<222> LOCATION: (1)..(336)
<223> OTHER INFORMATION: Antibody-VL Region; MOR02610

<400> SEQUENCE: 3

gat atc gtg ctg acc cag ccg cct tca gtg agt ggc gca cca ggt cag       48
Asp Ile Val Leu Thr Gln Pro Pro Ser Val Ser Gly Ala Pro Gly Gln
  1               5                  10                  15

cgt gtg acc atc tcg tgt agc ggc agc agc ggc aac att ggt att aat       96
Arg Val Thr Ile Ser Cys Ser Gly Ser Ser Gly Asn Ile Gly Ile Asn
             20                  25                  30

ttt gtg aat tgg tac cag cag ttg ccc ggg acg gcg ccg aaa ctt ctg      144
Phe Val Asn Trp Tyr Gln Gln Leu Pro Gly Thr Ala Pro Lys Leu Leu
         35                  40                  45

att tat aag aat aat aag cgt ccc tca ggc gtg ccg gat cgt ttt agc      192
Ile Tyr Lys Asn Asn Lys Arg Pro Ser Gly Val Pro Asp Arg Phe Ser
     50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                  70                  75                  80

agc gaa gac gaa gcg gat tat tat tgc cag tct tat gat aag act tct      288
Ser Glu Asp Glu Ala Asp Tyr Tyr Cys Gln Ser Tyr Asp Lys Thr Ser
                85                  90                  95

tct act tat gtg ttt ggc ggc ggc acg aag tta acc gtt ctt ggc cag      336
Ser Thr Tyr Val Phe Gly Gly Gly Thr Lys Leu Thr Val Leu Gly Gln
            100                 105                 110


<210> SEQ ID NO 4
<211> LENGTH: 112
<212> TYPE: PRT
<213> ORGANISM: human

<400> SEQUENCE: 4

Asp Ile Val Leu Thr Gln Pro Pro Ser Val Ser Gly Ala Pro Gly Gln
  1               5                  10                  15

Arg Val Thr Ile Ser Cys Ser Gly Ser Ser Gly Asn Ile Gly Ile Asn
             20                  25                  30

Phe Val Asn Trp Tyr Gln Gln Leu Pro Gly Thr Ala Pro Lys Leu Leu
         35                  40                  45

Ile Tyr Lys Asn Asn Lys Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Ser Tyr Asp Lys Thr Ser
                85                  90                  95

Ser Thr Tyr Val Phe Gly Gly Gly Thr Lys Leu Thr Val Leu Gly Gln
            100                 105                 110


<210> SEQ ID NO 5
```

-continued

```
<211> LENGTH: 351
<212> TYPE: DNA
<213> ORGANISM: human
<220> FEATURE:
<221> NAME/KEY: CDS
<222> LOCATION: (1)..(351)
<223> OTHER INFORMATION: Antibody-VH Region; MOR02611

<400> SEQUENCE: 5

cag gtg caa ttg gtt cag agc ggc gcg gaa gtg aaa aaa ccg ggc gcg       48
Gln Val Gln Leu Val Gln Ser Gly Ala Glu Val Lys Lys Pro Gly Ala
  1               5                  10                  15

agc gtg aaa gtg agc tgc aaa gcc tcc gga tat acc ttt tct ggt tct       96
Ser Val Lys Val Ser Cys Lys Ala Ser Gly Tyr Thr Phe Ser Gly Ser
             20                  25                  30

tat atg cat tgg gtc cgc caa gcc cct ggg cag ggt ctc gag tgg atg      144
Tyr Met His Trp Val Arg Gln Ala Pro Gly Gln Gly Leu Glu Trp Met
         35                  40                  45

ggc att atc aat ccg gct tct ggc aag acg ctt tac gcg cag aag ttt      192
Gly Ile Ile Asn Pro Ala Ser Gly Lys Thr Leu Tyr Ala Gln Lys Phe
     50                  55                  60

cag ggc cgg gtg acc atg acc cgt gat acc agc att agc acc gcg tat      240
Gln Gly Arg Val Thr Met Thr Arg Asp Thr Ser Ile Ser Thr Ala Tyr
 65                  70                  75                  80

atg gaa ctg agc agc ctg cgt agc gaa gat acg gcc gtg tat tat tgc      288
Met Glu Leu Ser Ser Leu Arg Ser Glu Asp Thr Ala Val Tyr Tyr Cys
                 85                  90                  95

gcg cgt ggt ctt tat tat cgt ttt gct tct tgg ggc caa ggc acc ctg      336
Ala Arg Gly Leu Tyr Tyr Arg Phe Ala Ser Trp Gly Gln Gly Thr Leu
            100                 105                 110

gtg acg gtt agc tca                                                  351
Val Thr Val Ser Ser
        115


<210> SEQ ID NO 6
<211> LENGTH: 117
<212> TYPE: PRT
<213> ORGANISM: human

<400> SEQUENCE: 6

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Ser Gly Ser
             20                  25                  30

Tyr Met His Trp Val Arg Gln Ala Pro Gly Gln Gly Leu Glu Trp Met
         35                  40                  45

Gly Ile Ile Asn Pro Ala Ser Gly Lys Thr Leu Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Gly Leu Tyr Tyr Arg Phe Ala Ser Trp Gly Gln Gly Thr Leu
            100                 105                 110

Val Thr Val Ser Ser
        115


<210> SEQ ID NO 7
<211> LENGTH: 327
<212> TYPE: DNA
<213> ORGANISM: human
```

-continued

<220> FEATURE:
<221> NAME/KEY: CDS
<222> LOCATION: (1)..(327)
<223> OTHER INFORMATION: Antibody-VL Region; MOR02611

<400> SEQUENCE: 7

```
gat atc gca ctg acc cag cca gct tca gtg agc ggc tca cca ggt cag       48
Asp Ile Ala Leu Thr Gln Pro Ala Ser Val Ser Gly Ser Pro Gly Gln
  1               5                  10                  15

agc att acc atc tcg tgt acg ggt act agc agc gat att ggt ggt tat       96
Ser Ile Thr Ile Ser Cys Thr Gly Thr Ser Ser Asp Ile Gly Gly Tyr
             20                  25                  30

cat tct gtg tct tgg tac cag cag cat ccc ggg aag gcg ccg aaa ctt      144
His Ser Val Ser Trp Tyr Gln Gln His Pro Gly Lys Ala Pro Lys Leu
         35                  40                  45

atg att tat cgt tct aat cgt ccc tca ggc gtg agc aac cgt ttt agc      192
Met Ile Tyr Arg Ser Asn Arg Pro Ser Gly Val Ser Asn Arg Phe Ser
     50                  55                  60

gga tcc aaa agc ggc aac acc gcg agc ctg acc att agc ggc ctg caa      240
Gly Ser Lys Ser Gly Asn Thr Ala Ser Leu Thr Ile Ser Gly Leu Gln
 65                  70                  75                  80

gcg gaa gac gaa gcg gat tat tat tgc gct gct gct act ggt ggt tgg      288
Ala Glu Asp Glu Ala Asp Tyr Tyr Cys Ala Ala Ala Thr Gly Gly Trp
                 85                  90                  95

gtg ttt ggc ggc ggc acg aat tta acc gtt ctt ggc cag                  327
Val Phe Gly Gly Gly Thr Asn Leu Thr Val Leu Gly Gln
            100                 105
```

<210> SEQ ID NO 8
<211> LENGTH: 109
<212> TYPE: PRT
<213> ORGANISM: human

<400> SEQUENCE: 8

```
Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Ile Gly Gly Tyr
             20                  25                  30

His Ser Val Ser Trp Tyr Gln Gln His Pro Gly Lys Ala Pro Lys Leu
         35                  40                  45

Met Ile Tyr Arg Ser Asn Arg Pro Ser Gly Val Ser Asn Arg Phe Ser
     50                  55                  60

Gly Ser Lys Ser Gly Asn Thr Ala Ser Leu Thr Ile Ser Gly Leu Gln
 65                  70                  75                  80

Ala Glu Asp Glu Ala Asp Tyr Tyr Cys Ala Ala Ala Thr Gly Gly Trp
                 85                  90                  95

Val Phe Gly Gly Gly Thr Asn Leu Thr Val Leu Gly Gln
            100                 105
```

<210> SEQ ID NO 9
<211> LENGTH: 348
<212> TYPE: DNA
<213> ORGANISM: human
<220> FEATURE:
<221> NAME/KEY: CDS
<222> LOCATION: (1)..(348)
<223> OTHER INFORMATION: Antibody-VH Region; MOR02613

<400> SEQUENCE: 9

```
cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15
```

-continued

```
agc ctg cgt ctg agc tgc gcg gcc tcc gga ttt acc ttt tct aat tat       96
Ser Leu Arg Leu Ser Cys Ala Ala Ser Gly Phe Thr Phe Ser Asn Tyr
            20                  25                  30

act atg act tgg gtg cgc caa gcc cct ggg aag ggt ctc gag tgg gtg      144
Thr Met Thr Trp Val Arg Gln Ala Pro Gly Lys Gly Leu Glu Trp Val
        35                  40                  45

agc ttt atc att ggt tct ggt agc aat acc tct tat gcg gat agc gtg      192
Ser Phe Ile Ile Gly Ser Gly Ser Asn Thr Ser Tyr Ala Asp Ser Val
    50                  55                  60

aaa ggc cgt ttt acc att tca cgt gat aat tcg aaa aac acc ctg tat      240
Lys Gly Arg Phe Thr Ile Ser Arg Asp Asn Ser Lys Asn Thr Leu Tyr
65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                85                  90                  95

gcg cgt tat gtt aat ggt ttt gat att tgg ggc caa ggc acc ctg gtg      336
Ala Arg Tyr Val Asn Gly Phe Asp Ile Trp Gly Gln Gly Thr Leu Val
            100                 105                 110

acg gtt agc tca                                                      348
Thr Val Ser Ser
        115


<210> SEQ ID NO 10
<211> LENGTH: 116
<212> TYPE: PRT
<213> ORGANISM: human

<400> SEQUENCE: 10

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asn Tyr
            20                  25                  30

Thr Met Thr Trp Val Arg Gln Ala Pro Gly Lys Gly Leu Glu Trp Val
        35                  40                  45

Ser Phe Ile Ile Gly Ser Gly Ser Asn Thr Ser Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Tyr Val Asn Gly Phe Asp Ile Trp Gly Gln Gly Thr Leu Val
            100                 105                 110

Thr Val Ser Ser
        115


<210> SEQ ID NO 11
<211> LENGTH: 339
<212> TYPE: DNA
<213> ORGANISM: human
<220> FEATURE:
<221> NAME/KEY: CDS
<222> LOCATION: (1)..(339)
<223> OTHER INFORMATION: Antibody-VL Region; MOR02613

<400> SEQUENCE: 11

gat atc gca ctg acc cag cca gct tca gtg agc ggc tca cca ggt cag       48
Asp Ile Ala Leu Thr Gln Pro Ala Ser Val Ser Gly Ser Pro Gly Gln
1               5                   10                  15

agc att acc atc tcg tgt acg ggt act agc agc gat gtt ggt gtt tat       96
Ser Ile Thr Ile Ser Cys Thr Gly Thr Ser Ser Asp Val Gly Val Tyr
```

-continued

```
             20                  25                  30

tat tat gtg tct tgg tac cag cag cat ccc ggg aag gcg ccg aaa ctt      144
Tyr Tyr Val Ser Trp Tyr Gln Gln His Pro Gly Lys Ala Pro Lys Leu
         35                  40                  45

atg att tat tat gat tct aag cgt ccc tca ggc gtg agc aac cgt ttt      192
Met Ile Tyr Tyr Asp Ser Lys Arg Pro Ser Gly Val Ser Asn Arg Phe
     50                  55                  60

agc gga tcc aaa agc ggc aac acc gcg agc ctg acc att agc ggc ctg      240
Ser Gly Ser Lys Ser Gly Asn Thr Ala Ser Leu Thr Ile Ser Gly Leu
 65                  70                  75                  80

caa gcg gaa gac gaa gcg gat tat tat tgc cag act tat gct aag aag      288
Gln Ala Glu Asp Glu Ala Asp Tyr Tyr Cys Gln Thr Tyr Ala Lys Lys
                 85                  90                  95

gat tat tct ctt gtg ttt ggc ggc ggc acg aag tta acc gtt ctt ggc      336
Asp Tyr Ser Leu Val Phe Gly Gly Gly Thr Lys Leu Thr Val Leu Gly
            100                 105                 110

cag                                                                  339
Gln


<210> SEQ ID NO 12
<211> LENGTH: 113
<212> TYPE: PRT
<213> ORGANISM: human

<400> SEQUENCE: 12

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Val Gly Val Tyr
             20                  25                  30

Tyr Tyr Val Ser Trp Tyr Gln Gln His Pro Gly Lys Ala Pro Lys Leu
         35                  40                  45

Met Ile Tyr Tyr Asp Ser Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Thr Tyr Ala Lys Lys
                 85                  90                  95

Asp Tyr Ser Leu Val Phe Gly Gly Gly Thr Lys Leu Thr Val Leu Gly
            100                 105                 110

Gln


<210> SEQ ID NO 13
<211> LENGTH: 339
<212> TYPE: DNA
<213> ORGANISM: human
<220> FEATURE:
<221> NAME/KEY: CDS
<222> LOCATION: (1)..(339)
<223> OTHER INFORMATION: Antibody-VH Region; MOR02614

<400> SEQUENCE: 13

cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt aat aat aat       96
Ser Leu Arg Leu Ser Cys Ala Ala Ser Gly Phe Thr Phe Asn Asn Asn
             20                  25                  30

tgg atg cat tgg gtg cgc caa gcc cct ggg aag ggt ctc gag tgg gtg      144
Trp Met His Trp Val Arg Gln Ala Pro Gly Lys Gly Leu Glu Trp Val
         35                  40                  45
```

-continued

```
agc ttt atc tct ggt tct ggt agc cat acc tat tat gcg gat agc gtg      192
Ser Phe Ile Ser Gly Ser Gly Ser His Thr Tyr Tyr Ala Asp Ser Val
     50                  55                  60

aaa ggc cgt ttt acc att tca cgt gat aat tcg aaa aac acc ctg tat      240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                 85                  90                  95

gcg cgt gct tat gat gtt tgg ggc caa ggc acc ctg gtg acg gtt agc      336
Ala Arg Ala Tyr Asp Val Trp Gly Gln Gly Thr Leu Val Thr Val Ser
            100                 105                 110

tca                                                                  339
Ser


<210> SEQ ID NO 14
<211> LENGTH: 113
<212> TYPE: PRT
<213> ORGANISM: human

<400> SEQUENCE: 14

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Asn Asn Asn
            20                  25                  30

Trp Met His Trp Val Arg Gln Ala Pro Gly Lys Gly Leu Glu Trp Val
        35                  40                  45

Ser Phe Ile Ser Gly Ser Gly Ser His Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Ala Tyr Asp Val Trp Gly Gln Gly Thr Leu Val Thr Val Ser
            100                 105                 110

Ser


<210> SEQ ID NO 15
<211> LENGTH: 327
<212> TYPE: DNA
<213> ORGANISM: human
<220> FEATURE:
<221> NAME/KEY: CDS
<222> LOCATION: (1)..(327)
<223> OTHER INFORMATION: Antibody-VL Region; MOR02614

<400> SEQUENCE: 15

gat atc gtg ctg acc cag ccg cct tca gtg agt ggc gca cca ggt cag       48
Asp Ile Val Leu Thr Gln Pro Pro Ser Val Ser Gly Ala Pro Gly Gln
  1               5                  10                  15

cgt gtg acc atc tcg tgt agc ggc agc agc agc aac att ggt ttt aat       96
Arg Val Thr Ile Ser Cys Ser Gly Ser Ser Ser Asn Ile Gly Phe Asn
            20                  25                  30

tat gtg aat tgg tac cag cag ttg ccc ggg acg gcg ccg aaa ctt ctg      144
Tyr Val Asn Trp Tyr Gln Gln Leu Pro Gly Thr Ala Pro Lys Leu Leu
        35                  40                  45

att tat ggt aat tct aag cgt ccc tca ggc gtg ccg gat cgt ttt agc      192
Ile Tyr Gly Asn Ser Lys Arg Pro Ser Gly Val Pro Asp Arg Phe Ser
     50                  55                  60
```

-continued

```
gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                  70                  75                  80

agc gaa gac gaa gcg gat tat tat tgc gct atg ttt tct cct gag ggt      288
Ser Glu Asp Glu Ala Asp Tyr Tyr Cys Ala Met Phe Ser Pro Glu Gly
                 85                  90                  95

gtg ttt ggc ggc ggc acg aag tta acc gtt ctt ggc cag                  327
Val Phe Gly Gly Gly Thr Lys Leu Thr Val Leu Gly Gln
            100                 105


<210> SEQ ID NO 16
<211> LENGTH: 109
<212> TYPE: PRT
<213> ORGANISM: human

<400> SEQUENCE: 16

Asp Ile Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Phe Asn
            20                  25                  30

Tyr Val Asn Trp Tyr Gln Gln Leu Pro Gly Thr Ala Pro Lys Leu Leu
        35                  40                  45

Ile Tyr Gly Asn Ser Lys Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Ala Met Phe Ser Pro Glu Gly
                 85                  90                  95

Val Phe Gly Gly Gly Thr Lys Leu Thr Val Leu Gly Gln
            100                 105


<210> SEQ ID NO 17
<211> LENGTH: 348
<212> TYPE: DNA
<213> ORGANISM: human
<220> FEATURE:
<221> NAME/KEY: CDS
<222> LOCATION: (1)..(348)
<223> OTHER INFORMATION: Antibody-VH Region; MOR02616

<400> SEQUENCE: 17

cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt cgt aat aat       96
Ser Leu Arg Leu Ser Cys Ala Ala Ser Gly Phe Thr Phe Arg Asn Asn
            20                  25                  30

gct atg cat tgg gtg cgc caa gcc cct ggg aag ggt ctc gag tgg gtg      144
Ala Met His Trp Val Arg Gln Ala Pro Gly Lys Gly Leu Glu Trp Val
        35                  40                  45

agc gct atc tct tct tct ggt agc ggt acc tat tat gcg gat agc gtg      192
Ser Ala Ile Ser Ser Ser Gly Ser Gly Thr Tyr Tyr Ala Asp Ser Val
     50                  55                  60

aaa ggc cgt ttt acc att tca cgt gat aat tcg aaa aac acc ctg tat      240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                 85                  90                  95

gcg cgt gtt att gtt ctt ttt gat tat tgg ggc caa ggc acc ctg gtg      336
Ala Arg Val Ile Val Leu Phe Asp Tyr Trp Gly Gln Gly Thr Leu Val
```

-continued

```
            100                 105                 110

acg gtt agc tca                                                     348
Thr Val Ser Ser
        115


<210> SEQ ID NO 18
<211> LENGTH: 116
<212> TYPE: PRT
<213> ORGANISM: human

<400> SEQUENCE: 18

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Arg Asn Asn
             20                  25                  30

Ala Met His Trp Val Arg Gln Ala Pro Gly Lys Gly Leu Glu Trp Val
         35                  40                  45

Ser Ala Ile Ser Ser Ser Gly Ser Gly Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Val Ile Val Leu Phe Asp Tyr Trp Gly Gln Gly Thr Leu Val
            100                 105                 110

Thr Val Ser Ser
        115


<210> SEQ ID NO 19
<211> LENGTH: 327
<212> TYPE: DNA
<213> ORGANISM: human
<220> FEATURE:
<221> NAME/KEY: CDS
<222> LOCATION: (1)..(327)
<223> OTHER INFORMATION: Antibody-VL Region; MOR02616

<400> SEQUENCE: 19

gat atc gtg ctg acc cag agc ccg gcg acc ctg agc ctg tct ccg ggc      48
Asp Ile Val Leu Thr Gln Ser Pro Ala Thr Leu Ser Leu Ser Pro Gly
  1               5                  10                  15

gaa cgt gcg acc ctg agc tgc aga gcg agc cag aat gtt cgt tct aat      96
Glu Arg Ala Thr Leu Ser Cys Arg Ala Ser Gln Asn Val Arg Ser Asn
             20                  25                  30

ctg gct tgg tac cag cag aaa cca ggt caa gca ccg cgt cta tta att     144
Leu Ala Trp Tyr Gln Gln Lys Pro Gly Gln Ala Pro Arg Leu Leu Ile
         35                  40                  45

tat ggt gct tct aat cgt gca act ggg gtc ccg gcg cgt ttt agc ggc     192
Tyr Gly Ala Ser Asn Arg Ala Thr Gly Val Pro Ala Arg Phe Ser Gly
     50                  55                  60

tct gga tcc ggc acg gat ttt acc ctg acc att agc agc ctg gaa cct     240
Ser Gly Ser Gly Thr Asp Phe Thr Leu Thr Ile Ser Ser Leu Glu Pro
 65                  70                  75                  80

gaa gac ttt gcg gtt tat tat tgc ctt cag aag tac tct att cct ttt     288
Glu Asp Phe Ala Val Tyr Tyr Cys Leu Gln Lys Tyr Ser Ile Pro Phe
                 85                  90                  95

acc ttt ggc cag ggt acg aaa gtt gaa att aaa cgt acg                 327
Thr Phe Gly Gln Gly Thr Lys Val Glu Ile Lys Arg Thr
            100                 105
```

-continued

<210> SEQ ID NO 20
<211> LENGTH: 109
<212> TYPE: PRT
<213> ORGANISM: human

<400> SEQUENCE: 20

```
Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Asn Val Arg Ser Asn
             20                  25                  30

Leu Ala Trp Tyr Gln Gln Lys Pro Gly Gln Ala Pro Arg Leu Leu Ile
         35                  40                  45

Tyr Gly Ala Ser Asn Arg Ala Thr Gly Val Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Leu Gln Lys Tyr Ser Ile Pro Phe
                 85                  90                  95

Thr Phe Gly Gln Gly Thr Lys Val Glu Ile Lys Arg Thr
            100                 105
```

<210> SEQ ID NO 21
<211> LENGTH: 348
<212> TYPE: DNA
<213> ORGANISM: human
<220> FEATURE:
<221> NAME/KEY: CDS
<222> LOCATION: (1)..(348)
<223> OTHER INFORMATION: Antibody-VH Region; MOR02618

<400> SEQUENCE: 21

```
cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt aat aat tat       96
Ser Leu Arg Leu Ser Cys Ala Ala Ser Gly Phe Thr Phe Asn Asn Tyr
             20                  25                  30

ggt atg act tgg gtg cgc caa gcc cct ggg aag ggt ctc gag tgg gtg      144
Gly Met Thr Trp Val Arg Gln Ala Pro Gly Lys Gly Leu Glu Trp Val
         35                  40                  45

agc tct atc tat ggt tat ggt agc aat acc tat tat gcg gat agc gtg      192
Ser Ser Ile Tyr Gly Tyr Gly Ser Asn Thr Tyr Tyr Ala Asp Ser Val
     50                  55                  60

aaa ggc cgt ttt acc att tca cgt gat aat tcg aaa aac acc ctg tat      240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                 85                  90                  95

gcg cgt aat tat tgg gtt ttt gct tat tgg ggc caa ggc acc ctg gtg      336
Ala Arg Asn Tyr Trp Val Phe Ala Tyr Trp Gly Gln Gly Thr Leu Val
            100                 105                 110

acg gtt agc tca                                                      348
Thr Val Ser Ser
        115
```

<210> SEQ ID NO 22
<211> LENGTH: 116
<212> TYPE: PRT
<213> ORGANISM: human

<400> SEQUENCE: 22

-continued

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Asn Asn Tyr
             20                  25                  30

Gly Met Thr Trp Val Arg Gln Ala Pro Gly Lys Gly Leu Glu Trp Val
         35                  40                  45

Ser Ser Ile Tyr Gly Tyr Gly Ser Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Tyr Trp Val Phe Ala Tyr Trp Gly Gln Gly Thr Leu Val
            100                 105                 110

Thr Val Ser Ser
        115


<210> SEQ ID NO 23
<211> LENGTH: 330
<212> TYPE: DNA
<213> ORGANISM: human
<220> FEATURE:
<221> NAME/KEY: CDS
<222> LOCATION: (1)..(330)
<223> OTHER INFORMATION: Antibody-VL Region; MOR02618

<400> SEQUENCE: 23

gat atc gaa ctg acc cag ccg cct tca gtg agc gtt gca cca ggt cag       48
Asp Ile Glu Leu Thr Gln Pro Pro Ser Val Ser Val Ala Pro Gly Gln
  1               5                  10                  15

acc gcg cgt atc tcg tgt agc ggc gat aat att cct ggt aag tct gtt       96
Thr Ala Arg Ile Ser Cys Ser Gly Asp Asn Ile Pro Gly Lys Ser Val
             20                  25                  30

cat tgg tac cag cag aaa ccc ggg cag gcg cca gtt ctt gtg att tat      144
His Trp Tyr Gln Gln Lys Pro Gly Gln Ala Pro Val Leu Val Ile Tyr
         35                  40                  45

ggt aag atg aat cgt ccc tca ggc atc ccg gaa cgc ttt agc gga tcc      192
Gly Lys Met Asn Arg Pro Ser Gly Ile Pro Glu Arg Phe Ser Gly Ser
     50                  55                  60

aac agc ggc aac acc gcg acc ctg acc att agc ggc act cag gcg gaa      240
Asn Ser Gly Asn Thr Ala Thr Leu Thr Ile Ser Gly Thr Gln Ala Glu
 65                  70                  75                  80

gac gaa gcg gat tat tat tgc cag tct tat gat aat ttt aat gat tct      288
Asp Glu Ala Asp Tyr Tyr Cys Gln Ser Tyr Asp Asn Phe Asn Asp Ser
                 85                  90                  95

gtt gtg ttt ggc ggc ggc acg aag tta acc gtt ctt ggc cag              330
Val Val Phe Gly Gly Gly Thr Lys Leu Thr Val Leu Gly Gln
            100                 105                 110


<210> SEQ ID NO 24
<211> LENGTH: 110
<212> TYPE: PRT
<213> ORGANISM: human

<400> SEQUENCE: 24

Asp Ile Glu Leu Thr Gln Pro Pro Ser Val Ser Val Ala Pro Gly Gln
  1               5                  10                  15

Thr Ala Arg Ile Ser Cys Ser Gly Asp Asn Ile Pro Gly Lys Ser Val
             20                  25                  30
```

-continued

```
His Trp Tyr Gln Gln Lys Pro Gly Gln Ala Pro Val Leu Val Ile Tyr
         35                  40                  45

Gly Lys Met Asn Arg Pro Ser Gly Ile Pro Glu Arg Phe Ser Gly Ser
     50                  55                  60

Asn Ser Gly Asn Thr Ala Thr Leu Thr Ile Ser Gly Thr Gln Ala Glu
 65                  70                  75                  80

Asp Glu Ala Asp Tyr Tyr Cys Gln Ser Tyr Asp Asn Phe Asn Asp Ser
                 85                  90                  95

Val Val Phe Gly Gly Gly Thr Lys Leu Thr Val Leu Gly Gln
            100                 105                 110


<210> SEQ ID NO 25
<211> LENGTH: 333
<212> TYPE: DNA
<213> ORGANISM: human
<220> FEATURE:
<221> NAME/KEY: CDS
<222> LOCATION: (1)..(333)
<223> OTHER INFORMATION: Antibody-VH Region; MOR02619

<400> SEQUENCE: 25

cag gtg caa ttg caa gaa agt ggt ccg ggc ctg gtg aaa ccg ggc gaa       48
Gln Val Gln Leu Gln Glu Ser Gly Pro Gly Leu Val Lys Pro Gly Glu
  1               5                  10                  15

acc ctg agc ctg acc tgc acc gtt tcc gga ggc agc att tct tct tat       96
Thr Leu Ser Leu Thr Cys Thr Val Ser Gly Gly Ser Ile Ser Ser Tyr
             20                  25                  30

tat tgg tct tgg att cgc cag gcc cct ggg aag ggt ctc gag tgg att      144
Tyr Trp Ser Trp Ile Arg Gln Ala Pro Gly Lys Gly Leu Glu Trp Ile
         35                  40                  45

ggc atc ggt cat tgg ggc tct acc cag tat aat ccg agc ctg aaa ggc      192
Gly Ile Gly His Trp Gly Ser Thr Gln Tyr Asn Pro Ser Leu Lys Gly
     50                  55                  60

cgg gtg acc att agc gtt gat act tcg aaa aac cag ttt agc ctg aaa      240
Arg Val Thr Ile Ser Val Asp Thr Ser Lys Asn Gln Phe Ser Leu Lys
 65                  70                  75                  80

ctg agc agc gtg acg gcg gaa gat acg gcc gtg tat tat tgc gcg cgt      288
Leu Ser Ser Val Thr Ala Glu Asp Thr Ala Val Tyr Tyr Cys Ala Arg
                 85                  90                  95

ttt ttt gat gtt tgg ggc caa ggc acc ctg gtg acg gtt agc tca          333
Phe Phe Asp Val Trp Gly Gln Gly Thr Leu Val Thr Val Ser Ser
            100                 105                 110


<210> SEQ ID NO 26
<211> LENGTH: 111
<212> TYPE: PRT
<213> ORGANISM: human

<400> SEQUENCE: 26

Gln Val Gln Leu Gln Glu Ser Gly Pro Gly Leu Val Lys Pro Gly Glu
  1               5                  10                  15

Thr Leu Ser Leu Thr Cys Thr Val Ser Gly Gly Ser Ile Ser Ser Tyr
             20                  25                  30

Tyr Trp Ser Trp Ile Arg Gln Ala Pro Gly Lys Gly Leu Glu Trp Ile
         35                  40                  45

Gly Ile Gly His Trp Gly Ser Thr Gln Tyr Asn Pro Ser Leu Lys Gly
     50                  55                  60

Arg Val Thr Ile Ser Val Asp Thr Ser Lys Asn Gln Phe Ser Leu Lys
 65                  70                  75                  80

Leu Ser Ser Val Thr Ala Glu Asp Thr Ala Val Tyr Tyr Cys Ala Arg
```

-continued

```
                85                  90                  95

Phe Phe Asp Val Trp Gly Gln Gly Thr Leu Val Thr Val Ser Ser
            100                 105                 110


<210> SEQ ID NO 27
<211> LENGTH: 333
<212> TYPE: DNA
<213> ORGANISM: human
<220> FEATURE:
<221> NAME/KEY: CDS
<222> LOCATION: (1)..(333)
<223> OTHER INFORMATION: Antibody-VL Region; MOR02619

<400> SEQUENCE: 27

gat atc gtg ctg acc cag ccg cct tca gtg agt ggc gca cca ggt cag       48
Asp Ile Val Leu Thr Gln Pro Pro Ser Val Ser Gly Ala Pro Gly Gln
  1               5                  10                  15

cgt gtg acc atc tcg tgt agc ggc agc agc agc aac att ggt tct aat       96
Arg Val Thr Ile Ser Cys Ser Gly Ser Ser Ser Asn Ile Gly Ser Asn
             20                  25                  30

act gtg cgt tgg tac cag cag ttg ccc ggg acg gcg ccg aaa ctt ctg      144
Thr Val Arg Trp Tyr Gln Gln Leu Pro Gly Thr Ala Pro Lys Leu Leu
         35                  40                  45

att tat tct aat aat aag cgt ccc tca ggc gtg ccg gat cgt ttt agc      192
Ile Tyr Ser Asn Asn Lys Arg Pro Ser Gly Val Pro Asp Arg Phe Ser
     50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                  70                  75                  80

agc gaa gac gaa gcg gat tat tat tgc cag tct tgg gat ggt gct tct      288
Ser Glu Asp Glu Ala Asp Tyr Tyr Cys Gln Ser Trp Asp Gly Ala Ser
                85                  90                  95

act ggt gtg ttt ggc ggc ggc acg aag tta acc gtt ctt ggc cag          333
Thr Gly Val Phe Gly Gly Gly Thr Lys Leu Thr Val Leu Gly Gln
            100                 105                 110


<210> SEQ ID NO 28
<211> LENGTH: 111
<212> TYPE: PRT
<213> ORGANISM: human

<400> SEQUENCE: 28

Asp Ile Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
             20                  25                  30

Thr Val Arg Trp Tyr Gln Gln Leu Pro Gly Thr Ala Pro Lys Leu Leu
         35                  40                  45

Ile Tyr Ser Asn Asn Lys Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Ser Trp Asp Gly Ala Ser
                85                  90                  95

Thr Gly Val Phe Gly Gly Gly Thr Lys Leu Thr Val Leu Gly Gln
            100                 105                 110


<210> SEQ ID NO 29
<211> LENGTH: 348
<212> TYPE: DNA
<213> ORGANISM: human
```

-continued

```
<220> FEATURE:
<221> NAME/KEY: CDS
<222> LOCATION: (1)..(348)
<223> OTHER INFORMATION: Antibody-VH Region; MOR02622

<400> SEQUENCE: 29

cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt tct aat tat       96
Ser Leu Arg Leu Ser Cys Ala Ala Ser Gly Phe Thr Phe Ser Asn Tyr
             20                  25                  30

gct atg act tgg gtg cgc caa gcc cct ggg aag ggt ctc gag tgg gtg      144
Ala Met Thr Trp Val Arg Gln Ala Pro Gly Lys Gly Leu Glu Trp Val
         35                  40                  45

agc ggt atc tct tac aag tct agc tct acc tat tat gcg gat agc gtg      192
Ser Gly Ile Ser Tyr Lys Ser Ser Ser Thr Tyr Tyr Ala Asp Ser Val
     50                  55                  60

aaa ggc cgt ttt acc att tca cgt gat aat tcg aaa aac acc ctg tat      240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                 85                  90                  95

gcg cgt ggt ctt gtt act ttt gat aat tgg ggc caa ggc acc ctg gtg      336
Ala Arg Gly Leu Val Thr Phe Asp Asn Trp Gly Gln Gly Thr Leu Val
            100                 105                 110

acg gtt agc tca                                                      348
Thr Val Ser Ser
        115


<210> SEQ ID NO 30
<211> LENGTH: 116
<212> TYPE: PRT
<213> ORGANISM: human

<400> SEQUENCE: 30

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Ala Met Thr Trp Val Arg Gln Ala Pro Gly Lys Gly Leu Glu Trp Val
         35                  40                  45

Ser Gly Ile Ser Tyr Lys Ser Ser Ser Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Gly Leu Val Thr Phe Asp Asn Trp Gly Gln Gly Thr Leu Val
            100                 105                 110

Thr Val Ser Ser
        115


<210> SEQ ID NO 31
<211> LENGTH: 339
<212> TYPE: DNA
<213> ORGANISM: human
<220> FEATURE:
<221> NAME/KEY: CDS
<222> LOCATION: (1)..(339)
```

-continued

```
<223> OTHER INFORMATION: Antibody-VL Region; MOR02622

<400> SEQUENCE: 31

gat atc gca ctg acc cag cca gct tca gtg agc ggc tca cca ggt cag       48
Asp Ile Ala Leu Thr Gln Pro Ala Ser Val Ser Gly Ser Pro Gly Gln
  1               5                  10                  15

agc att acc atc tcg tgt acg ggt act agc agc gat ggt ggt act tat       96
Ser Ile Thr Ile Ser Cys Thr Gly Thr Ser Ser Asp Gly Gly Thr Tyr
             20                  25                  30

aat ttt gtg tct tgg tac cag cag cat ccc ggg aag gcg ccg aaa ctt      144
Asn Phe Val Ser Trp Tyr Gln Gln His Pro Gly Lys Ala Pro Lys Leu
         35                  40                  45

atg att tat cgt gtt tct aat cgt ccc tca ggc gtg agc aac cgt ttt      192
Met Ile Tyr Arg Val Ser Asn Arg Pro Ser Gly Val Ser Asn Arg Phe
     50                  55                  60

agc gga tcc aaa agc ggc aac acc gcg agc ctg acc att agc ggc ctg      240
Ser Gly Ser Lys Ser Gly Asn Thr Ala Ser Leu Thr Ile Ser Gly Leu
 65                  70                  75                  80

caa gcg gaa gac gaa gcg gat tat tat tgc tct tct tgg act cat tct      288
Gln Ala Glu Asp Glu Ala Asp Tyr Tyr Cys Ser Ser Trp Thr His Ser
                 85                  90                  95

ttt act gat tat gtg ttt ggc ggc ggc acg aag tta acc gtt ctt ggc      336
Phe Thr Asp Tyr Val Phe Gly Gly Gly Thr Lys Leu Thr Val Leu Gly
            100                 105                 110

cag                                                                  339
Gln


<210> SEQ ID NO 32
<211> LENGTH: 113
<212> TYPE: PRT
<213> ORGANISM: human

<400> SEQUENCE: 32

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Gly Gly Thr Tyr
             20                  25                  30

Asn Phe Val Ser Trp Tyr Gln Gln His Pro Gly Lys Ala Pro Lys Leu
         35                  40                  45

Met Ile Tyr Arg Val Ser Asn Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Ser Ser Trp Thr His Ser
                 85                  90                  95

Phe Thr Asp Tyr Val Phe Gly Gly Gly Thr Lys Leu Thr Val Leu Gly
            100                 105                 110

Gln


<210> SEQ ID NO 33
<211> LENGTH: 348
<212> TYPE: DNA
<213> ORGANISM: human
<220> FEATURE:
<221> NAME/KEY: CDS
<222> LOCATION: (1)..(348)
<223> OTHER INFORMATION: Antibody-VH Region; MOR02715

<400> SEQUENCE: 33

cag gtg caa ttg gtg gaa agc ggc ggc ggc ctg gtg caa ccg ggc ggc       48
```

-continued

```
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt tct tct tat        96
Ser Leu Arg Leu Ser Cys Ala Ala Ser Gly Phe Thr Phe Ser Ser Tyr
             20                  25                  30

ggt atg cat tgg gtg cgc caa gcc cct ggg aag ggt ctc gag tgg gtg       144
Gly Met His Trp Val Arg Gln Ala Pro Gly Lys Gly Leu Glu Trp Val
         35                  40                  45

agc gtt atc tct tct tct ggt agc tat atc tat tat gcg gat agc gtg       192
Ser Val Ile Ser Ser Ser Gly Ser Tyr Ile Tyr Tyr Ala Asp Ser Val
     50                  55                  60

aaa ggc cgt ttt acc att tca cgt gat aat tcg aaa aac acc ctg tat       240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc       288
Leu Gln Met Asn Ser Leu Arg Ala Glu Asp Thr Ala Val Tyr Tyr Cys
                 85                  90                  95

gcg cgt aat aag gtt ggt ttt gat gtt tgg ggc caa ggc acc ctg gtg       336
Ala Arg Asn Lys Val Gly Phe Asp Val Trp Gly Gln Gly Thr Leu Val
            100                 105                 110

acg gtt agc tca                                                       348
Thr Val Ser Ser
        115


<210> SEQ ID NO 34
<211> LENGTH: 116
<212> TYPE: PRT
<213> ORGANISM: human

<400> SEQUENCE: 34

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ser Val Ile Ser Ser Ser Gly Ser Tyr Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Lys Val Gly Phe Asp Val Trp Gly Gln Gly Thr Leu Val
            100                 105                 110

Thr Val Ser Ser
        115


<210> SEQ ID NO 35
<211> LENGTH: 339
<212> TYPE: DNA
<213> ORGANISM: human
<220> FEATURE:
<221> NAME/KEY: CDS
<222> LOCATION: (1)..(339)
<223> OTHER INFORMATION: Antibody-VL Region; MOR02715

<400> SEQUENCE: 35

gat atc gca ctg acc cag cca gct tca gtg agc ggc tca cca ggt cag        48
Asp Ile Ala Leu Thr Gln Pro Ala Ser Val Ser Gly Ser Pro Gly Gln
  1               5                  10                  15
```

-continued

```
agc att acc atc tcg tgt acg ggt act agc agc gat ggt ggt ggt tat        96
Ser Ile Thr Ile Ser Cys Thr Gly Thr Ser Ser Asp Gly Gly Gly Tyr
            20                  25                  30

aat act gtg tct tgg tac cag cag cat ccc ggg aag gcg ccg aaa ctt       144
Asn Thr Val Ser Trp Tyr Gln Gln His Pro Gly Lys Ala Pro Lys Leu
        35                  40                  45

atg att tat tat gtt cat aag cgt ccc tca ggc gtg agc aac cgt ttt       192
Met Ile Tyr Tyr Val His Lys Arg Pro Ser Gly Val Ser Asn Arg Phe
    50                  55                  60

agc gga tcc aaa agc ggc aac acc gcg agc ctg acc att agc ggc ctg       240
Ser Gly Ser Lys Ser Gly Asn Thr Ala Ser Leu Thr Ile Ser Gly Leu
65                  70                  75                  80

caa gcg gaa gac gaa gcg gat tat tat tgc cag gct tgg gat aat cag       288
Gln Ala Glu Asp Glu Ala Asp Tyr Tyr Cys Gln Ala Trp Asp Asn Gln
                85                  90                  95

ggt atg aag tat gtg ttt ggc ggc ggc acg aag tta acc gtt ctt ggc       336
Gly Met Lys Tyr Val Phe Gly Gly Gly Thr Lys Leu Thr Val Leu Gly
            100                 105                 110

cag                                                                   339
Gln


<210> SEQ ID NO 36
<211> LENGTH: 113
<212> TYPE: PRT
<213> ORGANISM: human

<400> SEQUENCE: 36

Asp Ile Ala Leu Thr Gln Pro Ala Ser Val Ser Gly Ser Pro Gly Gln
1               5                   10                  15

Ser Ile Thr Ile Ser Cys Thr Gly Thr Ser Ser Asp Gly Gly Gly Tyr
            20                  25                  30

Asn Thr Val Ser Trp Tyr Gln Gln His Pro Gly Lys Ala Pro Lys Leu
        35                  40                  45

Met Ile Tyr Tyr Val His Lys Arg Pro Ser Gly Val Ser Asn Arg Phe
    50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Gln Ala Trp Asp Asn Gln
                85                  90                  95

Gly Met Lys Tyr Val Phe Gly Gly Gly Thr Lys Leu Thr Val Leu Gly
            100                 105                 110

Gln


<210> SEQ ID NO 37
<211> LENGTH: 345
<212> TYPE: DNA
<213> ORGANISM: human
<220> FEATURE:
<221> NAME/KEY: CDS
<222> LOCATION: (1)..(345)
<223> OTHER INFORMATION: Antibody-VH Region; MOR02718

<400> SEQUENCE: 37

cag gtg caa ttg gtg gaa agc ggc ggc ggc ctg gtg caa ccg ggc ggc        48
Gln Val Gln Leu Val Glu Ser Gly Gly Gly Leu Val Gln Pro Gly Gly
1               5                   10                  15

agc ctg cgt ctg agc tgc gcg gcc tcc gga ttt acc ttt aat tct aat        96
Ser Leu Arg Leu Ser Cys Ala Ala Ser Gly Phe Thr Phe Asn Ser Asn
            20                  25                  30

gct atg cat tgg gtg cgc caa gcc cct ggg aag ggt ctc gag tgg gtg       144
```

```
Ala Met His Trp Val Arg Gln Ala Pro Gly Lys Gly Leu Glu Trp Val
        35                  40                  45

agc ttt atc tct ggt tct ggt agc tct acc tat tat gcg gat agc gtg      192
Ser Phe Ile Ser Gly Ser Gly Ser Ser Thr Tyr Tyr Ala Asp Ser Val
    50                  55                  60

aaa ggc cgt ttt acc att tca cgt gat aat tcg aaa aac acc ctg tat      240
Lys Gly Arg Phe Thr Ile Ser Arg Asp Asn Ser Lys Asn Thr Leu Tyr
65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                85                  90                  95

gcg cgt ggt tgg ttt ttt gct cat tgg ggc caa ggc acc ctg gtg acg      336
Ala Arg Gly Trp Phe Phe Ala His Trp Gly Gln Gly Thr Leu Val Thr
            100                 105                 110

gtt agc tca                                                          345
Val Ser Ser
        115


<210> SEQ ID NO 38
<211> LENGTH: 115
<212> TYPE: PRT
<213> ORGANISM: human

<400> SEQUENCE: 38

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Asn Ser Asn
            20                  25                  30

Ala Met His Trp Val Arg Gln Ala Pro Gly Lys Gly Leu Glu Trp Val
        35                  40                  45

Ser Phe Ile Ser Gly Ser Gly Ser Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Trp Phe Phe Ala His Trp Gly Gln Gly Thr Leu Val Thr
            100                 105                 110

Val Ser Ser
        115


<210> SEQ ID NO 39
<211> LENGTH: 327
<212> TYPE: DNA
<213> ORGANISM: human
<220> FEATURE:
<221> NAME/KEY: CDS
<222> LOCATION: (1)..(327)
<223> OTHER INFORMATION: Antibody-VL Region; MOR02718

<400> SEQUENCE: 39

gat atc gtg ctg acc cag agc ccg gcg acc ctg agc ctg tct ccg ggc       48
Asp Ile Val Leu Thr Gln Ser Pro Ala Thr Leu Ser Leu Ser Pro Gly
1               5                   10                  15

gaa cgt gcg acc ctg agc tgc aga gcg agc cag tct ggt cgt ggt aat       96
Glu Arg Ala Thr Leu Ser Cys Arg Ala Ser Gln Ser Gly Arg Gly Asn
            20                  25                  30

ctg gct tgg tac cag cag aaa cca ggt caa gca ccg cgt cta tta att      144
Leu Ala Trp Tyr Gln Gln Lys Pro Gly Gln Ala Pro Arg Leu Leu Ile
        35                  40                  45
```

-continued

```
tat gat gct tct aat cgt gca act ggg gtc ccg gcg cgt ttt agc ggc      192
Tyr Asp Ala Ser Asn Arg Ala Thr Gly Val Pro Ala Arg Phe Ser Gly
     50                  55                  60

tct gga tcc ggc acg gat ttt acc ctg acc att agc agc ctg gaa cct      240
Ser Gly Ser Gly Thr Asp Phe Thr Leu Thr Ile Ser Ser Leu Glu Pro
 65                  70                  75                  80

gaa gac ttt gcg gtt tat tat tgc ttt cag tat tct tct gtt cct ctt      288
Glu Asp Phe Ala Val Tyr Tyr Cys Phe Gln Tyr Ser Ser Val Pro Leu
                 85                  90                  95

acc ttt ggc cag ggt acg aaa gtt gaa att aaa cgt acg                  327
Thr Phe Gly Gln Gly Thr Lys Val Glu Ile Lys Arg Thr
            100                 105
```

```
<210> SEQ ID NO 40
<211> LENGTH: 109
<212> TYPE: PRT
<213> ORGANISM: human

<400> SEQUENCE: 40

Asp Ile Val Leu Thr Gln Ser Pro Ala Thr Leu Ser Leu Ser Pro Gly
  1               5                  10                  15

Glu Arg Ala Thr Leu Ser Cys Arg Ala Ser Gln Ser Gly Arg Gly Asn
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Val Pro Ala Arg Phe Ser Gly
     50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Phe Gln Tyr Ser Ser Val Pro Leu
                 85                  90                  95

Thr Phe Gly Gln Gly Thr Lys Val Glu Ile Lys Arg Thr
            100                 105
```

```
<210> SEQ ID NO 41
<211> LENGTH: 342
<212> TYPE: DNA
<213> ORGANISM: human
<220> FEATURE:
<221> NAME/KEY: CDS
<222> LOCATION: (1)..(342)
<223> OTHER INFORMATION: Antibody-VH Region; MOR02721

<400> SEQUENCE: 41

cag gtg caa ttg gtt cag agc ggc gcg gaa gtg aaa aaa ccg ggc gaa       48
Gln Val Gln Leu Val Gln Ser Gly Ala Glu Val Lys Lys Pro Gly Glu
  1               5                  10                  15

agc ctg aaa att agc tgc aaa ggt tcc gga tat tcc ttt act tct tat       96
Ser Leu Lys Ile Ser Cys Lys Gly Ser Gly Tyr Ser Phe Thr Ser Tyr
            20                  25                  30

tat att aat tgg gtg cgc cag atg cct ggg aag ggt ctc gag tgg atg      144
Tyr Ile Asn Trp Val Arg Gln Met Pro Gly Lys Gly Leu Glu Trp Met
        35                  40                  45

ggc att atc tat ccg tct act agc cgt acc att tat tct ccg agc ttt      192
Gly Ile Ile Tyr Pro Ser Thr Ser Arg Thr Ile Tyr Ser Pro Ser Phe
     50                  55                  60

cag ggc cag gtg acc att agc gcg gat aaa agc att agc acc gcg tat      240
Gln Gly Gln Val Thr Ile Ser Ala Asp Lys Ser Ile Ser Thr Ala Tyr
 65                  70                  75                  80

ctt caa tgg agc agc ctg aaa gcg agc gat acg gcc atg tat tat tgc      288
Leu Gln Trp Ser Ser Leu Lys Ala Ser Asp Thr Ala Met Tyr Tyr Cys
```

-continued

```
                85                  90                  95

gcg cgt tat cat ggt gct ttt tgg ggc caa ggc acc ctg gtg acg gtt       336
Ala Arg Tyr His Gly Ala Phe Trp Gly Gln Gly Thr Leu Val Thr Val
            100                 105                 110

agc tca                                                               342
Ser Ser


<210> SEQ ID NO 42
<211> LENGTH: 114
<212> TYPE: PRT
<213> ORGANISM: human

<400> SEQUENCE: 42

Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
            20                  25                  30

Tyr Ile Asn Trp Val Arg Gln Met Pro Gly Lys Gly Leu Glu Trp Met
        35                  40                  45

Gly Ile Ile Tyr Pro Ser Thr Ser Arg Thr Ile Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala Arg Tyr His Gly Ala Phe Trp Gly Gln Gly Thr Leu Val Thr Val
            100                 105                 110

Ser Ser


<210> SEQ ID NO 43
<211> LENGTH: 342
<212> TYPE: DNA
<213> ORGANISM: human
<220> FEATURE:
<221> NAME/KEY: CDS
<222> LOCATION: (1)..(342)
<223> OTHER INFORMATION: Antibody-VL Region; MOR02721

<400> SEQUENCE: 43

cag gtg caa ttg gtt cag agc ggc gcg gaa gtg aaa aaa ccg ggc gaa        48
Gln Val Gln Leu Val Gln Ser Gly Ala Glu Val Lys Lys Pro Gly Glu
  1               5                  10                  15

agc ctg aaa att agc tgc aaa ggt tcc gga tat tcc ttt act tct tat        96
Ser Leu Lys Ile Ser Cys Lys Gly Ser Gly Tyr Ser Phe Thr Ser Tyr
            20                  25                  30

tat att aat tgg gtg cgc cag atg cct ggg aag ggt ctc gag tgg atg       144
Tyr Ile Asn Trp Val Arg Gln Met Pro Gly Lys Gly Leu Glu Trp Met
        35                  40                  45

ggc att atc tat ccg tct act agc cgt acc att tat tct ccg agc ttt       192
Gly Ile Ile Tyr Pro Ser Thr Ser Arg Thr Ile Tyr Ser Pro Ser Phe
     50                  55                  60

cag ggc cag gtg acc att agc gcg gat aaa agc att agc acc gcg tat       240
Gln Gly Gln Val Thr Ile Ser Ala Asp Lys Ser Ile Ser Thr Ala Tyr
 65                  70                  75                  80

ctt caa tgg agc agc ctg aaa gcg agc gat acg gcc atg tat tat tgc       288
Leu Gln Trp Ser Ser Leu Lys Ala Ser Asp Thr Ala Met Tyr Tyr Cys
                85                  90                  95

gcg cgt tat cat ggt gct ttt tgg ggc caa ggc acc ctg gtg acg gtt       336
Ala Arg Tyr His Gly Ala Phe Trp Gly Gln Gly Thr Leu Val Thr Val
            100                 105                 110
```

-continued

```
agc tca                                                          342
Ser Ser


<210> SEQ ID NO 44
<211> LENGTH: 114
<212> TYPE: PRT
<213> ORGANISM: human

<400> SEQUENCE: 44

Gln Val Gln Leu Val Gln Ser Gly Ala Glu Val Lys Lys Pro Gly Glu
  1               5                  10                  15

Ser Leu Lys Ile Ser Cys Lys Gly Ser Gly Tyr Ser Phe Thr Ser Tyr
             20                  25                  30

Tyr Ile Asn Trp Val Arg Gln Met Pro Gly Lys Gly Leu Glu Trp Met
         35                  40                  45

Gly Ile Ile Tyr Pro Ser Thr Ser Arg Thr Ile Tyr Ser Pro Ser Phe
     50                  55                  60

Gln Gly Gln Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                 85                  90                  95

Ala Arg Tyr His Gly Ala Phe Trp Gly Gln Gly Thr Leu Val Thr Val
            100                 105                 110

Ser Ser


<210> SEQ ID NO 45
<211> LENGTH: 339
<212> TYPE: DNA
<213> ORGANISM: human
<220> FEATURE:
<221> NAME/KEY: CDS
<222> LOCATION: (1)..(339)
<223> OTHER INFORMATION: Antibody-VH Region; MOR02722

<400> SEQUENCE: 45

cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt tct tct aat       96
Ser Leu Arg Leu Ser Cys Ala Ala Ser Gly Phe Thr Phe Ser Ser Asn
             20                  25                  30

gct att cat tgg gtg cgc caa gcc cct ggg aag ggt ctc gag tgg gtg      144
Ala Ile His Trp Val Arg Gln Ala Pro Gly Lys Gly Leu Glu Trp Val
         35                  40                  45

agc tct atc tct ggt tct ggt agc aat acc tat tat gcg gat agc gtg      192
Ser Ser Ile Ser Gly Ser Gly Ser Asn Thr Tyr Tyr Ala Asp Ser Val
     50                  55                  60

aaa ggc cgt ttt acc att tca cgt gat aat tcg aaa aac acc ctg tat      240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                 85                  90                  95

gcg cgt ttt att gct tct tgg ggc caa ggc acc ctg gtg acg gtt agc      336
Ala Arg Phe Ile Ala Ser Trp Gly Gln Gly Thr Leu Val Thr Val Ser
            100                 105                 110

tca                                                                  339
Ser
```

-continued

<210> SEQ ID NO 46
<211> LENGTH: 113
<212> TYPE: PRT
<213> ORGANISM: human

<400> SEQUENCE: 46

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Asn
             20                  25                  30

Ala Ile His Trp Val Arg Gln Ala Pro Gly Lys Gly Leu Glu Trp Val
         35                  40                  45

Ser Ser Ile Ser Gly Ser Gly Ser Asn Thr Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Phe Ile Ala Ser Trp Gly Gln Gly Thr Leu Val Thr Val Ser
            100                 105                 110

Ser
```

<210> SEQ ID NO 47
<211> LENGTH: 342
<212> TYPE: DNA
<213> ORGANISM: human
<220> FEATURE:
<221> NAME/KEY: CDS
<222> LOCATION: (1)..(342)
<223> OTHER INFORMATION: Antibody-VL Region; MOR02722

<400> SEQUENCE: 47

```
gat atc gtg atg acc cag agc cca ctg agc ctg cca gtg act ccg ggc       48
Asp Ile Val Met Thr Gln Ser Pro Leu Ser Leu Pro Val Thr Pro Gly
  1               5                  10                  15

gag cct gcg agc att agc tgc aga agc agc caa agc ctg gtt cat tct       96
Glu Pro Ala Ser Ile Ser Cys Arg Ser Ser Gln Ser Leu Val His Ser
             20                  25                  30

aat ggc tat act gat ctg aat tgg tac ctt caa aaa cca ggt caa agc      144
Asn Gly Tyr Thr Asp Leu Asn Trp Tyr Leu Gln Lys Pro Gly Gln Ser
         35                  40                  45

ccg cag cta tta att tat ctt ggt tct tat cgt gcc agt ggg gtc ccg      192
Pro Gln Leu Leu Ile Tyr Leu Gly Ser Tyr Arg Ala Ser Gly Val Pro
     50                  55                  60

gat cgt ttt agc ggc tct gga tcc ggc acc gat ttt acc ctg aaa att      240
Asp Arg Phe Ser Gly Ser Gly Ser Gly Thr Asp Phe Thr Leu Lys Ile
 65                  70                  75                  80

agc cgt gtg gaa gct gaa gac gtg ggc gtg tat tat tgc cag cag tat      288
Ser Arg Val Glu Ala Glu Asp Val Gly Val Tyr Tyr Cys Gln Gln Tyr
                 85                  90                  95

tct aat ttt cct ttt acc ttt ggc cag ggt acg aaa gtt gaa att aaa      336
Ser Asn Phe Pro Phe Thr Phe Gly Gln Gly Thr Lys Val Glu Ile Lys
            100                 105                 110

cgt acg                                                              342
Arg Thr
```

<210> SEQ ID NO 48
<211> LENGTH: 114
<212> TYPE: PRT
<213> ORGANISM: human

-continued

<400> SEQUENCE: 48

```
Asp Ile Val Met Thr Gln Ser Pro Leu Ser Leu Pro Val Thr Pro Gly
  1               5                  10                  15

Glu Pro Ala Ser Ile Ser Cys Arg Ser Ser Gln Ser Leu Val His Ser
             20                  25                  30

Asn Gly Tyr Thr Asp Leu Asn Trp Tyr Leu Gln Lys Pro Gly Gln Ser
         35                  40                  45

Pro Gln Leu Leu Ile Tyr Leu Gly Ser Tyr Arg Ala Ser Gly Val Pro
     50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Val Gly Val Tyr Tyr Cys Gln Gln Tyr
                 85                  90                  95

Ser Asn Phe Pro Phe Thr Phe Gly Gln Gly Thr Lys Val Glu Ile Lys
            100                 105                 110

Arg Thr
```

<210> SEQ ID NO 49
<211> LENGTH: 336
<212> TYPE: DNA
<213> ORGANISM: human
<220> FEATURE:
<221> NAME/KEY: CDS
<222> LOCATION: (1)..(336)
<223> OTHER INFORMATION: Antibody-VL Region; MOR03055

<400> SEQUENCE: 49

```
gat atc gtg ctg acc cag ccg cct tca gtg agt ggc gca cca ggt cag       48
Asp Ile Val Leu Thr Gln Pro Pro Ser Val Ser Gly Ala Pro Gly Gln
  1               5                  10                  15

cgt gtg acc atc tcg tgt agc ggc agc agc agc aac att ggt tct aat       96
Arg Val Thr Ile Ser Cys Ser Gly Ser Ser Ser Asn Ile Gly Ser Asn
             20                  25                  30

act gtg cgt tgg tac cag cag ttg ccc ggg acg gcg ccg aaa ctt ctg      144
Thr Val Arg Trp Tyr Gln Gln Leu Pro Gly Thr Ala Pro Lys Leu Leu
         35                  40                  45

att tat tct aat aat aag cgt ccc tca ggc gtg ccg gat cgt ttt agc      192
Ile Tyr Ser Asn Asn Lys Arg Pro Ser Gly Val Pro Asp Arg Phe Ser
     50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                  70                  75                  80

agc gaa gac gaa gcg gat tat tat tgc cag gct tgg act cgt gct cat      288
Ser Glu Asp Glu Ala Asp Tyr Tyr Cys Gln Ala Trp Thr Arg Ala His
                 85                  90                  95

cgt tat cct gtg ttt ggc ggc ggc acg aag tta acc gtt ctt ggc cag      336
Arg Tyr Pro Val Phe Gly Gly Gly Thr Lys Leu Thr Val Leu Gly Gln
            100                 105                 110
```

<210> SEQ ID NO 50
<211> LENGTH: 112
<212> TYPE: PRT
<213> ORGANISM: human

<400> SEQUENCE: 50

```
Asp Ile Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
             20                  25                  30
```

-continued

```
Thr Val Arg Trp Tyr Gln Gln Leu Pro Gly Thr Ala Pro Lys Leu Leu
        35                  40                  45

Ile Tyr Ser Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Gln Ala Trp Thr Arg Ala His
                85                  90                  95

Arg Tyr Pro Val Phe Gly Gly Gly Thr Lys Leu Thr Val Leu Gly Gln
            100                 105                 110


<210> SEQ ID NO 51
<211> LENGTH: 333
<212> TYPE: DNA
<213> ORGANISM: human
<220> FEATURE:
<221> NAME/KEY: CDS
<222> LOCATION: (1)..(333)
<223> OTHER INFORMATION: Antibody-VL Region; MOR03066

<400> SEQUENCE: 51

gat atc gtg ctg acc cag ccg cct tca gtg agt ggc gca cca ggt cag       48
Asp Ile Val Leu Thr Gln Pro Pro Ser Val Ser Gly Ala Pro Gly Gln
1               5                   10                  15

cgt gtg acc atc tcg tgt agc ggc agc agc agc aac att ggt tct aat       96
Arg Val Thr Ile Ser Cys Ser Gly Ser Ser Ser Asn Ile Gly Ser Asn
            20                  25                  30

act gtg cgt tgg tac cag cag ttg ccc ggg acg gcg ccg aaa ctt ctg      144
Thr Val Arg Trp Tyr Gln Gln Leu Pro Gly Thr Ala Pro Lys Leu Leu
        35                  40                  45

att tat tct aat aat aag cgt ccc tca ggc gtg ccg gat cgt ttt agc      192
Ile Tyr Ser Asn Asn Lys Arg Pro Ser Gly Val Pro Asp Arg Phe Ser
    50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
65                  70                  75                  80

agc gaa gac gaa gcg gat tat tat tgc tct tct tat gat act cag gtt      288
Ser Glu Asp Glu Ala Asp Tyr Tyr Cys Ser Ser Tyr Asp Thr Gln Val
                85                  90                  95

act cgt gtg ttt ggc ggc ggc acg aag tta acc gtt ctt ggc cag          333
Thr Arg Val Phe Gly Gly Gly Thr Lys Leu Thr Val Leu Gly Gln
            100                 105                 110


<210> SEQ ID NO 52
<211> LENGTH: 111
<212> TYPE: PRT
<213> ORGANISM: human

<400> SEQUENCE: 52

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Thr Val Arg Trp Tyr Gln Gln Leu Pro Gly Thr Ala Pro Lys Leu Leu
        35                  40                  45

Ile Tyr Ser Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Ser Ser Tyr Asp Thr Gln Val
```

-continued

```
                85                  90                  95

Thr Arg Val Phe Gly Gly Gly Thr Lys Leu Thr Val Leu Gly Gln
            100                 105                 110
```

<210> SEQ ID NO 53
<211> LENGTH: 333
<212> TYPE: DNA
<213> ORGANISM: human
<220> FEATURE:
<221> NAME/KEY: CDS
<222> LOCATION: (1)..(333)
<223> OTHER INFORMATION: Antibody-VL Region; MOR03075

<400> SEQUENCE: 53

```
gat atc gtg ctg acc cag ccg cct tca gtg agt ggc gca cca ggt cag       48
Asp Ile Val Leu Thr Gln Pro Pro Ser Val Ser Gly Ala Pro Gly Gln
  1               5                  10                  15

cgt gtg acc atc tcg tgt agc ggc agc agc agc aac att ggt tct aat       96
Arg Val Thr Ile Ser Cys Ser Gly Ser Ser Ser Asn Ile Gly Ser Asn
            20                  25                  30

act gtg cgt tgg tac cag cag ttg ccc ggg acg gcg ccg aaa ctt ctg      144
Thr Val Arg Trp Tyr Gln Gln Leu Pro Gly Thr Ala Pro Lys Leu Leu
        35                  40                  45

att tat tct aat aat aag cgt ccc tca ggc gtg ccg gat cgt ttt agc      192
Ile Tyr Ser Asn Asn Lys Arg Pro Ser Gly Val Pro Asp Arg Phe Ser
    50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                  70                  75                  80

agc gaa gac gaa gcg gat tat tat tgc cag tct tgg gat cct cgt tct      288
Ser Glu Asp Glu Ala Asp Tyr Tyr Cys Gln Ser Trp Asp Pro Arg Ser
                85                  90                  95

ttt act gtg ttt ggc ggc ggc acg aag tta acc gtt ctt ggc cag          333
Phe Thr Val Phe Gly Gly Gly Thr Lys Leu Thr Val Leu Gly Gln
            100                 105                 110
```

<210> SEQ ID NO 54
<211> LENGTH: 111
<212> TYPE: PRT
<213> ORGANISM: human

<400> SEQUENCE: 54

```
Asp Ile Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
            20                  25                  30

Thr Val Arg Trp Tyr Gln Gln Leu Pro Gly Thr Ala Pro Lys Leu Leu
        35                  40                  45

Ile Tyr Ser Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Ser Trp Asp Pro Arg Ser
                85                  90                  95

Phe Thr Val Phe Gly Gly Gly Thr Lys Leu Thr Val Leu Gly Gln
            100                 105                 110
```

<210> SEQ ID NO 55
<211> LENGTH: 330
<212> TYPE: DNA
<213> ORGANISM: human

-continued

```
<220> FEATURE:
<221> NAME/KEY: CDS
<222> LOCATION: (1)..(330)
<223> OTHER INFORMATION: Antibody-VL Region; MOR03069

<400> SEQUENCE: 55

gat atc gtg ctg acc cag ccg cct tca gtg agt ggc gca cca ggt cag       48
Asp Ile Val Leu Thr Gln Pro Pro Ser Val Ser Gly Ala Pro Gly Gln
  1               5                  10                  15

cgt gtg acc atc tcg tgt agc ggc agc agc agc aac att ggt tct aat       96
Arg Val Thr Ile Ser Cys Ser Gly Ser Ser Ser Asn Ile Gly Ser Asn
             20                  25                  30

act gtg cgt tgg tac cag cag ttg ccc ggg acg gcg ccg aaa ctt ctg      144
Thr Val Arg Trp Tyr Gln Gln Leu Pro Gly Thr Ala Pro Lys Leu Leu
         35                  40                  45

att tat tct aat aat aag cgt ccc tca ggc gtg ccg gat cgt ttt agc      192
Ile Tyr Ser Asn Asn Lys Arg Pro Ser Gly Val Pro Asp Arg Phe Ser
     50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                  70                  75                  80

agc gaa gac gaa gcg gat tat tat tgc tgg act ggt atg tct tat cat      288
Ser Glu Asp Glu Ala Asp Tyr Tyr Cys Trp Thr Gly Met Ser Tyr His
                 85                  90                  95

ttt gtg ttt ggc ggc ggc acg aag tta acc gtt ctt ggc cag              330
Phe Val Phe Gly Gly Gly Thr Lys Leu Thr Val Leu Gly Gln
            100                 105                 110


<210> SEQ ID NO 56
<211> LENGTH: 110
<212> TYPE: PRT
<213> ORGANISM: human

<400> SEQUENCE: 56

Asp Ile Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
             20                  25                  30

Thr Val Arg Trp Tyr Gln Gln Leu Pro Gly Thr Ala Pro Lys Leu Leu
         35                  40                  45

Ile Tyr Ser Asn Asn Lys Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Trp Thr Gly Met Ser Tyr His
                 85                  90                  95

Phe Val Phe Gly Gly Gly Thr Lys Leu Thr Val Leu Gly Gln
            100                 105                 110


<210> SEQ ID NO 57
<211> LENGTH: 333
<212> TYPE: DNA
<213> ORGANISM: human
<220> FEATURE:
<221> NAME/KEY: CDS
<222> LOCATION: (1)..(333)
<223> OTHER INFORMATION: Antibody-VL Region; MOR03071

<400> SEQUENCE: 57

gat atc gtg ctg acc cag ccg cct tca gtg agt ggc gca cca ggt cag       48
Asp Ile Val Leu Thr Gln Pro Pro Ser Val Ser Gly Ala Pro Gly Gln
  1               5                  10                  15
```

-continued

```
cgt gtg acc atc tcg tgt agc ggc agc agc agc aac att ggt tct aat       96
Arg Val Thr Ile Ser Cys Ser Gly Ser Ser Ser Asn Ile Gly Ser Asn
            20                  25                  30

act gtg cgt tgg tac cag cag ttg ccc ggg acg gcg ccg aaa ctt ctg      144
Thr Val Arg Trp Tyr Gln Gln Leu Pro Gly Thr Ala Pro Lys Leu Leu
        35                  40                  45

att tat tct aat aat aag cgt ccc tca ggc gtg ccg gat cgt ttt agc      192
Ile Tyr Ser Asn Asn Lys Arg Pro Ser Gly Val Pro Asp Arg Phe Ser
    50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
65                  70                  75                  80

agc gaa gac gaa gcg gat tat tat tgc ctt gct tat att cag tct aag      288
Ser Glu Asp Glu Ala Asp Tyr Tyr Cys Leu Ala Tyr Ile Gln Ser Lys
                85                  90                  95

ggt cat gtg ttt ggc ggc ggc acg aag tta acc gtt ctt ggc cag          333
Gly His Val Phe Gly Gly Gly Thr Lys Leu Thr Val Leu Gly Gln
            100                 105                 110


<210> SEQ ID NO 58
<211> LENGTH: 111
<212> TYPE: PRT
<213> ORGANISM: human

<400> SEQUENCE: 58

Asp Ile Val Leu Thr Gln Pro Pro Ser Val Ser Gly Ala Pro Gly Gln
1               5                   10                  15

Arg Val Thr Ile Ser Cys Ser Gly Ser Ser Ser Asn Ile Gly Ser Asn
            20                  25                  30

Thr Val Arg Trp Tyr Gln Gln Leu Pro Gly Thr Ala Pro Lys Leu Leu
        35                  40                  45

Ile Tyr Ser Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
65                  70                  75                  80

Ser Glu Asp Glu Ala Asp Tyr Tyr Cys Leu Ala Tyr Ile Gln Ser Lys
                85                  90                  95

Gly His Val Phe Gly Gly Gly Thr Lys Leu Thr Val Leu Gly Gln
            100                 105                 110


<210> SEQ ID NO 59
<211> LENGTH: 339
<212> TYPE: DNA
<213> ORGANISM: human
<220> FEATURE:
<221> NAME/KEY: CDS
<222> LOCATION: (1)..(339)
<223> OTHER INFORMATION: Antibody-VL Region; MOR03064

<400> SEQUENCE: 59

gat atc gca ctg acc cag cca gct tca gtg agc ggc tca cca ggt cag       48
Asp Ile Ala Leu Thr Gln Pro Ala Ser Val Ser Gly Ser Pro Gly Gln
1               5                   10                  15

agc att acc atc tcg tgt acg ggt act agc agc gat ggt ggt ggt tat       96
Ser Ile Thr Ile Ser Cys Thr Gly Thr Ser Ser Asp Gly Gly Gly Tyr
            20                  25                  30

aat act gtg tct tgg tac cag cag cat ccc ggg aag gcg ccg aaa ctt      144
Asn Thr Val Ser Trp Tyr Gln Gln His Pro Gly Lys Ala Pro Lys Leu
        35                  40                  45

atg att tat tat gtt cat aag cgt ccc tca ggc gtg agc aac cgt ttt      192
```

-continued

```
Met Ile Tyr Tyr Val His Lys Arg Pro Ser Gly Val Ser Asn Arg Phe
     50                  55                  60

agc gga tcc aaa agc ggc aac acc gcg agc ctg acc att agc ggc ctg      240
Ser Gly Ser Lys Ser Gly Asn Thr Ala Ser Leu Thr Ile Ser Gly Leu
 65                  70                  75                  80

caa gcg gaa gac gaa gcg gat tat tat tgc cag tct tgg gat ctt ctt      288
Gln Ala Glu Asp Glu Ala Asp Tyr Tyr Cys Gln Ser Trp Asp Leu Leu
                 85                  90                  95

gct cct tct gtt gtg ttt ggc ggc ggc acg aag tta acc gtt ctt ggc      336
Ala Pro Ser Val Val Phe Gly Gly Gly Thr Lys Leu Thr Val Leu Gly
            100                 105                 110

cag                                                                  339
Gln


<210> SEQ ID NO 60
<211> LENGTH: 113
<212> TYPE: PRT
<213> ORGANISM: human

<400> SEQUENCE: 60

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Gly Gly Gly Tyr
             20                  25                  30

Asn Thr Val Ser Trp Tyr Gln Gln His Pro Gly Lys Ala Pro Lys Leu
         35                  40                  45

Met Ile Tyr Tyr Val His Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Trp Asp Leu Leu
                 85                  90                  95

Ala Pro Ser Val Val Phe Gly Gly Gly Thr Lys Leu Thr Val Leu Gly
            100                 105                 110

Gln


<210> SEQ ID NO 61
<211> LENGTH: 339
<212> TYPE: DNA
<213> ORGANISM: human
<220> FEATURE:
<221> NAME/KEY: CDS
<222> LOCATION: (1)..(339)
<223> OTHER INFORMATION: Antibody-VL Region; MOR03062

<400> SEQUENCE: 61

gat atc gca ctg acc cag cca gct tca gtg agc ggc tca cca ggt cag       48
Asp Ile Ala Leu Thr Gln Pro Ala Ser Val Ser Gly Ser Pro Gly Gln
  1               5                  10                  15

agc att acc atc tcg tgt acg ggt act agc agc gat ggt ggt ggt tat       96
Ser Ile Thr Ile Ser Cys Thr Gly Thr Ser Ser Asp Gly Gly Gly Tyr
             20                  25                  30

aat act gtg tct tgg tac cag cag cat ccc ggg aag gcg ccg aaa ctt      144
Asn Thr Val Ser Trp Tyr Gln Gln His Pro Gly Lys Ala Pro Lys Leu
         35                  40                  45

atg att tat tat gtt cat aag cgt ccc tca ggc gtg agc aac cgt ttt      192
Met Ile Tyr Tyr Val His Lys Arg Pro Ser Gly Val Ser Asn Arg Phe
     50                  55                  60

agc gga tcc aaa agc ggc aac acc gcg agc ctg acc att agc ggc ctg      240
Ser Gly Ser Lys Ser Gly Asn Thr Ala Ser Leu Thr Ile Ser Gly Leu
```

-continued

```
 65                  70                  75                  80

caa gcg gaa gac gaa gcg gat tat tat tgc cag tct tgg gat ctt tct      288
Gln Ala Glu Asp Glu Ala Asp Tyr Tyr Cys Gln Ser Trp Asp Leu Ser
                 85                  90                  95

gtt cat cag gtt gtg ttt ggc ggc ggc acg aag tta acc gtt ctt ggc      336
Val His Gln Val Val Phe Gly Gly Gly Thr Lys Leu Thr Val Leu Gly
            100                 105                 110

cag                                                                  339
Gln


<210> SEQ ID NO 62
<211> LENGTH: 113
<212> TYPE: PRT
<213> ORGANISM: human

<400> SEQUENCE: 62

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Gly Gly Gly Tyr
             20                  25                  30

Asn Thr Val Ser Trp Tyr Gln Gln His Pro Gly Lys Ala Pro Lys Leu
         35                  40                  45

Met Ile Tyr Tyr Val His Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Trp Asp Leu Ser
                 85                  90                  95

Val His Gln Val Val Phe Gly Gly Gly Thr Lys Leu Thr Val Leu Gly
            100                 105                 110

Gln


<210> SEQ ID NO 63
<211> LENGTH: 336
<212> TYPE: DNA
<213> ORGANISM: human
<220> FEATURE:
<221> NAME/KEY: CDS
<222> LOCATION: (1)..(336)
<223> OTHER INFORMATION: Derivative of MOR03055: Antibody-VH Region;
      MOR03243

<400> SEQUENCE: 63

cag gtg caa ttg caa gaa agt ggt ccg ggc ctg gtg aaa ccg ggc gaa       48
Gln Val Gln Leu Gln Glu Ser Gly Pro Gly Leu Val Lys Pro Gly Glu
  1               5                  10                  15

acc ctg agc ctg acc tgc acc gtt tcc gga ggc agc att tct tct tat       96
Thr Leu Ser Leu Thr Cys Thr Val Ser Gly Gly Ser Ile Ser Ser Tyr
             20                  25                  30

tat tgg tct tgg att cgc cag gcc cct ggg aag ggt ctc gag tgg att      144
Tyr Trp Ser Trp Ile Arg Gln Ala Pro Gly Lys Gly Leu Glu Trp Ile
         35                  40                  45

ggc gag att cat cgt ggt ggt tat act cag tat aat cct tct ctt aag      192
Gly Glu Ile His Arg Gly Gly Tyr Thr Gln Tyr Asn Pro Ser Leu Lys
     50                  55                  60

tct cgg gtc acc att agc gtt gat act tcg aaa aac cag ttt agc ctg      240
Ser Arg Val Thr Ile Ser Val Asp Thr Ser Lys Asn Gln Phe Ser Leu
 65                  70                  75                  80

aaa ctg agc agc gtg acg gcg gcg gat acg gcc gtg tat tat tgc gcg      288
Lys Leu Ser Ser Val Thr Ala Ala Asp Thr Ala Val Tyr Tyr Cys Ala
```

-continued

```
                85                  90                  95

cgt ttt ttt gat gtt tgg ggc caa ggc acc ctg gtg acg gtt agc tca       336
Arg Phe Phe Asp Val Trp Gly Gln Gly Thr Leu Val Thr Val Ser Ser
            100                 105                 110


<210> SEQ ID NO 64
<211> LENGTH: 112
<212> TYPE: PRT
<213> ORGANISM: human

<400> SEQUENCE: 64

Gln Val Gln Leu Gln Glu Ser Gly Pro Gly Leu Val Lys Pro Gly Glu
  1               5                  10                  15

Thr Leu Ser Leu Thr Cys Thr Val Ser Gly Gly Ser Ile Ser Ser Tyr
            20                  25                  30

Tyr Trp Ser Trp Ile Arg Gln Ala Pro Gly Lys Gly Leu Glu Trp Ile
        35                  40                  45

Gly Glu Ile His Arg Gly Gly Tyr Thr Gln Tyr Asn Pro Ser Leu Lys
     50                  55                  60

Ser Arg Val Thr Ile Ser Val Asp Thr Ser Lys Asn Gln Phe Ser Leu
 65                  70                  75                  80

Lys Leu Ser Ser Val Thr Ala Ala Asp Thr Ala Val Tyr Tyr Cys Ala
                85                  90                  95

Arg Phe Phe Asp Val Trp Gly Gln Gly Thr Leu Val Thr Val Ser Ser
            100                 105                 110


<210> SEQ ID NO 65
<211> LENGTH: 336
<212> TYPE: DNA
<213> ORGANISM: human
<220> FEATURE:
<221> NAME/KEY: CDS
<222> LOCATION: (1)..(336)
<223> OTHER INFORMATION: Derivative of MOR03055: Antibody-VL Region;
      MOR03243

<400> SEQUENCE: 65

gat atc gtg ctg acc cag ccg cct tca gtg agt ggc gca cca ggt cag        48
Asp Ile Val Leu Thr Gln Pro Pro Ser Val Ser Gly Ala Pro Gly Gln
  1               5                  10                  15

cgt gtg acc atc tcg tgt agc ggc agc agc agc aac att ggt tct aat        96
Arg Val Thr Ile Ser Cys Ser Gly Ser Ser Ser Asn Ile Gly Ser Asn
            20                  25                  30

act gtg cgt tgg tac cag cag ttg ccc ggg acg gcg ccg aaa ctt ctg       144
Thr Val Arg Trp Tyr Gln Gln Leu Pro Gly Thr Ala Pro Lys Leu Leu
        35                  40                  45

att tat tct aat aat aag cgt ccc tca ggc gtg ccg gat cgt ttt agc       192
Ile Tyr Ser Asn Asn Lys Arg Pro Ser Gly Val Pro Asp Arg Phe Ser
     50                  55                  60

gga tcc aaa agc ggc acc agc gcg agc ctt gcg att acg ggc ctg caa       240
Gly Ser Lys Ser Gly Thr Ser Ala Ser Leu Ala Ile Thr Gly Leu Gln
 65                  70                  75                  80

agc gaa gac gaa gcg gat tat tat tgc cag gct tgg act cgt gct cat       288
Ser Glu Asp Glu Ala Asp Tyr Tyr Cys Gln Ala Trp Thr Arg Ala His
                85                  90                  95

cgt tat cct gtg ttt ggc ggc ggc acg aag tta acc gtt ctt ggc cag       336
Arg Tyr Pro Val Phe Gly Gly Gly Thr Lys Leu Thr Val Leu Gly Gln
            100                 105                 110


<210> SEQ ID NO 66
<211> LENGTH: 112
```

-continued

<212> TYPE: PRT
<213> ORGANISM: human

<400> SEQUENCE: 66

```
Asp Ile Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
             20                  25                  30

Thr Val Arg Trp Tyr Gln Gln Leu Pro Gly Thr Ala Pro Lys Leu Leu
         35                  40                  45

Ile Tyr Ser Asn Asn Lys Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Ala Trp Thr Arg Ala His
                 85                  90                  95

Arg Tyr Pro Val Phe Gly Gly Gly Thr Lys Leu Thr Val Leu Gly Gln
            100                 105                 110
```

<210> SEQ ID NO 67
<211> LENGTH: 336
<212> TYPE: DNA
<213> ORGANISM: human
<220> FEATURE:
<221> NAME/KEY: CDS
<222> LOCATION: (1)..(336)
<223> OTHER INFORMATION: Derivative of MOR03069; Antibody-VH Region; MOR03245

<400> SEQUENCE: 67

```
cag gtg caa ttg caa gaa agt ggt ccg ggc ctg gtg aaa ccg ggc gaa       48
Gln Val Gln Leu Gln Glu Ser Gly Pro Gly Leu Val Lys Pro Gly Glu
  1               5                  10                  15

acc ctg agc ctg acc tgc acc gtt tcc gga ggc agc att tct tct tat       96
Thr Leu Ser Leu Thr Cys Thr Val Ser Gly Gly Ser Ile Ser Ser Tyr
             20                  25                  30

tat tgg tct tgg att cgc cag gcc cct ggg aag ggt ctc gag tgg att      144
Tyr Trp Ser Trp Ile Arg Gln Ala Pro Gly Lys Gly Leu Glu Trp Ile
         35                  40                  45

ggc gtt att cat aag tgg ggt ttt act aat tat aat cct tct ctt aag      192
Gly Val Ile His Lys Trp Gly Phe Thr Asn Tyr Asn Pro Ser Leu Lys
     50                  55                  60

tct cgg gtc acc att agc gtt gat act tcg aaa aac cag ttt agc ctg      240
Ser Arg Val Thr Ile Ser Val Asp Thr Ser Lys Asn Gln Phe Ser Leu
 65                  70                  75                  80

aaa ctg agc agc gtg acg gcg gcg gat acg gcc gtg tat tat tgc gcg      288
Lys Leu Ser Ser Val Thr Ala Ala Asp Thr Ala Val Tyr Tyr Cys Ala
                 85                  90                  95

cgt ttt ttt gat gtt tgg ggc caa ggc acc ctg gtg acg gtt agc tca      336
Arg Phe Phe Asp Val Trp Gly Gln Gly Thr Leu Val Thr Val Ser Ser
            100                 105                 110
```

<210> SEQ ID NO 68
<211> LENGTH: 112
<212> TYPE: PRT
<213> ORGANISM: human

<400> SEQUENCE: 68

```
Gln Val Gln Leu Gln Glu Ser Gly Pro Gly Leu Val Lys Pro Gly Glu
  1               5                  10                  15

Thr Leu Ser Leu Thr Cys Thr Val Ser Gly Gly Ser Ile Ser Ser Tyr
```

-continued

```
            20                  25                  30

Tyr Trp Ser Trp Ile Arg Gln Ala Pro Gly Lys Gly Leu Glu Trp Ile
        35                  40                  45

Gly Val Ile His Lys Trp Gly Phe Thr Asn Tyr Asn Pro Ser Leu Lys
    50                  55                  60

Ser Arg Val Thr Ile Ser Val Asp Thr Ser Lys Asn Gln Phe Ser Leu
 65                 70                  75                  80

Lys Leu Ser Ser Val Thr Ala Ala Asp Thr Ala Val Tyr Tyr Cys Ala
                85                  90                  95

Arg Phe Phe Asp Val Trp Gly Gln Gly Thr Leu Val Thr Val Ser Ser
            100                 105                 110


<210> SEQ ID NO 69
<211> LENGTH: 330
<212> TYPE: DNA
<213> ORGANISM: human
<220> FEATURE:
<221> NAME/KEY: CDS
<222> LOCATION: (1)..(330)
<223> OTHER INFORMATION: Derivative of MOR03069; Antibody-VL Region;
      MOR03245

<400> SEQUENCE: 69

gat atc gtg ctg acc cag ccg cct tca gtg agt ggc gca cca ggt cag       48
Asp Ile Val Leu Thr Gln Pro Pro Ser Val Ser Gly Ala Pro Gly Gln
  1               5                  10                  15

cgt gtg acc atc tcg tgt agc ggc agc agc agc aac att ggt tct aat       96
Arg Val Thr Ile Ser Cys Ser Gly Ser Ser Ser Asn Ile Gly Ser Asn
            20                  25                  30

act gtg cgt tgg tac cag cag ttg ccc ggg acg gcg ccg aaa ctt ctg      144
Thr Val Arg Trp Tyr Gln Gln Leu Pro Gly Thr Ala Pro Lys Leu Leu
        35                  40                  45

att tat tct aat aat aag cgt ccc tca ggc gtg ccg gat cgt ttt agc      192
Ile Tyr Ser Asn Asn Lys Arg Pro Ser Gly Val Pro Asp Arg Phe Ser
    50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                 70                  75                  80

agc gaa gac gaa gcg gat tat tat tgc tgg act ggt atg tct tat cat      288
Ser Glu Asp Glu Ala Asp Tyr Tyr Cys Trp Thr Gly Met Ser Tyr His
                85                  90                  95

ttt gtg ttt ggc ggc ggc acg aag tta acc gtt ctt ggc cag              330
Phe Val Phe Gly Gly Gly Thr Lys Leu Thr Val Leu Gly Gln
            100                 105                 110


<210> SEQ ID NO 70
<211> LENGTH: 110
<212> TYPE: PRT
<213> ORGANISM: human

<400> SEQUENCE: 70

Asp Ile Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
            20                  25                  30

Thr Val Arg Trp Tyr Gln Gln Leu Pro Gly Thr Ala Pro Lys Leu Leu
        35                  40                  45

Ile Tyr Ser Asn Asn Lys Arg Pro Ser Gly Val Pro Asp Arg Phe Ser
    50                  55                  60

Gly Ser Lys Ser Gly Thr Ser Ala Ser Leu Ala Ile Thr Gly Leu Gln
```

-continued

```
 65                  70                  75                  80

Ser Glu Asp Glu Ala Asp Tyr Tyr Cys Trp Thr Gly Met Ser Tyr His
                85                  90                  95

Phe Val Phe Gly Gly Gly Thr Lys Leu Thr Val Leu Gly Gln
            100                 105                 110


<210> SEQ ID NO 71
<211> LENGTH: 354
<212> TYPE: DNA
<213> ORGANISM: human
<220> FEATURE:
<221> NAME/KEY: CDS
<222> LOCATION: (1)..(354)
<223> OTHER INFORMATION: Derivative of MOR03075; Antibody-VH Region;
      MOR03246

<400> SEQUENCE: 71

cag gtg caa ttg gtt cag agc ggc gcg gaa gtg aaa aaa ccg ggc gcg       48
Gln Val Gln Leu Val Gln Ser Gly Ala Glu Val Lys Lys Pro Gly Ala
  1               5                  10                  15

agc gtg aaa gtg agc tgc aaa gcc tcc gga tat acc ttt act ggt ttt       96
Ser Val Lys Val Ser Cys Lys Ala Ser Gly Tyr Thr Phe Thr Gly Phe
            20                  25                  30

tat att aat tgg gtc cgc caa gcc cct ggg cag ggt ctc gag tgg atg      144
Tyr Ile Asn Trp Val Arg Gln Ala Pro Gly Gln Gly Leu Glu Trp Met
        35                  40                  45

ggc tgg atc aat ccg tat tct ggc aat acg cgt tac gcg cag aag ttt      192
Gly Trp Ile Asn Pro Tyr Ser Gly Asn Thr Arg Tyr Ala Gln Lys Phe
     50                  55                  60

cag ggc cgg gtg acc atg acc cgt gat acc agc att agc acc gcg tat      240
Gln Gly Arg Val Thr Met Thr Arg Asp Thr Ser Ile Ser Thr Ala Tyr
 65                  70                  75                  80

atg gaa ctg agc agc ctg cgt agc gaa gat acg gcc gtg tat tat tgc      288
Met Glu Leu Ser Ser Leu Arg Ser Glu Asp Thr Ala Val Tyr Tyr Cys
                85                  90                  95

gcg cgt tct cct gtt tat tat aag tat gat tat tgg ggc caa ggc acc      336
Ala Arg Ser Pro Val Tyr Tyr Lys Tyr Asp Tyr Trp Gly Gln Gly Thr
            100                 105                 110

ctg gtg acg gtt agc tca                                              354
Leu Val Thr Val Ser Ser
        115


<210> SEQ ID NO 72
<211> LENGTH: 118
<212> TYPE: PRT
<213> ORGANISM: human

<400> SEQUENCE: 72

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Phe
            20                  25                  30

Tyr Ile Asn Trp Val Arg Gln Ala Pro Gly Gln Gly Leu Glu Trp Met
        35                  40                  45

Gly Trp Ile Asn Pro Tyr Ser Gly Asn Thr Arg Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                85                  90                  95
```

-continued

```
Ala Arg Ser Pro Val Tyr Tyr Lys Tyr Asp Tyr Trp Gly Gln Gly Thr
            100                 105                 110

Leu Val Thr Val Ser Ser
        115


<210> SEQ ID NO 73
<211> LENGTH: 333
<212> TYPE: DNA
<213> ORGANISM: human
<220> FEATURE:
<221> NAME/KEY: CDS
<222> LOCATION: (1)..(333)
<223> OTHER INFORMATION: Derivative of MOR03075; Antibody-VL Region;
      MOR03246

<400> SEQUENCE: 73

gat atc gtg ctg acc cag ccg cct tca gtg agt ggc gca cca ggt cag       48
Asp Ile Val Leu Thr Gln Pro Pro Ser Val Ser Gly Ala Pro Gly Gln
  1               5                  10                  15

cgt gtg acc atc tcg tgt agc ggc agc agc agc aac att ggt tct aat       96
Arg Val Thr Ile Ser Cys Ser Gly Ser Ser Ser Asn Ile Gly Ser Asn
             20                  25                  30

act gtg cgt tgg tac cag cag ttg ccc ggg acg gcg ccg aaa ctt ctg      144
Thr Val Arg Trp Tyr Gln Gln Leu Pro Gly Thr Ala Pro Lys Leu Leu
         35                  40                  45

att tat tct aat aat aag cgt ccc tca ggc gtg ccg gat cgt ttt agc      192
Ile Tyr Ser Asn Asn Lys Arg Pro Ser Gly Val Pro Asp Arg Phe Ser
     50                  55                  60

gga tcc aaa agc ggc acc agc gcg agc ctt gcg att acg ggc ctg caa      240
Gly Ser Lys Ser Gly Thr Ser Ala Ser Leu Ala Ile Thr Gly Leu Gln
 65                  70                  75                  80

agc gaa gac gaa gcg gat tat tat tgc cag tct tgg gat cct cgt tct      288
Ser Glu Asp Glu Ala Asp Tyr Tyr Cys Gln Ser Trp Asp Pro Arg Ser
                 85                  90                  95

ttt act gtg ttt ggc ggc ggc acg aag tta acc gtt ctt ggc cag          333
Phe Thr Val Phe Gly Gly Gly Thr Lys Leu Thr Val Leu Gly Gln
            100                 105                 110


<210> SEQ ID NO 74
<211> LENGTH: 111
<212> TYPE: PRT
<213> ORGANISM: human

<400> SEQUENCE: 74

Asp Ile Val Leu Thr Gln Pro Pro Ser Val Ser Gly Ala Pro Gly Gln
  1               5                  10                  15

Arg Val Thr Ile Ser Cys Ser Gly Ser Ser Ser Asn Ile Gly Ser Asn
             20                  25                  30

Thr Val Arg Trp Tyr Gln Gln Leu Pro Gly Thr Ala Pro Lys Leu Leu
         35                  40                  45

Ile Tyr Ser Asn Asn Lys Arg Pro Ser Gly Val Pro Asp Arg Phe Ser
     50                  55                  60

Gly Ser Lys Ser Gly Thr Ser Ala Ser Leu Ala Ile Thr Gly Leu Gln
 65                  70                  75                  80

Ser Glu Asp Glu Ala Asp Tyr Tyr Cys Gln Ser Trp Asp Pro Arg Ser
                 85                  90                  95

Phe Thr Val Phe Gly Gly Gly Thr Lys Leu Thr Val Leu Gly Gln
            100                 105                 110


<210> SEQ ID NO 75
<211> LENGTH: 348
```

-continued

<212> TYPE: DNA
<213> ORGANISM: human
<220> FEATURE:
<221> NAME/KEY: CDS
<222> LOCATION: (1)..(348)
<223> OTHER INFORMATION: Derivative of MOR03062; Antibody-VH Region;
MOR03251

<400> SEQUENCE: 75

```
cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt tct tct tat       96
Ser Leu Arg Leu Ser Cys Ala Ala Ser Gly Phe Thr Phe Ser Ser Tyr
             20                  25                  30

ggt atg cat tgg gtg cgc caa gcc cct ggg aag ggt ctc gag tgg gtg      144
Gly Met His Trp Val Arg Gln Ala Pro Gly Lys Gly Leu Glu Trp Val
         35                  40                  45

agc gtt att tct aat atg tct tat act att tat tat gct gat tct gtt      192
Ser Val Ile Ser Asn Met Ser Tyr Thr Ile Tyr Tyr Ala Asp Ser Val
     50                  55                  60

aag ggt cgt ttt acc att tca cgt gat aat tcg aaa aac acc ctg tat      240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                 85                  90                  95

gcg cgt aat aag gtt ggt ttt gat gtt tgg ggc caa ggc acc ctg gtg      336
Ala Arg Asn Lys Val Gly Phe Asp Val Trp Gly Gln Gly Thr Leu Val
            100                 105                 110

acg gtt agc tca                                                      348
Thr Val Ser Ser
        115
```

<210> SEQ ID NO 76
<211> LENGTH: 116
<212> TYPE: PRT
<213> ORGANISM: human

<400> SEQUENCE: 76

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ser Val Ile Ser Asn Met Ser Tyr Thr Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Lys Val Gly Phe Asp Val Trp Gly Gln Gly Thr Leu Val
            100                 105                 110

Thr Val Ser Ser
        115
```

<210> SEQ ID NO 77
<211> LENGTH: 339
<212> TYPE: DNA
<213> ORGANISM: human

-continued

```
<220> FEATURE:
<221> NAME/KEY: CDS
<222> LOCATION: (1)..(339)
<223> OTHER INFORMATION: Derivative of MOR03062; Antibody-VL Region;
      MOR03251

<400> SEQUENCE: 77

gat atc gca ctg acc cag cca gct tca gtg agc ggc tca cca ggt cag       48
Asp Ile Ala Leu Thr Gln Pro Ala Ser Val Ser Gly Ser Pro Gly Gln
  1               5                  10                  15

agc att acc atc tcg tgt acg ggt act agc agc gat ggt ggt ggt tat       96
Ser Ile Thr Ile Ser Cys Thr Gly Thr Ser Ser Asp Gly Gly Gly Tyr
             20                  25                  30

aat act gtg tct tgg tac cag cag cat ccc ggg aag gcg ccg aaa ctt      144
Asn Thr Val Ser Trp Tyr Gln Gln His Pro Gly Lys Ala Pro Lys Leu
         35                  40                  45

atg att tat tat gtt cat aag cgt ccc tca ggc gtg agc aac cgt ttt      192
Met Ile Tyr Tyr Val His Lys Arg Pro Ser Gly Val Ser Asn Arg Phe
     50                  55                  60

agc gga tcc aaa agc ggc aac acc gcg agc ctg acc att agc ggc ctg      240
Ser Gly Ser Lys Ser Gly Asn Thr Ala Ser Leu Thr Ile Ser Gly Leu
 65                  70                  75                  80

caa gcg gaa gac gaa gcg gat tat tat tgc cag tct tgg gat ctt tct      288
Gln Ala Glu Asp Glu Ala Asp Tyr Tyr Cys Gln Ser Trp Asp Leu Ser
                 85                  90                  95

gtt cat cag gtt gtg ttt ggc ggc ggc acg aag tta acc gtt ctt ggc      336
Val His Gln Val Val Phe Gly Gly Gly Thr Lys Leu Thr Val Leu Gly
            100                 105                 110

cag                                                                  339
Gln


<210> SEQ ID NO 78
<211> LENGTH: 113
<212> TYPE: PRT
<213> ORGANISM: human

<400> SEQUENCE: 78

Asp Ile Ala Leu Thr Gln Pro Ala Ser Val Ser Gly Ser Pro Gly Gln
  1               5                  10                  15

Ser Ile Thr Ile Ser Cys Thr Gly Thr Ser Ser Asp Gly Gly Gly Tyr
             20                  25                  30

Asn Thr Val Ser Trp Tyr Gln Gln His Pro Gly Lys Ala Pro Lys Leu
         35                  40                  45

Met Ile Tyr Tyr Val His Lys Arg Pro Ser Gly Val Ser Asn Arg Phe
     50                  55                  60

Ser Gly Ser Lys Ser Gly Asn Thr Ala Ser Leu Thr Ile Ser Gly Leu
 65                  70                  75                  80

Gln Ala Glu Asp Glu Ala Asp Tyr Tyr Cys Gln Ser Trp Asp Leu Ser
                 85                  90                  95

Val His Gln Val Val Phe Gly Gly Gly Thr Lys Leu Thr Val Leu Gly
            100                 105                 110

Gln


<210> SEQ ID NO 79
<211> LENGTH: 348
<212> TYPE: DNA
<213> ORGANISM: human
<220> FEATURE:
<221> NAME/KEY: CDS
<222> LOCATION: (1)..(348)
<223> OTHER INFORMATION: Antibody-VH Region; MOR03252
```

-continued

<400> SEQUENCE: 79

```
cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt tct tct tat       96
Ser Leu Arg Leu Ser Cys Ala Ala Ser Gly Phe Thr Phe Ser Ser Tyr
             20                  25                  30

ggt atg cat tgg gtg cgc caa gcc cct ggg aag ggt ctc gag tgg gtg      144
Gly Met His Trp Val Arg Gln Ala Pro Gly Lys Gly Leu Glu Trp Val
         35                  40                  45

agc gtt att tct aat tat tct tgg cat att tat tat gct gat tct gtt      192
Ser Val Ile Ser Asn Tyr Ser Trp His Ile Tyr Tyr Ala Asp Ser Val
     50                  55                  60

aag ggt cgt ttt acc att tca cgt gat aat tcg aaa aac acc ctg tat      240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                 85                  90                  95

gcg cgt aat aag gtt ggt ttt gat gtt tgg ggc caa ggc acc ctg gtg      336
Ala Arg Asn Lys Val Gly Phe Asp Val Trp Gly Gln Gly Thr Leu Val
            100                 105                 110

acg gtt agc tca                                                      348
Thr Val Ser Ser
        115
```

<210> SEQ ID NO 80
<211> LENGTH: 116
<212> TYPE: PRT
<213> ORGANISM: human

<400> SEQUENCE: 80

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ser Val Ile Ser Asn Tyr Ser Trp His Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Lys Val Gly Phe Asp Val Trp Gly Gln Gly Thr Leu Val
            100                 105                 110

Thr Val Ser Ser
        115
```

<210> SEQ ID NO 81
<211> LENGTH: 348
<212> TYPE: DNA
<213> ORGANISM: human
<220> FEATURE:
<221> NAME/KEY: CDS
<222> LOCATION: (1)..(348)
<223> OTHER INFORMATION: Antibody-VH Region; MOR03253

<400> SEQUENCE: 81

-continued

```
cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt tct tct tat       96
Ser Leu Arg Leu Ser Cys Ala Ala Ser Gly Phe Thr Phe Ser Ser Tyr
             20                  25                  30

ggt atg cat tgg gtg cgc caa gcc cct ggg aag ggt ctc gag tgg gtg      144
Gly Met His Trp Val Arg Gln Ala Pro Gly Lys Gly Leu Glu Trp Val
         35                  40                  45

agc gtt att tct aat atg ggt ttt gag att tat tat gct gat tct gtt      192
Ser Val Ile Ser Asn Met Gly Phe Glu Ile Tyr Tyr Ala Asp Ser Val
     50                  55                  60

aag ggt cgt ttt acc att tca cgt gat aat tcg aaa aac acc ctg tat      240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                 85                  90                  95

gcg cgt aat aag gtt ggt ttt gat gtt tgg ggc caa ggc acc ctg gtg      336
Ala Arg Asn Lys Val Gly Phe Asp Val Trp Gly Gln Gly Thr Leu Val
            100                 105                 110

acg gtt agc tca                                                      348
Thr Val Ser Ser
        115
```

<210> SEQ ID NO 82
<211> LENGTH: 116
<212> TYPE: PRT
<213> ORGANISM: human

<400> SEQUENCE: 82

```
Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
             20                  25                  30

Gly Met His Trp Val Arg Gln Ala Pro Gly Lys Gly Leu Glu Trp Val
         35                  40                  45

Ser Val Ile Ser Asn Met Gly Phe Glu Ile Tyr Tyr Ala Asp Ser Val
     50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Asn Lys Val Gly Phe Asp Val Trp Gly Gln Gly Thr Leu Val
            100                 105                 110

Thr Val Ser Ser
        115
```

<210> SEQ ID NO 83
<211> LENGTH: 348
<212> TYPE: DNA
<213> ORGANISM: human
<220> FEATURE:
<221> NAME/KEY: CDS
<222> LOCATION: (1)..(348)
<223> OTHER INFORMATION: Antibody-VH Region; MOR03255

<400> SEQUENCE: 83

```
cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15
```

```
agc ctg cgt ctg agc tgc gcg gcc tcc gga ttt acc ttt tct tct tat        96
Ser Leu Arg Leu Ser Cys Ala Ala Ser Gly Phe Thr Phe Ser Ser Tyr
            20                  25                  30

ggt atg cat tgg gtg cgc caa gcc cct ggg aag ggt ctc gag tgg gtg       144
Gly Met His Trp Val Arg Gln Ala Pro Gly Lys Gly Leu Glu Trp Val
        35                  40                  45

agc gtt att tct aat cgt tct tct tat att tat tat gct gat tct gtt       192
Ser Val Ile Ser Asn Arg Ser Ser Tyr Ile Tyr Tyr Ala Asp Ser Val
    50                  55                  60

aag ggt cgt ttt acc att tca cgt gat aat tcg aaa aac acc ctg tat       240
Lys Gly Arg Phe Thr Ile Ser Arg Asp Asn Ser Lys Asn Thr Leu Tyr
 65                  70                  75                  80

ctg caa atg aac agc ctg cgt gcg gaa gat acg gcc gtg tat tat tgc       288
Leu Gln Met Asn Ser Leu Arg Ala Glu Asp Thr Ala Val Tyr Tyr Cys
                85                  90                  95

gcg cgt aat aag gtt ggt ttt gat gtt tgg ggc caa ggc acc ctg gtg       336
Ala Arg Asn Lys Val Gly Phe Asp Val Trp Gly Gln Gly Thr Leu Val
            100                 105                 110

acg gtt agc tca                                                       348
Thr Val Ser Ser
        115


<210> SEQ ID NO 84
<211> LENGTH: 116
<212> TYPE: PRT
<213> ORGANISM: human

<400> SEQUENCE: 84

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Ser Asn Arg Ser Ser Tyr Ile Tyr Tyr Ala Asp Ser Val
    50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Arg Asn Lys Val Gly Phe Asp Val Trp Gly Gln Gly Thr Leu Val
            100                 105                 110

Thr Val Ser Ser
        115


<210> SEQ ID NO 85
<211> LENGTH: 348
<212> TYPE: DNA
<213> ORGANISM: human
<220> FEATURE:
<221> NAME/KEY: CDS
<222> LOCATION: (1)..(348)
<223> OTHER INFORMATION: Antibody-VH Region; MOR03257

<400> SEQUENCE: 85

cag gtg caa ttg gtg gaa agc ggc ggc ggc ctg gtg caa ccg ggc ggc        48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt tct tct tat        96
Ser Leu Arg Leu Ser Cys Ala Ala Ser Gly Phe Thr Phe Ser Ser Tyr
```

-continued

```
            20                  25                  30

ggt atg cat tgg gtg cgc caa gcc cct ggg aag ggt ctc gag tgg gtg      144
Gly Met His Trp Val Arg Gln Ala Pro Gly Lys Gly Leu Glu Trp Val
        35                  40                  45

agc gtt att tct aat cgt ggt aat tat att tat tat gct gat tct gtt      192
Ser Val Ile Ser Asn Arg Gly Asn Tyr Ile Tyr Tyr Ala Asp Ser Val
    50                  55                  60

aag ggt cgt ttt acc att tca cgt gat aat tcg aaa aac acc ctg tat      240
Lys Gly Arg Phe Thr Ile Ser Arg Asp Asn Ser Lys Asn Thr Leu Tyr
 65                 70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                85                  90                  95

gcg cgt aat aag gtt ggt ttt gat gtt tgg ggc caa ggc acc ctg gtg      336
Ala Arg Asn Lys Val Gly Phe Asp Val Trp Gly Gln Gly Thr Leu Val
            100                 105                 110

acg gtt agc tca                                                      348
Thr Val Ser Ser
        115


<210> SEQ ID NO 86
<211> LENGTH: 116
<212> TYPE: PRT
<213> ORGANISM: human

<400> SEQUENCE: 86

Gln Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Ser Asn Arg Gly Asn Tyr Ile Tyr Tyr Ala Asp Ser Val
    50                  55                  60

Lys Gly Arg Phe Thr Ile Ser Arg Asp Asn Ser Lys Asn Thr Leu Tyr
 65                 70                  75                  80

Leu Gln Met Asn Ser Leu Arg Ala Glu Asp Thr Ala Val Tyr Tyr Cys
                85                  90                  95

Ala Arg Asn Lys Val Gly Phe Asp Val Trp Gly Gln Gly Thr Leu Val
            100                 105                 110

Thr Val Ser Ser
        115


<210> SEQ ID NO 87
<211> LENGTH: 348
<212> TYPE: DNA
<213> ORGANISM: human
<220> FEATURE:
<221> NAME/KEY: CDS
<222> LOCATION: (1)..(348)
<223> OTHER INFORMATION: Derivative of MOR03075; Antibody-VH Region;
      MOR03258

<400> SEQUENCE: 87

cag gtg caa ttg gtg gaa agc ggc ggc ggc ctg gtg caa ccg ggc ggc       48
Gln Val Gln Leu Val Glu Ser Gly Gly Gly Leu Val Gln Pro Gly Gly
  1               5                  10                  15

agc ctg cgt ctg agc tgc gcg gcc tcc gga ttt acc ttt tct tct tat       96
Ser Leu Arg Leu Ser Cys Ala Ala Ser Gly Phe Thr Phe Ser Ser Tyr
            20                  25                  30
```

-continued

```
ggt atg cat tgg gtg cgc caa gcc cct ggg aag ggt ctc gag tgg gtg      144
Gly Met His Trp Val Arg Gln Ala Pro Gly Lys Gly Leu Glu Trp Val
        35                  40                  45

agc gtt att tct aat cag tct aat tat att tat tat gct gat tct gtt      192
Ser Val Ile Ser Asn Gln Ser Asn Tyr Ile Tyr Tyr Ala Asp Ser Val
    50                  55                  60

aag ggt cgt ttt acc att tca cgt gat aat tcg aaa aac acc ctg tat      240
Lys Gly Arg Phe Thr Ile Ser Arg Asp Asn Ser Lys Asn Thr Leu Tyr
65                  70                  75                  80

ctg caa atg aac agc ctg cgt gcg gaa gat acg gcc gtg tat tat tgc      288
Leu Gln Met Asn Ser Leu Arg Ala Glu Asp Thr Ala Val Tyr Tyr Cys
                85                  90                  95

gcg cgt aat aag gtt ggt ttt gat gtt tgg ggc caa ggc acc ctg gtg      336
Ala Arg Asn Lys Val Gly Phe Asp Val Trp Gly Gln Gly Thr Leu Val
            100                 105                 110

acg gtt agc tca                                                      348
Thr Val Ser Ser
        115


<210> SEQ ID NO 88
<211> LENGTH: 116
<212> TYPE: PRT
<213> ORGANISM: human

<400> SEQUENCE: 88

Gln Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Gly Met His Trp Val Arg Gln Ala Pro Gly Lys Gly Leu Glu Trp Val
        35                  40                  45

Ser Val Ile Ser Asn Gln Ser Asn Tyr Ile Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Lys Val Gly Phe Asp Val Trp Gly Gln Gly Thr Leu Val
            100                 105                 110

Thr Val Ser Ser
        115


<210> SEQ ID NO 89
<211> LENGTH: 354
<212> TYPE: DNA
<213> ORGANISM: human
<220> FEATURE:
<221> NAME/KEY: CDS
<222> LOCATION: (1)..(354)
<223> OTHER INFORMATION: Derivative of MOR03075; Antibody-VL Region;
      MOR03258

<400> SEQUENCE: 89

cag gtg caa ttg gtt cag agc ggc gcg gaa gtg aaa aaa ccg ggc gcg       48
Gln Val Gln Leu Val Gln Ser Gly Ala Glu Val Lys Lys Pro Gly Ala
1               5                   10                  15

agc gtg aaa gtg agc tgc aaa gcc tcc gga tat acc ttt act ggt ttt       96
Ser Val Lys Val Ser Cys Lys Ala Ser Gly Tyr Thr Phe Thr Gly Phe
            20                  25                  30

tat att aat tgg gtc cgc caa gcc cct ggg cag ggt ctc gag tgg atg      144
Tyr Ile Asn Trp Val Arg Gln Ala Pro Gly Gln Gly Leu Glu Trp Met
```

-continued

```
        35                  40                  45

ggc tgg atc aat ccg tat tct ggc aat acg cgt tac gcg cag aag ttt      192
Gly Trp Ile Asn Pro Tyr Ser Gly Asn Thr Arg Tyr Ala Gln Lys Phe
     50                  55                  60

cag ggc cgg gtg acc atg acc cgt gat acc agc att agc acc gcg tat      240
Gln Gly Arg Val Thr Met Thr Arg Asp Thr Ser Ile Ser Thr Ala Tyr
 65                  70                  75                  80

atg gaa ctg agc agc ctg cgt agc gaa gat acg gcc gtg tat tat tgc      288
Met Glu Leu Ser Ser Leu Arg Ser Glu Asp Thr Ala Val Tyr Tyr Cys
                 85                  90                  95

gcg cgt tct cct gtt tat tat aag tat gat tat tgg ggc caa ggc acc      336
Ala Arg Ser Pro Val Tyr Tyr Lys Tyr Asp Tyr Trp Gly Gln Gly Thr
            100                 105                 110

ctg gtg acg gtt agc tca                                              354
Leu Val Thr Val Ser Ser
        115


<210> SEQ ID NO 90
<211> LENGTH: 118
<212> TYPE: PRT
<213> ORGANISM: human

<400> SEQUENCE: 90

Gln Val Gln Leu Val Gln Ser Gly Ala Glu Val Lys Lys Pro Gly Ala
  1               5                  10                  15

Ser Val Lys Val Ser Cys Lys Ala Ser Gly Tyr Thr Phe Thr Gly Phe
             20                  25                  30

Tyr Ile Asn Trp Val Arg Gln Ala Pro Gly Gln Gly Leu Glu Trp Met
        35                  40                  45

Gly Trp Ile Asn Pro Tyr Ser Gly Asn Thr Arg Tyr Ala Gln Lys Phe
     50                  55                  60

Gln Gly Arg Val Thr Met Thr Arg Asp Thr Ser Ile Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Ser Pro Val Tyr Tyr Lys Tyr Asp Tyr Trp Gly Gln Gly Thr
            100                 105                 110

Leu Val Thr Val Ser Ser
        115
```

IDENTIFICATION AND CHARACTERIZATION OF FUNCTION-BLOCKING ANTI-ED-B-FIBRONECTIN ANTIBODIES

This application claims the benefit of the filing date of U.S. Provisional Application Ser. No. 60/697,565 filed Jul. 11, 2005 which is incorporated by reference herein.

The invention relates to recombinant polypeptides, in particular antibodies or antibody fragments that bind to the ED-B-isoform of fibronectin and can block their function. In addition, the diagnostic and pharmaceutical application of the polypeptides according to the invention is disclosed.

During tumor development and progression, the extracellular matrix (ECM), in which the tumor grows, is modified by proteolytic degradation of already existing ECM. This process generates a tumor-induced matrix, which is distinguished from that of the ECM that occurs in normal tissue. The tumor-induced ECM appears to be the optimum environment for tumor growth and tumor angiogenesis (1-4).

In tumor angiogenesis, new blood vessels are formed from already existing vessels. This process requires the proteolysis of ECM, the targeted growth and differentiation of endothelial cells in new vascular structures, which are essential for further tumor growth (5).

Fibronectins are an important class of matrix-glycoproteins. Their main role consists in facilitating the adhesion of cells to a number of different extracellular matrices. The presence of fibronectins on the surface of non-transformed cells in culture as well as their absence in the case of transformed cells resulted in the identification of fibronectins as important adhesion proteins. They interact with numerous other different molecules, e.g., collagen, heparan sulfate-proteoglycans and fibrin, and thus regulate the cell shape and the creation of the cytoskeleton. In addition, they are responsible for cell migration and cell differentiation during embryogenesis. In addition, they are important for wound healing, in which they make possible the migration of macrophages and other immune cells in the field in question and in the formation of blood clots by making possible the adhesion of blood platelets to damaged regions of the blood vessels.

Fibronectins are dimers of two similar peptides, whereby each chain is approximately 60-70 nm long. At least 20 different fibronectin chains have been identified, of which all are produced by alternative splicing of the RNA transcript of a single fibronectin gene.

Fibronectins are high-molecular, adhesion-mediating glycoproteins that play an important role in the development of the vascular system. In addition, fibronectins act chemotactically on endothelial cells, modulate the action of growth factors and support the linear growth of endothelial cells during angiogenesis (6-9). An analysis of proteolytic fibronectin-cleavage products shows that the polypeptides consist of six heavily folded domains of which each domain in turn contains so-called repetition sequences ("repeats") whose similarities with respect to their amino acid sequence allow a classification in three types (types I, II, and III). The central region of both chains of the dimer consists of a section of so-called type-III repetitions, which on average are 90 amino acids long (10). Structural studies have revealed that each type-III repetition consists of seven beta-strands, which are folded into two antiparallel folded sheets, whereby short loop regions are exposed as potential protein-protein-interaction sites (11).

These type-III repetitions make it possible for fibronectins to act as adhesion molecules that interact with cell surface molecules, the so-called "integrins." The term "integrin" was used for the first time in 1987 in (12) to describe a related group of heterodimeric cell surface molecules that act as mediators between the extracellular matrix and the intracellular cytoskeleton and thus induce cell adhesion and migration. These heterodimeric receptors "integrate" or mediate signals from the extracellular environment with specific cellular functions. Up until now, 17 beta-subunits have been known that can interact specifically and non-covalently with more than 20 alpha-subunits, particularly to form as 20 different families (13). The sequence RGDS, which is found in the tenth repetition of type III of the fibronectin (III-10), in particular mediates the interaction of fibronectin with at least 8 different integrins. Moreover, it was shown that at least four integrins can interact specifically with fibronectin in an RGDS-independent way (13). In addition to the III7-, III8-, III9- and III10 sequences, the group of repetition sequences of type III also comprises the EIIIB and EIIIA (ED-B and ED-A) repetitions.

The ED-B-fibronectin cannot be detected in the normal tissue of adults (sole exception: proliferating endometrium), while it is strongly expressed in fetal tissue and in tumor growth, in addition to a stromal local expression of ED-B. Moreover, ED-B-fibronectin is localized perivascularly around blood vessels that have newly formed during the angiogenesis. For this reason, ED-B-fibronectin is a specific marker protein for the process of (tumor) angiogenesis (14).

The ED-B domain is a highly-conserved, complete type-III homology component that consists of 91 amino acids. The degree of homology between humans and rats is 100%, between humans and chickens 96%. In literature, very little is known on the function of the ED-B-domains. A few publications (15-17) speculate on a general adhesion-mediating action for various cells. A specific action on endothelial cells was still not shown to date.

In WO 02/20563, it was shown that recombinant ED-B shows a specific pro-angiogenic action in vitro: (i) the proliferation of bFGF-stimulated human dermal microvascular endothelial cells (HDMVEc) is enhanced by recombinant ED-B, (ii) the protein mediates the adhesion of HDMVEC, and (iii) recombinant ED-B stimulates the invasion and differentiation (tube formation) of HDMVEc in collagen gels.

In addition, these ED-B-mediated effects could be specifically blocked by synthetic peptides that were derived from the ED-B domains. The peptide sequences thus represent the binding region for an ED-B-specific receptor on the endothelial cell surface that was identified by means of affinity chromatography as the $\alpha_2\beta_1$-integrin. The specific interaction between the $\alpha_2\beta_1$-integrin and the ED-B domain was not previously described in the literature.

Also disclosed in WO 02/20563 are proteins that are regulated specifically by the ED-B-fibronectin domain, which comprises the $\alpha_2\beta_1$-integrin, the focal adhesion kinase, the CD6 ligand (ALCAM), the alpha chain of the vitronectin receptor, the integrated alpha-8 subunit or the precursor of the follistatin-related protein.

A number of integrin receptors with partially overlapping properties are expressed by endothelial cells (lit.: D. G. Stupack and D. A. Cheresh, SciSTKE, 2002 Feb. 12, 2002). These expression patterns show that different integrins (e.g., alphavbeta3 and alpha5beta1) mediate similar biological phenomena (adhesion, migration and survival) and therefore represent redundant systems for the endothelial cells that safeguard their behavior and survival. It was previously known that alpha2beta1 interacts with its natural ligands, the collagens. The blocking of this interaction can result in an anti-angiogenic action (Y. Funahashi et al. Cancer Res. 62: 6116-6123, 2002).

One object of this invention was therefore the preparation of function-blocking binding molecules, such as, e.g., antibodies that specifically block receptor binding sites of the ED-B-domains. These binding molecules have an anti-angiogenic action on (tumor) endothelial cells. In contrast to relatively broadly expressed $\alpha_2\beta_1$-integrin, the ED-B domain represents an ideal and specific target molecule for such binding molecules.

The structure of ED-B makes the development of monoclonal and polyclonal antibodies difficult since it thus can be expected that ED-B has a low immunogenicity in vivo. The antibody BC-1 (J. Cell Biol. 108 (1989), 1139-1148) thus reacts with a cryptic epitope of fibronectin, which is present only in the presence of ED-B and therefore not directly with ED-B. Antibody L19 (Tarli et al. Blood 94 (1999), 192-198 and WO 01/62800), which was produced by use of recombinant ED-B as an immunogen, is in turn biologically inactive, i.e., it cannot recognize cell adhesion to ED-B to a significant extent.

Surprisingly enough, it was now found that function-blocking ED-B-binding molecules can be produced, such as, for example, the ED-B-function-blocking antibody MOR03255, which greatly inhibit the adhesion of cells to ED-B and bring about in vivo a significant reduction of the tumor growth. The blocking of ED-B produced by the binding molecules according to the invention obviously cannot be compensated for by compensatory mechanisms of collagen-integrin.

By means of the HuCAL®-GOLD antibody library—a library with, for example, 1.6×10E10 different antibodies in the Fab-fragment format, which was generated starting from the HuCAL-consensus sequences (WO 97/08320; Knappik, A.; Ge, L.; Honegger, A.; Pack, P.; Fischer, M.; Wellnhofer, G.; Hoess, A.; Wolle, J.; Plunckthun, A. and Virnekas, B. (2000) J. Mol. Biol. 296:57-86) by diversification corresponding to the diversity of human antibodies in all six CDR areas and is closely examined by means of CysDisplay (WO 01/05950) of a variant of the phage display process—function-blocking Fab-antibody fragments that bind selectively to the ED-B-domain were identified in the tests leading to this invention. The effectiveness of these antibody fragments could be shown in an in vitro adhesion test that reflects the specific interaction between recombinant ED-B and isolated HDMVEc. The binding affinity to the ED-B-domain could be considerably improved by a specific change in the binding molecules. It was also possible to show in vivo that the binding molecules in an animal model inhibit the growth of tumors.

A first aspect of the invention is thus a polypeptide that (i) specifically binds to the ED-B-domain of fibronectin and (ii) inhibits the interaction between the ED-B domain and its receptor.

The polypeptide according to the invention is preferably an antibody or antibody fragment. The term “antibody” in terms of this invention comprises polyclonal, monoclonal, chimera, humanized or human antibodies as well as recombinant antibodies, e.g., single-chain antibodies, or antigen-binding antibody fragments, e.g., monovalent antibody fragments, such as, for example, Fab fragments or scFv fragments, or divalent antibody fragments, such as, for example, $F(ab')_2$ fragments.

In this connection, it is essential to the invention that the antibodies contain one or more antigen binding sites that meet the above-mentioned requirements, i.e., specific binding to the ED-B domain and inhibition of the interaction between the ED-B domain and its receptor, especially its receptor on endothelial cells. These antigen binding properties are preferably achieved by combination of a VH and VL region, whereby these regions are built up from the thus-mentioned skeleton regions (FR1, FR2, FR3 and FR4) as well as the CDR regions that mediate the antigen bond (H-CDR1. H-CDR2, H-CDR3 for the VH region and L-CDR1, L-CDR2, L-CDR3 for the VL region).

The polypeptide according to the invention preferably has an affinity to the ED-B domain corresponding to a $K_D$ value of ≦1 µm, preferably ≦100 nM, especially preferably ≦10 nM, still more preferably ≦1 nM, and most preferably ≦0.1 nM, whereby the affinity can be determined as indicated in the examples by a test on the BIAcore® system.

The polypeptide according to the invention is distinguished in that it specifically binds to the ED-B domain of fibronectin, e.g., it binds with a significantly lower affinity to other fibronectin domains, in particular to fibronectin domain 6 (FN6) and/or fibronectin domains 7-8-9 (7-8-9). In a preferred embodiment, the polypeptide according to the invention and the fibronectin ED-B domain bind with an affinity that is higher by at least a factor of 2—in particular by at least a factor of 5, and especially preferably by at least a factor of 10—than that of FN6 and/or 7-8-9, as can be determined, for example, by the binding test that is indicated in the examples.

In another preferred embodiment, the polypeptide according to the invention shows in vitro an inhibition of the adhesion of recombinant ED-B to HDMVEc cells, preferably an inhibition of at least 50% and especially preferably of at least 75% in a concentration of 10 µg/ml in each case.

Moreover, it is preferred that the polypeptide according to the invention shows in vivo an inhibition of the growth of a tumor that is produced by implantation of F9-teratocarcinoma cells (ATCC CRL-1720) in test animals, for example hairless mice.

The polypeptide according to the invention is preferably selected from antibodies and antibody fragments that comprise (a) a VH region (i) Coded by a nucleic acid sequence SEQ ID NO. 1 (MOR 02610), SEQ ID NO. 5 (MOR 02611), SEQ ID NO. 9 (MOR 02613), SEQ ID NO. 13 (MOR 02614), SEQ ID NO. 17 (MOR 02616), SEQ ID NO. 21 (MOR 02618), SEQ ID NO. 25 (MOR 02619), SEQ ID NO. 29 (MOR 02622), SEQ ID NO. 33 (MOR 02715), SEQ ID NO. 37 (MOR 02718), SEQ ID NO. 41 (MOR 02721), SEQ ID NO. 45 (MOR 02722) or at least one H-CDR1-, H-CDR-2- and/or H-CDR3 region of one of the above-mentioned VH regions, or (ii) Derived from a VH region according to (i) by a change in at least one H-CDR region and/or (b) A VL region (i) Coded by a nucleic acid sequence SEQ ID NO. 3 (MOR 02610), SEQ ID NO. 7 (MOR 02611), SEQ ID NO. 11 (MOR 02613), SEQ ID NO. 15 (MOR 02614), SEQ ID NO. 19 (MOR 02616), SEQ ID NO. 23 (MOR 02618), SEQ ID NO. 27 (MOR 02619), SEQ ID NO. 31 (MOR 02622), SEQ ID NO. 35 (MOR 02715), SEQ ID NO. 39 (MOR 02718), SEQ ID NO. 43 (MOR 02721), SEQ ID NO. 47 (MOR 02722) or at least one L-CDR1-, L-CDR2- and/or L-CDR3-region of one of the above-mentioned VL regions or (ii) Derived from a VL region according to (i) by a change in at least one L-CDR region.

Changes in the L-CDR3 region in the VL region and/or changes of the H-CDR2 region in the VH region are preferred.

For example, the polypeptide according to the invention exhibits a VL region that is derived from the VL region and that is coded by the nucleic acid sequence SEQ ID NO. 27

(MOR 02619) or SEQ ID NO. 35 (MOR 02715). Especially preferred is a polypeptide that comprises a VH region (i) Coded by the nucleic acid sequence SEQ ID NO. 25 (MOR 02619) or SEQ ID NO. 33 (MOR 02715) or at least one H-CDR1, H-CDR-2 and/or H-CDR3 region of one of the above-mentioned VH regions, or (ii) Derived from a VH region according to (i) by a change in at least one H-CDR region.

The polypeptide preferably exhibits a VH region that is derived by a change in the H-CDR2 region and is coded by a VH region from the nucleic acid sequence SEQ ID NO. 25 (MOR 02619) or SEQ ID NO. 33 (MOR 02715). Especially preferred in this case is a polypeptide, comprising (a) A VH region (i) Coded by the nucleic acid sequence SEQ ID NO. 63 (MOR 03243), SEQ ID NO. 67 (MOR 03245), SEQ ID NO. 71 (MOR 03246), SEQ ID NO. 75 (MOR 03251), SEQ ID NO. 79 (MOR 03252), SEQ ID NO. 81 (MOR 03253), SEQ ID NO. 83 (MOR 03255), SEQ ID NO. 85 (MOR 03257), SEQ ID NO. 87 (MOR 03258) or at least the H-CDR2 region of one of the above-mentioned VH regions or (ii) Derived from a VH region according to (i) by a change in at least one H-CDR region and/or (b) a VL region (i) Coded by the nucleic acid sequence SEQ ID NO. 65 (MOR 03243), SEQ ID NO. 69 (MOR 03245), SEQ ID NO. 73 (MOR 03246), SEQ ID NO. 77 (MOR 03251 as well as MOR 03252, MOR 03253, MOR 03255 and MOR 03257), SEQ ID NO. 89 (MOR 03258) or at least the L-CDR1, L-CDR2 or L-CDR3 region of one of the above-mentioned VL regions, or (ii) Derived from a VL region according to (i) by a change in at least one L-CDR region.

Specific examples of the polypeptide according to the invention are as follows:

A polypeptide that comprises the VH region that is coded by SEQ ID NO. 1 and the VL region that is coded by SEQ ID NO. 3 (MOR 02610) or at least one H-CDR1, H-CDR2, H-CDR3, L-CDR1, L-CDR2, or L-CDR3 region thereof.

A polypeptide that comprises the VH region that is coded by SEQ ID NO. 5 and the VL region that is coded by SEQ ID NO. 7 (MOR 02611) or at least one H-CDR1, H-CDR2, H-CDR3, L-CDR1, L-CDR2, or L-CDR3 region thereof.

A polypeptide that comprises the VH region that is coded by SEQ ID NO. 9 and the VL region that is coded by SEQ ID NO. 11 (MOR 02613) or at least one H-CDR1, H-CDR2, H-CDR3, L-CDR1, L-CDR2, or L-CDR3 region thereof.

A polypeptide that comprises the VH region that is coded by SEQ ID NO. 13 and the VL region that is coded by SEQ ID NO. 15 (MOR 02614) or at least one H-CDR1, H-CDR2, H-CDR3, L-CDR1, L-CDR2, or L-CDR3 region thereof.

A polypeptide that comprises the VH region that is coded by SEQ ID NO. 17 and the VL region that is coded by SEQ ID NO. 19 (MOR 02616) or at least one H-CDR1, H-CDR2, H-CDR3, L-CDR1, L-CDR2, or L-CDR3 region thereof.

A polypeptide that comprises the VH region that is coded by SEQ ID NO. 21 and the VL region that is coded by SEQ ID NO. 23 (MOR 02618) or at least one H-CDR1, H-CDR2, H-CDR3, L-CDR1, L-CDR2, or L-CDR3 region thereof.

A polypeptide that comprises the VH region that is coded by SEQ ID NO. 25 and the VL region that is coded by SEQ ID NO. 27 (MOR 02619) or at least one H-CDR1, H-CDR2, H-CDR3, L-CDR1, L-CDR2, or L-CDR3 region thereof.

A polypeptide that comprises the VH region that is coded by SEQ ID NO. 29 and the VL region that is coded by SEQ ID NO. 31 (MOR 02622) or at least one H-CDR1, H-CDR2, H-CDR3, L-CDR1, L-CDR2, or L-CDR3 region thereof.

A polypeptide that comprises the VH region that is coded by SEQ ID NO. 33 and the VL region that is coded by SEQ ID NO. 35 (MOR 02715) or at least one H-CDR1, H-CDR2, H-CDR3, L-CDR1, L-CDR2, or L-CDR3 region thereof.

A polypeptide that comprises the VH region that is coded by SEQ ID NO. 37 and the VL region that is coded by SEQ ID NO. 39 (MOR 02718) or at least one H-CDR1, H-CDR2, H-CDR3, L-CDR1, L-CDR2, or L-CDR3 region thereof.

A polypeptide that comprises the VH region that is coded by SEQ ID NO. 41 and the VL region that is coded by SEQ ID NO. 43 (MOR 02721) or at least one H-CDR1, H-CDR2, H-CDR3, L-CDR1, L-CDR2, or L-CDR3 region thereof.

A polypeptide that comprises the VH region that is coded by SEQ ID NO. 45 and the VL region that is coded by SEQ ID NO. 47 (MOR 02722) or at least one H-CDR1, H-CDR2, H-CDR3, L-CDR1, L-CDR2, or L-CDR3 region thereof.

A polypeptide that comprises the VH region that is coded by SEQ ID NO. 25 and the VL region that is coded by SEQ ID NO. 49 (MOR 03055) or at least one H-CDR1, H-CDR2, H-CDR3, L-CDR1, L-CDR2, or L-CDR3 region thereof.

A polypeptide that comprises the VH region that is coded by SEQ ID NO. 25 and the VL region that is coded by SEQ ID NO. 51 (MOR 03066) or at least one H-CDR1, H-CDR2, H-CDR3, L-CDR1, L-CDR2, or L-CDR3 region thereof.

A polypeptide that comprises the VH region that is coded by SEQ ID NO. 25 and the VL region that is coded by SEQ ID NO. 53 (MOR 03075) or at least one H-CDR1, H-CDR2, H-CDR3, L-CDR1, L-CDR2, or L-CDR3 region thereof.

A polypeptide that comprises the VH region that is coded by SEQ ID NO. 25 and the VL region that is coded by SEQ ID NO. 55 (MOR 03069) or at least one H-CDR1, H-CDR2, H-CDR3, L-CDR1, L-CDR2, or L-CDR3 region thereof.

A polypeptide that comprises the VH region that is coded by SEQ ID NO. 25 and the VL region that is coded by SEQ ID NO. 57 (MOR 03071) or at least one H-CDR1, H-CDR2, H-CDR3, L-CDR1, L-CDR2, or L-CDR3 region thereof.

A polypeptide that comprises the VH region that is coded by SEQ ID NO. 33 and the VL region that is coded by SEQ ID NO. 59 (MOR 03064) or at least one H-CDR1, H-CDR2, H-CDR3, L-CDR1, L-CDR2, or L-CDR3 region thereof.

A polypeptide that comprises the VH region that is coded by SEQ ID NO. 33 and the VL region that is coded by SEQ ID NO. 61 (MOR 03062) or at least one H-CDR1, H-CDR2, H-CDR3, L-CDR1, L-CDR2, or L-CDR3 region thereof.

A polypeptide that comprises the VH region that is coded by SEQ ID NO. 63 and the VL region that is coded by SEQ ID NO. 65 (MOR 03243) or at least one H-CDR1, H-CDR2, H-CDR3, L-CDR1, L-CDR2, or L-CDR3 region thereof.

A polypeptide that comprises the VH region that is coded by SEQ ID NO. 67 and the VL region that is coded by SEQ ID NO. 69 (MOR 03245) or at least one H-CDR1, H-CDR2, H-CDR3, L-CDR1, L-CDR2, or L-CDR3 region thereof.

A polypeptide that comprises the VH region that is coded by SEQ ID NO. 71 and the VL region that is coded by SEQ ID NO. 73 (MOR 03246) or at least one H-CDR1, H-CDR2, H-CDR3, L-CDR1, L-CDR2 or L-CDR3 region thereof.

A polypeptide that comprises the VH region that is coded by SEQ ID NO. 75 and the VL region that is coded by SEQ ID NO. 77 (MOR 03251) or at least one H-CDR1, H-CDR2, H-CDR3, L-CDR1, L-CDR2, or L-CDR3 region thereof.

A polypeptide that comprises the VH region that is coded by SEQ ID NO. 79 and the VL region that is coded by SEQ ID NO. 77 (MOR 03252) or at least one H-CDR1, H-CDR2, H-CDR3, L-CDR 1, L-CDR2, or L-CDR3 region thereof.

A polypeptide that comprises the VH region that is coded by SEQ ID NO. 81 and the VL region that is coded by SEQ ID NO. 77 (MOR 03253) or at least one H-CDR1, H-CDR2, H-CDR3, L-CDR1, L-CDR2, or L-CDR3 region thereof.

A polypeptide that comprises the VH region that is coded by SEQ ID NO. 83 and the VR region that is coded by SEQ ID NO. 77 (MOR 03255) or at least one H-CDR1, H-CDR2, H-CDR3, L-CDR1, L-CDR2, or L-CDR3 region thereof.

A polypeptide that comprises the VH region that is coded by SEQ ID NO. 85 and the VR region that is coded by SEQ ID NO. 77 (MOR 03257) or at least one H-CDR1, H-CDR2, H-CDR3, L-CDR1, L-CDR2, or L-CDR3 region thereof.

A polypeptide that comprises the VH region that is coded by SEQ ID NO. 87 and the VR region that is coded by SEQ ID NO. 89 (MOR 03258) or at least one H-CDR1, H-CDR2, H-CDR3, L-CDR1, L-CDR2, or L-CDR3 region thereof.

The creation of the VH and VR chains of the polypeptides according to the invention is as follows:

VH Chain:

The 1-region framework extends from nt 1-78 (that is, 26 aa); the last codon (aa) of FR1 is always: TCC (Cys).

The "CDR1 region" can be of two different lengths, either 30 nt (10 aa) (possible in families VH1A, VH1B, 3, 4 and 5), or 36 nt (12 aa) (possible in families VH2, VH4 and VH6).

The 2-region framework always exhibits 33 nt (that is, 11 aa); the first codon (aa) of FR2 is always: TGG (Trp); the last two codons are always CTC.GAG (LeuGlu).

The "CDR2 region" can be of three different lengths; either 57 nt (19 aa) (possible in families VH2 and VH4), 60 nt (20 aa) (possible in families VH1A, VH1B, 3 and 5); or 63 nt (21 aa) (possible in family VH6).

The 3-region framework always exhibits 96 nt (that is, 32 aa); the third codon (aa) of FR3 is always: ACC (Thr); the last five codons are always TAT.TAT-.TGC.GCG.CGT (Tyr Tyr Cys Ala Arg).

The "CDR3 region" can be of several different lengths: from 12-69 nt (4-23 aa) (in all families VH2 and VH4), 60 nt (20 aa) (possible in families VH1A, VH1B, 3 and 5), or 63 nt (21 aa) (possible in family VH6).

The 4-region framework always exhibits 33 nt (that is, 11 aa) and is identical in all 7 families: TGG.GGC.CAA.G-GC.ACC.CTG.GTG.ACG.GTT.AGC.TCA VL Kappa Chain:

The 1-region framework extends from nt 1-69 (that is, 23 aa); the last codon (aa) of FR1 is always: TGC (Cys).

The "CDR1 region" can be of four different lengths: either 24 nt (8 aa) (possible in families Vk1 and Vk3), 27 nt (9aa) (possible in family Vk3), 39 nt (13 aa) (possible in family Vk2), or 42 nt (14 aa) (possible in family Vk4); first codon (aa) always AGA (Arg); penultimate codon (aa) of CDR1 region always: CTG (Leu).

The 2-region framework always exhibits 33 nt (that is, 11 aa); the first two codons (aa) of FR2 are always: TGG-.TAC (Trp Tyr); the penultimate codon is always CCG (Pro).

The "CDR2 region" always exhibits 33 nt (that is, 11 aa), whereby the first three codons (aa) are always CTA.T-TA.ATT (Leu Leu Ile).

The 3-region framework always exhibits 96 nt (that is, 32 aa); the first three codons (aa) of FR3 are always: GGG.GTC.CCG (Gly Val Pro); the last three codons are always TAT.TAT.TGC (Tyr Tyr Cys).

The "CDR3 region" always exhibits 24 nt (that is, 8 aa), whereby the second codon (aa) is always CAG (Gln).

The 4-region framework always exhibits 39 nt (that is, 13 aa) and is identical in all four families: ACC.TTT.GGC-.CAG.GGT.ACG.AAA.GTT.GAA.ATT.AAA.CG-T.ACG.

VL Lambda Chain:

The 1-region framework extends from nt 1-66 (that is, 22 aa); the last codon (aa) of FR1 is always: TGT (Cys).

The "CDR1 region" can exhibit three different lengths: either 33 nt (11 aa) (possible in family V13), 39 nt (13 aa) (possible in family V11), or 42 nt (14 aa) (possible in families V11 and V12).

The 2-region framework always exhibits 33 nt (that is, 11 aa); the first two codons (aa) of FR2 are always: TGG-.TAC (Trp Tyr); the third last codon is always GCG (Ala).

The "CDR2 region" always exhibits 33 nt (that is, 11 aa), whereby the third codon (aa) is always ATT (Ile), and the last three codons are always CGT.CCC.TCA (Arg Pro Ser).

The 3-region framework always exhibits 96 nt (that is, 32 aa), whereby the first codon (aa) of FR3 is always: GGC (Gly), and the last four codons are always GAT.TAT-.TAT.TGC (Asp Tyr Tyr Cys).

The "CDR3 region" can exhibit three different lengths: either 24 nt (8 aa), 27 nt (9 aa), or 30 nt (10 aa).

The 4-region framework always exhibits 39 nt (that is, 13 aa) and is identical in all 3 families: GTG.TTT.GGC.G-GC.GGC.ACG.AAG.TTA.ACC. GTT.CTT. GGC-.CAG.

For therapeutic or diagnostic purposes, e.g., for an in vitro or in vivo diagnosis, the polypeptide according to the invention can be used.

For therapeutic applications, the polypeptide according to the invention can be present in the form of a conjugate with a therapeutic active ingredient, for example selected from radiotherapy agents or chemotherapy agents, e.g., low-molecular or biological cytostatic or cytotoxic active ingredients. The conjugation of the therapeutic active ingredient on the polypeptide can be carried out according to known methods, preferably via a covalent coupling to reactive amino, carboxy, hydroxy and/or thiol groups of the protein, optionally with use of homo- or hetero-bifunctional linkers, according to known methods.

Moreover, the polypeptide can also be present in the form of a fusion protein, which, in addition to the antibody, e.g., in the form of an IgG molecule or a fragment thereof, contains a cytokine fused thereto, e.g., IL2, Il12 or $TNF_{\alpha}$-polypeptide. In addition, the fusion protein can be present in the form of a bispecific antibody, whereby in addition to the binding to the ED-B domain, a binding to another antigen is preferred. Other antibody specificities of bispecific antibodies are binding domains against chelating agents for diagnostically and therapeutically relevant radionuclides, e.g., α-, β- or γ-emitters, such as, for example, $^{90}Y$, diagnostic NIR (near-infrared)-dyes, therapeutically effective dyes, surface molecules on immunological effector cells (e.g., NK cells, cytotoxic T cells, or NKT cells), angiogenesis-relevant integrins, in particular binding domains that block their function (e.g., $\alpha_1$, $\beta_3$, $\alpha_1\beta_3$, $\alpha_2\beta_1$, $\alpha_2\beta_2$), inactivating anti VEGF-binding domains and inactivating binding domains against VEGF receptors 1, 2 and 3.

For diagnostic applications, the polypeptide can be present in the form of a conjugate of a diagnostically detectable labeling group, e.g., a labeling group for an in vitro or an in vivo diagnosis. Examples of labeling groups are radioactive labeling groups, NMR-, dye-, enzyme- and fluorescence- (e.g., fluorescence in the near-infrared range) labeling groups.

For therapeutic applications, the polypeptide is preferably formulated as a pharmaceutical composition that as active ingredient contains the polypeptide according to the invention, optionally additional active ingredients as well as pharmacologically common vehicles, adjuvants and/or diluents. The pharmaceutical composition contains the active ingredient in a therapeutically effective dose that can be determined by one skilled in the art in a simple way by in vitro tests, for example on suitable cell cultures, or in animal models. The administration of the composition is preferably carried out by injection or infusion, but also other types of administration are conceivable. An intravenous and/or subcutaneous administration is preferably carried out. The dose of the administered active ingredient depends on the type and the severity of the disease as well as the condition of the patient to be treated. The therapeutic composition is preferably administered several times over an extended period of, for example, at least 2-4 weeks. In this connection, reference is made to known processes for administering antibodies or antibody conjugates, as described in, for example, Ferarra, N. et al., Nature Reviews Drug Discovery, Volume 3, May 2004, 391-400 and Salgaller, M. L., Current Opinion in Molecular Therapeutics 2003 5(6): 657-667, or to existing administration procedures for pharmaceutical antibodies, such as Rituximab, CAMPATH, Remicade, etc.

Another subject of the invention is a diagnostic composition that comprises a polypeptide according to the invention as a diagnostic reagent. In addition, the diagnostic composition can still contain additional diagnostically common reagents, vehicles, adjuvants and/or diluents. The diagnostic composition contains the polypeptide in a sufficient amount to make possible diagnostic detection in the respective format, e.g., in an in vivo or in vitro diagnostic format. In this connection, reference is made to known processes for in vivo and in vitro diagnosis with use of labeled antibodies.

The pharmaceutical and diagnostic compositions can for therapy and diagnosis of all diseases that are accompanied by an ED-B expression, for example a stromal and/or perivascular ED-B expression. Examples of such diseases are hyperproliferative diseases, e.g., diseases that are associated with angiogenesis, in particular cancer, ocular fundus diseases, hypertrophic scars, etc., diseases that are associated with a myofibroblast malfunction, e.g., endometriosis, arteriosclerotic plaque, etc., or inflammatory diseases, e.g., psoriasis, Crohn's disease, rheumatoid arthritis or multiple sclerosis.

The pharmaceutical or diagnostic composition according to the invention can contain one or more active polypeptides, e.g., a combination of polypeptides, which bind to different areas of the ED-B domain. The compositions are suitable for use in human and veterinary medicine.

Another subject of the invention is a nucleic acid that codes for a peptide or fusion polypeptide according to the invention. This nucleic acid can be a single-strand or double-strand DNA or an RNA. The nucleic acid is preferably in operative linkage with an expression monitoring sequence, which makes possible an expression in a suitable host cell or a suitable host organism. The nucleic acid can be present on a vector that is suitable for introduction into a host cell or a host organism. The vector can be, for example, a prokaryotic vector, suitable for introducing prokaryotic cells, e.g., a plasmid or bacteriophage. In contrast, the vector can also be a eukaryotic vector, suitable for introduction into eukaryotic host cells or host organisms, e.g., a plasmid, an artificial chromosome or a viral vector. Suitable vectors are known to one skilled in the art, for example from Sambrook et al. (1989), Molecular Cloning, A Laboratory Manual, Cold Spring Harbor Laboratory Press, and Ausubel et al. (1989), Current Protocols in Molecular Biology, John Wiley and Sons.

Still another subject of the invention is a cell, e.g., a prokaryotic cell or a eukaryotic cell, such as, for example, a human cell, which is transformed with a nucleic acid according to the invention or a vector according to the invention. Another subject of the invention is a non-human organism, e.g., a transgenic animal, which is transformed with a nucleic acid according to the invention or a vector according to the invention. In this case, the term "transformation" within the scope of this invention contains all possibilities for introducing foreign nucleic acids into a cell or an organism including transfection or infection.

The polypeptide according to the invention can be made by cultivating a cell according to the invention or a non-human organism according to the invention under conditions in which an expression of the polypeptide is accomplished, and then the expressed polypeptide is obtained, e.g., from the cell, the culture medium, the organism or excretion products of the organism.

In addition, the invention is to be explained by the figures and examples below:

FIG. 1 shows the diagrammatic implementation of an inhibition test for identifying functionally active antibodies.

Human endothelial cells, which were obtained from microvessels of the skin (human dermal microvessel endothelial cells, HDMVEc), were incubated together with ED-B-specific Fab-antibody fragments. The number of bonded cells is made visible by means of crystal violet staining and measured in a photometer. High color intensity means many adherent cells and no binding-blocking antibodies. Low color intensity means little adhesion and a binding-blocking antibody.

FIG. 2 shows a screening diagram for identifying ED-B-fibronectin-function-blocking antibodies by means of a Fab-fragment display.

In a first step, a panning procedure with recombinant ED-B is performed. The antibody fragments that are obtained in this way are subjected to a specificity test (ELISA), a functional adhesion test as well as an immunohistochemical study. Then, the affinity of the antibodies that carry out these tests is determined. Then, changes in the CDR domains are performed to improve the affinity, whereby affinity maturation 1 means a change in the L-CDR3 domain and affinity maturation 2 means a change in the H-CDR2 domain.

After the antibodies, obtained by affinity maturation, have passed through the above-mentioned tests, then the in vivo effectiveness is tested.

FIG. 3 shows the results of a specificity test in ELISA format with the antibody-Fab fragments that are produced by panning with recombinant ED-B.

ED-B means the binding to recombinant ED-B, 6-FN means the binding to the recombinant fibronectin-domain 6, domain 7-8-9 means the binding to recombinant fibronectin domains 7-8-9 (without ED-B), and domain 7-EDB-8-9 means the binding to the recombinant fibronectin domains 7-8-9 with ED-B. The ratio of ED-B to 6-FN or 7-8-9 produces the specificity of the antibody under study. AP-39 means a covalent dimer of the biologically inactive anti-ED-B scFv antibody L19.

FIG. 4 shows the result of an adhesion test with the antibodies under study.

The inhibition of the adhesion of HDMVEc cells to ED-B-coated plates by the indicated Fab fragments at concentrations of 25 μg/ml or 0.4 μg/ml Fab was examined. The indicated values are the result of 3× determination.

FIG. 5 shows the immunohistochemical reaction pattern of function-blocking anti-ED-B-Fab fragments in the example of MOR 02616. In FIGS. 5A and 5C, the results with a negative control (negative HuCAL-Fab), and in FIGS. 5B and 5D, the results with the antibody MOR 02616 on human neuroblastoma cell-IRM xenotransplants (FIGS. 5A and 5B) as well as on murine F9-teratocarcinoma cells (FIGS. 5C and 5D) are shown.

Cryosections of cells (thickness: 10 μm) were air-dried and then set in ice-cold acetone for 10 minutes. Then, the sections were washed in PBS and incubated for 60 minutes with 2 μg/ml of MOR 02616 or negative controls at room temperature. As a secondary antibody, a peroxidase-labeled polyclonal goat anti-human $F(ab)_2$ antiserum (1:100 diluted in PBS, Dianova) was used in combination with diaminobenzidine (Sigma Chemicals) as a chromogenic substrate.

FIG. 6 shows the results of a specificity test in ELISA format with the antibody Fab fragments that are optimized by maturation.

The execution of the test was as described in FIG. 3.

FIG. 7 shows the immunohistochemical reaction pattern of the antibody Fab fragments MOR 03255, optimized by maturation, on cryostat sections of F9-teratocarcinoma cells (FIG. 7A) and on SKMEL-28 human-melanoma cell xenotransplants in hairless mice (FIG. 7B).

The execution of the test was as described in FIG. 5.

FIG. 8 shows the result of an adhesion test with the antibody Fab fragments according to the invention relative to the comparison antibodies L19 and Ly6 0.3.

The execution of the test was described very much like in FIG. 4. The antibody concentrations were 1 μl/ml, 10 μl/ml or 20 μl/ml.

FIG. 9 shows the stability of the antibody-Fab fragments according to the invention after incubation for 4 hours in human plasma or PBS at 37° C.

The immune reactivity was determined in the ELISA test with concentrations in the range of 0.039 to 5 μg/ml. The signal with 0.62 μg/ml in human plasma without incubation was defined as a 100% value.

FIGS. 11(A-H) show the nucleotide sequences that code for the VH and VL regions of the antibodies according to the invention.

EXAMPLE

Figure 1:
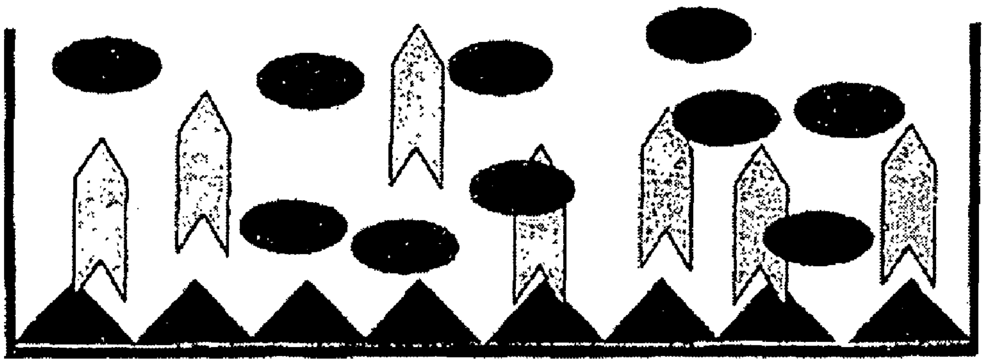
Figure 2:
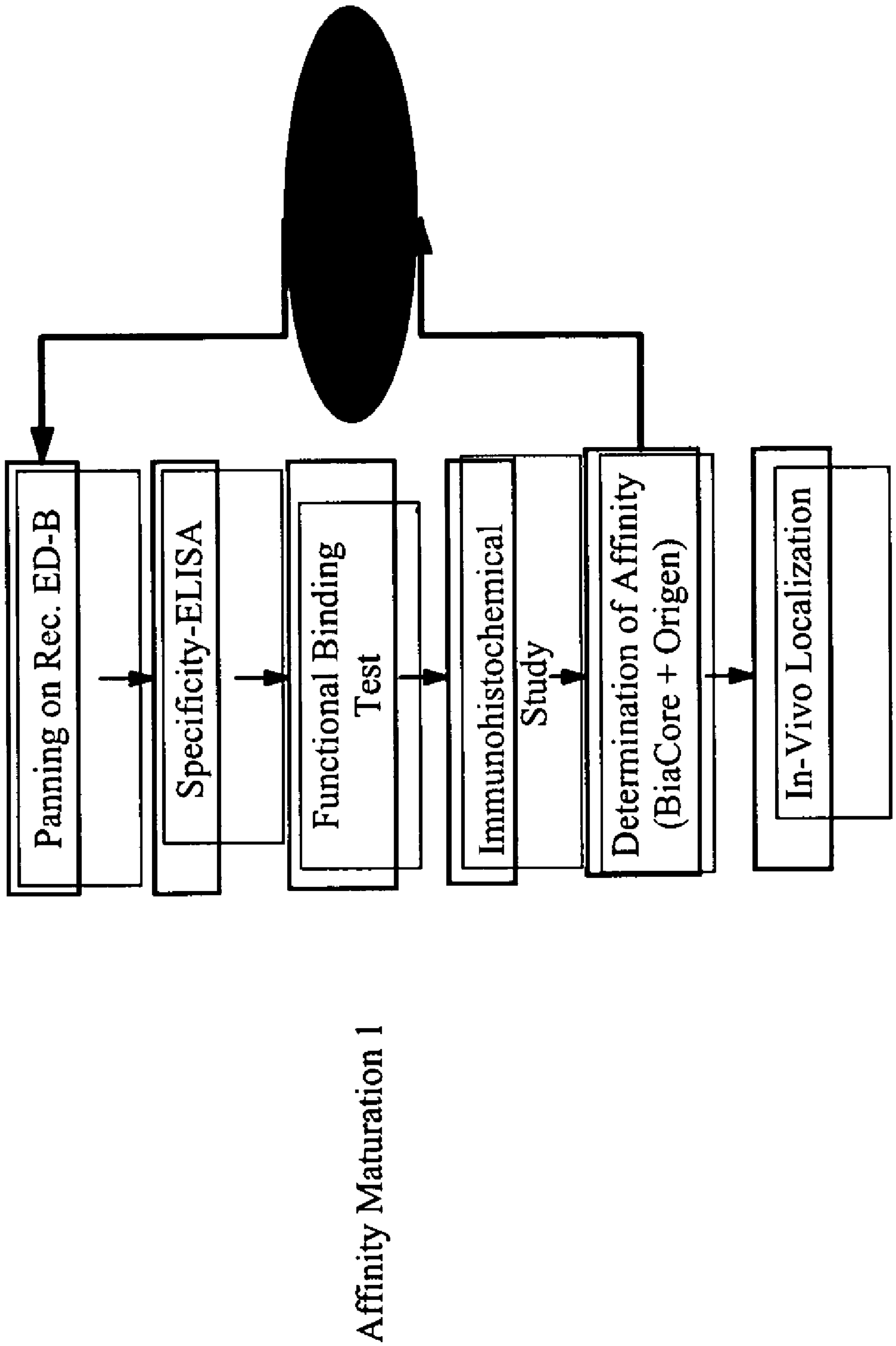

1. Material and Methods 1.1 Proteins and Antibodies

Purified recombinant fibronectin domain ED-B $(His)_6$, fibronectin domain 6 (6FN), fibronectin domain 7-8-9 and domain 7-ED-B-8-9 were produced according to standard procedures (e.g., Sambrook et al., Molecular Cloning. A Laboratory Manual, Cold Spring Harbour Press).

Mouse antibodies against purified ED-B receptors were also produced according to standard processes by 50 μg of purified receptor being administered in Freund's complete adjuvant to a mouse, 3 weeks later 25 μg of purified receptor being administered in Freund's incomplete adjuvant, and another 3 weeks later all applications being administered intraperitoneally in incomplete adjuvant. Blood was then removed via the postorbital sinus 14 days after the $3^{rd}$ immunization.

Plasma fibronectin was ordered from Sigma.

1.2 Selection of ED-B-Specific Phages

The selection was performed according to the HuCAL® Gold Phage selection protocol. The HuCAL® Gold Library was subdivided into six framework-specific pools. The ED-B-specific phages were concentrated in three successive selection rounds of recombinant protein immobilized in 96-hole plates (Maxisorb, Nunc, Rochester, N.Y., USA). For panning A, the plate was coated with 1 μg/hole of ED-B $(His_6)$ (10 μg/ml in Ampuwa®) for 2 hours at 37° C. For panning B, the plate was coated with ED-B in the same concentration in PBS (pH 7.2 with 1 mmol of $MgCl_2$/1 mmol of $CaCl_2$) overnight at 4° C. The plates were blocked with 5% skim milk powder in PBS, 0.05% Tween20 (Sigma, St. Louis, Mo., USA) (blocking buffer) and incubated with $1\times10^{13}$ HuCAL® Gold phages, which had been preincubated with a volume of blocking buffer. For panning B, the phages were pre-incubated in addition with 0.5 μg/ml of fibronectin-domain 6 in order to reduce the selection of binding molecules that are specific to the conserved structure of a type-3 domain repetition of fibronectin. After an incubation with the phages for 2 hours at room temperature, the holes were washed 5× with PBS, 0.05% Tween20 and 5× with PBS. The remaining phages were eluted with 20 mmol of dithiothreitol (DTT) in 10 mmol of tris/HCl (pH 8.0) for 10 minutes at room temperature. Then, an incubation with *E. coli* TG-1 (Stratagene, $OD_{600}$=0.5) was carried out for infection. Then, the holes were incubated with *E. coli* TG-1 as an additional elution step.

1.3 Phagemid Recovery, Phage Amplification and Purification

Die HuCAL® Gold phages were amplified in 2×TY medium with 34 μg/ml of chloramphenicol and 1% Glucose (2×TY-CG). After infection with a helper phage (VCSM13) at 37° C. and an $OD_{600}$ of about 0.5, centrifuging and resuspending in 2×TY-CG/50 μg/ml of kanamycin, the cells were induced with 0.25 mmol of IPTG and cultivated overnight at 22° C. The phages were precipitated from the supernatant with polyethylene glycol (Ausubel et al. (1998), Current Protocols of Microbiology), resuspended in PBS and used for subsequent selection rounds.

1.4 Subcloning of Selected Fab Fragments and Expression of Soluble Fab Fragments The Fab-coding insertions of the selected HuCAL® Gold phages were subcloned in the expression vector pMORPHx9-FS. The plasmid-DNA preparation of the selected HuCAL® Gold clone was cleaved with the restriction enzymes XbaII/EcoRI, whereby the Fab-coding insertion was cut out (ompA-VL and phoA-Fd). Fab molecules that are expressed in this vector contain two C-terminal labelings (FLAG™ and Strep-tagII) for detection and for purification.

1.5 Expression and Purification of HuCAL® Gold Antibodies in *E. coli*

The expression of the TG-1 F cells on pMORPHx9-FS-coded Fab fragments in *E. coli* was performed in shaking bottle cultures with 0.75 l of 2×TY medium and 34 μg/ml of chloramphenicol. After induction with 0.75 mmol of IPTG, the cells were cultivated for 16 hours at 30° C. As an alternative, Fab clones, which had been obtained from the second maturation pool 2, were induced with 0.1 mmol of IPTG and then cultivated at 22° C. Periplasmatic extracts from cell pellets were produced by osmotic shock, and the Fab fragments were isolated by Strep-Tactin® chromatography (IBA, Göttingen, Germany). The apparent molecular weights were determined by size-exclusion chromatography (SEC) with calibrating standards. The concentrations were determined by UV spectrometry.

1.6 Identification of ED-B-Binding Fab-Fragments by ELISA

96-Hole-Maxisorb ELISA plates were coated with 100 μl of ED-B solution (10 μg/ml in coating buffer (PBS pH 7.4, 1 mmol of $CaCl_2$, 1 mmol of $MgCl_2$) overnight at 4° C. Crude lysates or purified Fab molecules were added; non-binding Fab molecules were removed by 5× washing with washing buffer (PBS pH 7.4, 0.05% Tween20). The Fab fragments were detected by incubation with anti-human-Fab-antibody-peroxidase conjugates (Dianova), followed by development with a soluble peroxidase substrate (Roche) and measurement at 370 nm. The clones that express for ED-B-specific Fab molecules were identified by a positive ELISA signal on immobilized ED-B versus little or no signal at 6FN.

1.7 Determination of Plasma Stability Under Physiological Temperature Conditions by ELISA The coating with ED-B (2.5 μg/ml) was performed essentially as described above. The Fab fragments were incubated for 4 hours at 37° C. and a concentration of 50 μg/ml in human plasma (German Red Cross; Batch 9985550). After incubation, the Fab molecules were diluted for the ELISA Test to the concentrations of 5.0, 2.5, 1.25, 0.62, 0.31, 0.156, 0.078 and 0.039 μg/ml in PBS with 1% bovine serum albumin to determine the linear area of the signal intensity. Functional Fab molecules were determined with the anti-Flag M2 antibody (Sigma F3165) and a secondary anti-mouse-antibody-alkaline phase conjugate, followed by development with Attophos (Roche) and by measurement at 535 nm.

1.8 HDMVEc Cell Culture and Cell Adhesion Test

Human dermal microvascular endothelial cells (HDMVEc), isolated from juvenile foreskin, were cultivated in EGM-MV medium (Clonetics, Inc.) with the addition of 10% fetal calf serum, 2 mmol of glutamine, 20 μg/ml of heparin and 3 ng/ml of bFGF in vessels, coated with 0.1% gelatin (Sigma). For adhesion tests, cells that had not been cultivated longer than passage 8 were used. ED-B (10 μg/ml) or plasma fibronectin (2.5 μg/ml) was immobilized overnight at 4° C. in PBS, pH 7.4, 0.9 mmol of $CaCl_2$, 0.5 mmol of $MgCl_2$ in 96-hole ELISA plates and blocked with 1% RSA in PBS, pH 7.4, 0.9 mmol of $CaCl_2$, 0.5 mmol of $MgCl_2$ for 1 hour at 37° C. The cells were labeled with 0.15 μg/ml of calcein for 30 minutes at 37° C. and washed once in adhesion medium (MCDB 131, 2 mmol of glutamine, 0.1% RSA, 20 μg/ml of heparin). $1\times10^5$ cells were incubated for 20 minutes at 37° C. with the antibody concentration that is indicated in each case, diluted in adhesion medium (final volume 100 μl). The cell suspension was added to the ED-B-coated plates for 2 hours at 37° C. After the cells are washed 2× in PBS, pH 7.4, 0.9 mmol of $CaCl_2$, 0.5 mmol of $MgCl_2$, adherent cells were detected in a plate fluorimeter (excitation 485 nm; emission 530 nm).

As a control, (A) the cell binding to ligand-coated plates was determined without adding specific antibodies, and (B) the cell adhesion to holes was determined without ligand coating, whereby the value obtained in the last-mentioned control was defined as a minimum of cell adhesion in the test.

1.9 Affinity Maturation of Selected Fab Molecules by Exchange of CDR Cassettes in Steps To increase the affinity and biological activity of selected antibody fragments, CDR regions were optimized by cassette mutagenesis with use of trinucleotide-directed mutagenesis.

To this end, Fab fragments from the expression vector pMORPHx9 in the phagemid vector pMORPH-23 were cloned with use of the EcoRI/XbaI restriction sites. To optimize the affinity of the selected Fab fragments, two successive maturation steps for each maturation pool were performed. In the first step, an antibody fragment-phage library was produced in which the L-CDR3 region of the starting clone was varied by a repertoire of $7\times10^8$ (Pool 1) and $3.8\times10^8$ (Pool 2) individual light chain-CDR sequences. Then, affinity-improved derivatives from the first maturation step were exposed to a second maturation round by the H-CDR-2 region being replaced by a library of diversified elements. In this way, two phage libraries with $1\times10^8$ individual clones in each case were produced.

The affinity maturation libraries were produced by transformation into *E. coli* TOP10F. The phages were produced as described above. The selection in Fab fragments with improved affinity was performed under stringent conditions for three rounds in the first maturation and for two rounds in a second step.

1.10 Determination of Affinity by Surface Plasmon Resonance (BIAcore®)

To determine the $K_D$ values, monomer fractions (at least 80% monomer content, determined by analytical SEC; Superdex75, Amersham Pharmacia) of Fab fragments were used. F1-Chips (Biacore, Sweden) were coated with about 200 RU of ED-B (30 μg/ml, 10 mmol of acetate buffer, pH 4.0) and reference flow cells with a corresponding amount of human serum albumin (20 μg/ml, 10 mmol of acetate buffer, pH 4.5) with use of standard EDC-NHS-amine-coupling chemistry. The antigen density was reduced to about 100 RU for the Fab characterization of the second maturation. The regeneration was carried out with 10 mmol of HCl. All kinetic measurements were carried out in PBS buffer (136 mmol of NaCl, 2.7 mmol of KCl, 10 mmol of $Na_2HPO_4$, 1.76 mmol of $KH_2PO_4$, pH 7.4) with a flow rate of 20 μl/minute with use of a Fab concentration range of 1.5-500 nmol. The injection period was 1 minute in each case. All sensograms were evaluated with use of BIA evaluation software 3.1.

Abbreviations: EDC: 1-Ethyl-3-(3-dimethylaminopropyl) carbodiimide, NHS: N-Hydroxysuccinimide, RU: Resonance Units 2. Results 2.1 Production of Antibodies Against Human ED-B Two different panning assays were implemented. The coating with ED-B for the first assay (panning A) was performed according to the conditions known from the biological test to present ED-B in a conformation that allows the adhesion of HDMVEc cells to the immobilized antigen. With the second panning (B), the phages were blocked in addition with excess 6FN to avoid a selection of binding molecules that cross-react with the fibronectin-domain 6.

Figure 3:
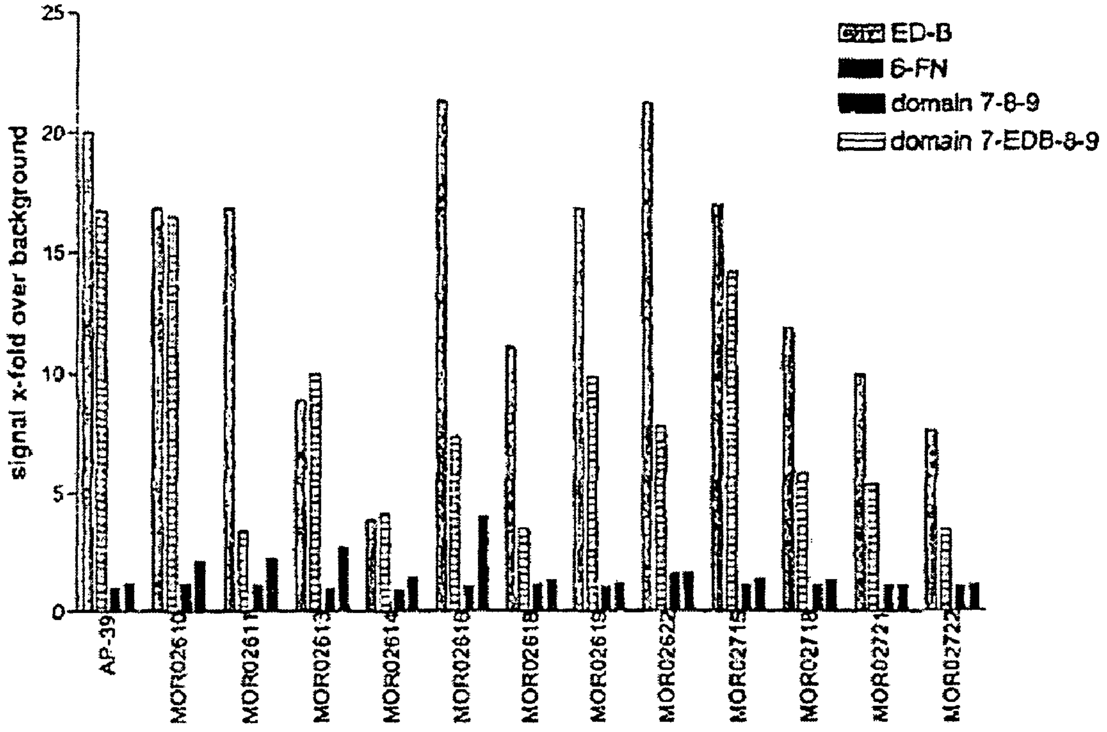

Altogether, 23 different HuCAL-Fab molecules from 1315 primary hits were found that meet the criteria of binding to ED-B and not to 6FN. In addition, the antibodies were tested in their capacity for binding to a recombinantly expressed fibronectin, comprising the domains 7, 8 and 9 with and without the inserted ED-B domains in their natural arrangement (see FIG. 3). All tested antibodies showed a specific recognition for the 7-ED-B-8-9 construct but did not react with the corresponding construct without the ED-B domain.

2.2 Functional Characterization of the ED-B Specific Binding Molecule

The antibodies as specifically identified in ELISA were purified and tested in their capacity for blocking the adhesion of HDMVEc cells to ED-B-coated plates. The adhesion of HDMVEc cells in the presence of ED-B-specific Fab fragments in two concentrations was tested in comparison to an unspecific HuCAL-control-Fab-molecule and positive mouse control sera.

Figure 4:
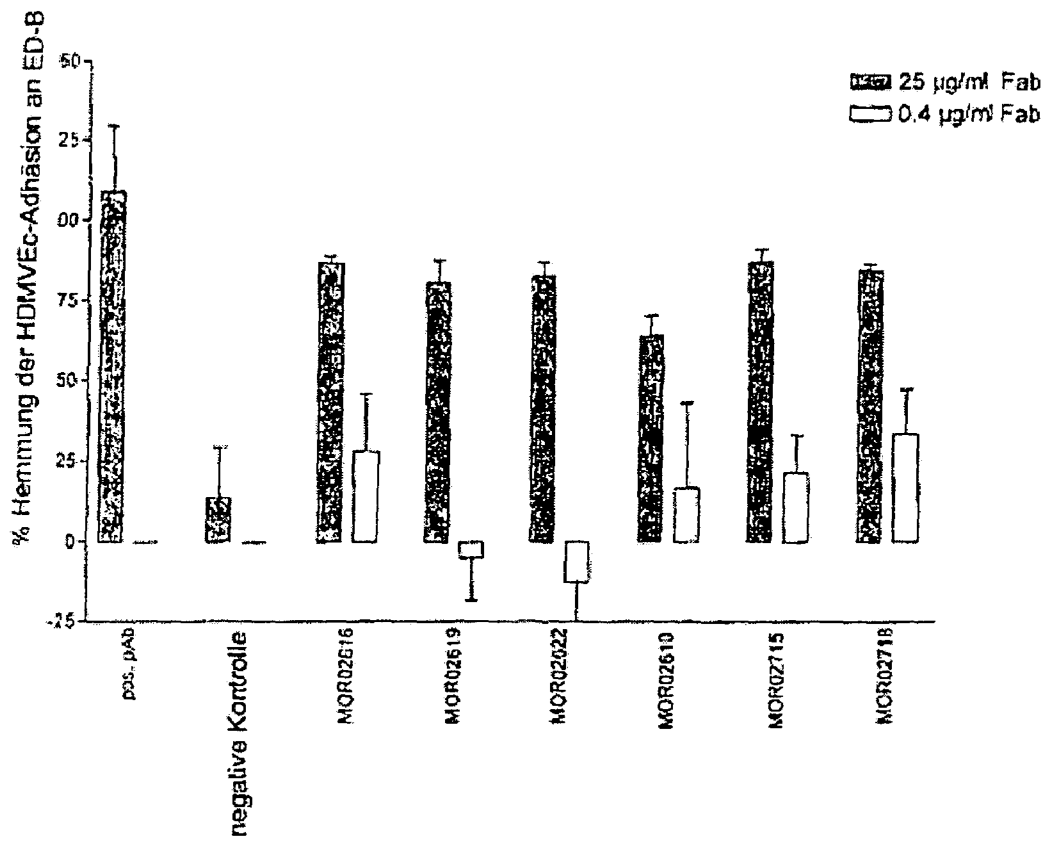

Twelve of the 23 Fab molecules described in Section 2.1 showed an inhibition of cell adhesion in immobilized ED-B. A representative selection of the six most effective Fab molecules is shown in FIG. 4. At a concentration of 25 μg/ml, the cell adhesion was inhibited by 50% to almost 100%. At a concentration of 0.4 μg/ml, only a few Fab molecules, e.g., MOR02610, MOR02616, MOR02715 and MOR02718, showed a reproducible inhibition of the cell adhesion.

Figure 5A:
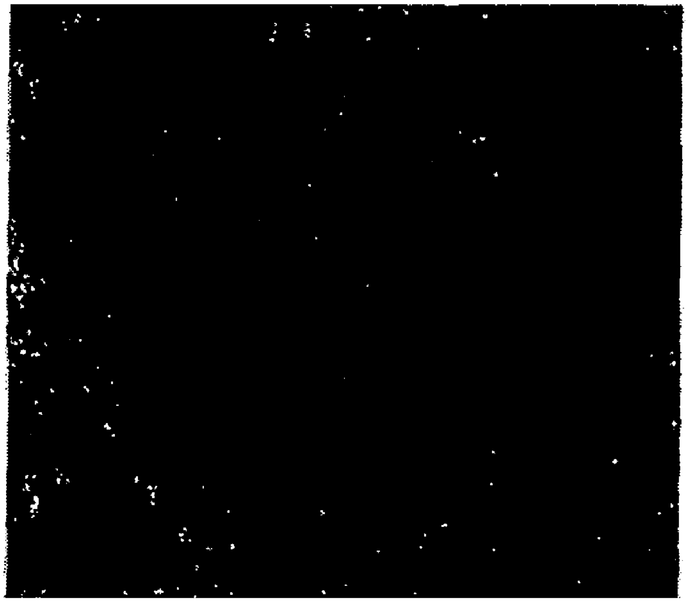
Figure 5B:
Figure 5C:
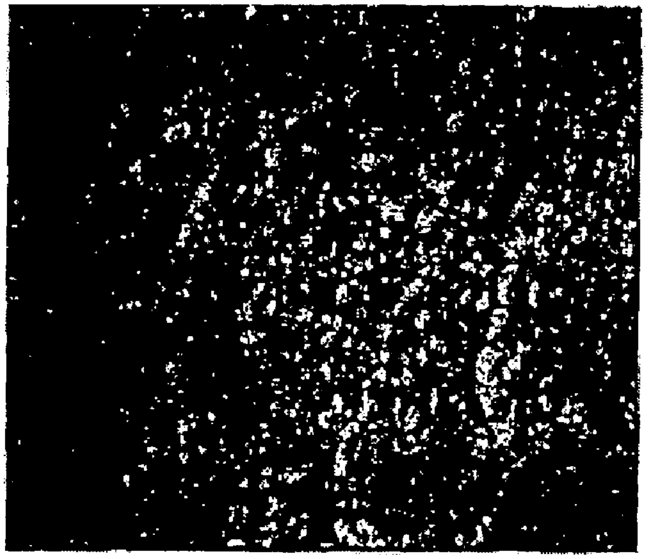
Figure 5D:
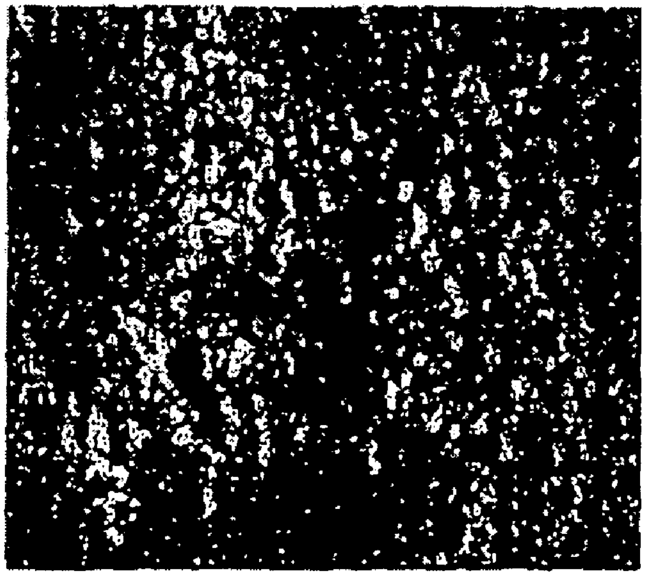

The function-blocking Fab-antibody fragments were characterized by immunohistochemistry with respect to their localization on F9-mous-teratocarcinoma cells and human IRM30 neuroblastoma-xenotransplant cryosections. All tested antibodies showed a vascular localization on two tissue sections, but no staining of vessels on normal tissue (e.g., normal and sclerotic liver and skin). In FIGS. 5B and 5D, a perivascular abluminal staining of vessels, proliferating endothelium and tumor stroma by MOR02616 is shown. A collection of ED-B in the vicinity of neovascular structures of exponentially growing tumors, but not in normal vessels, can be detected. With a negative control antibody against lysozyme at the same concentration, no staining was visible (FIGS. 5A and 5C).

The properties of twelve selected binding molecules was determined by BIAcore analysis (see Table 1). The affinities ($K_{on}$) were in the range of 15 to 500 nmol. The affinity of the bivalent L19 derivative AP39 (a biologically inactive comparison antibody against ED-B) was determined with 2.4 nmol. Table 1 also shows the CDR sequences (only L-CDR3 and H-CDR3) and the framework combinations. At least two independent measurements with Fab molecules from different batches were performed for protein expression and protein purification. The binding rate ($K_{on}$) and the dissociating-off rate ($K_{off}$) of the Fab molecule are indicated in separate columns.

TABLE 1

| Clone | VH | H-CDR3 | VL | L-CDR3 | kon [1/Ms] | koff [1/s] | KD [nM] |
|---|---|---|---|---|---|---|---|
| AP 39 | VH3 | PFPY--FDY | K3 | QQTGRI--PP | 6.6E+05 | 1.5E-03 | 2.4 ± 0.6 |
| MOR02610 | VH1B | SPVYYKYDY | L1 | QSYDKTSSTY | 1.3E+06 | 9.1E-02 | 75 ± 19 |
| MOR02611 | VH1B | GLYYR-FAS | L2 | AAATG---GW | 1.5E+05 | 5.1E-02 | 332 ± 23 |
| MOR02613 | VH3 | YVNG--FDI | L2 | QTYAKKDYSL | 7.8E+05 | 1.3E-01 | 164 ± 14 |
| MOR02614 | VH3 | A-----YDV | L1 | AMFSP---EG | 2.8E+05 | 4.2E-02 | 160 ± 6 |
| MOR02616 | VH3 | VIVL--FDY | K3 | LQKYSI--PF | 5.4E+05 | 2.8E-02 | 59 ± 25 |
| MOR02618 | VH3 | NYWV--FAY | L3 | QSYDNFNDSV | 4.3E+05 | 2.0E-01 | 477 ± 177 |
| MOR02619 | VH4 | F-----FDV | L1 | QSWDGAS-TG | 7.8E+05 | 1.2E-02 | 15.4 ± 0.6 |
| MOR02622 | VH3 | GLVT--FDN | L2 | SSWTHSFTDY | 2.4E+05 | 5.1E-03 | 21.3 ± 1.7 |
| MOR02715 | VH3 | NKVG--FDV | L2 | QAWDNQGMKY | 8.9E+05 | 4.7E-02 | 53.7 ± 1.7 |
| MOR02718 | VH3 | GMF---FAH | K3 | FQYSSK--PL | 4.5E+05 | 3.9E-02 | 85 ± 12.5 |
| MOR02721 | VH5 | YH----GAF | L1 | QAYTTG--SI | 4.3E+05 | 2.4E-02 | 56 ± 11.6 |
| MOR02722 | VH3 | F-----IAS | K2 | QQYSNF--PF | 1.5E+05 | 1.4E-02 | 94 ± 2.3 |

Key:
MOR02610 VH (SEQ ID NO:1) VL (SEQ ID NO:3)
MOR02611 VH (SEQ ID NO:5) VL (SEQ ID NO:7)
MOR02613 VH (SEQ ID NO:9) VL (SEQ ID NO:11)
MOR02614 VH (SEQ ID NO:13) VL (SEQ ID NO:15)
MOR02616 VH (SEQ ID NO:17) VL (SEQ ID NO:19)
MOR02618 VH (SEQ ID NO:21) VL (SEQ ID NO:23)
MOR02619 VH (SEQ ID NO:25) VL (SEQ ID NO:27)
MOR02622 VH (SEQ ID NO:29) VL (SEQ ID NO:31)
MOR02715 VH (SEQ ID NO:33) VL (SEQ ID NO:35)
MOR02718 VH (SEQ ID NO:37) VL (SEQ ID NO:39)
MOR02721 VH (SEQ ID NO:41) VL (SEQ ID NO:43)
MOR02722 VH (SEQ ID NO:45) VL (SEQ ID NO:47)

2.3 Affinity Maturations of Function-Blocking ED-B-Antibodies by Optimization of L-CDR3 and H-CDR2 Regions The affinity maturations of the Fab molecules were performed in two sections. First, the L-CDR3 sequence was diversified, and then the H-CDR2 sequence of the improved Fab molecule, obtained in the first step, was exchanged.

Two affinity maturation libraries for each step were produced. The optimization was performed in two separate pools. The L-CDR3 library 1 with a degree of diversity of $7\times10^8$ elements contained the four starting Fab molecules MOR02610, MOR02616, MOR02619 and MOR02622. The L-CDR3 library 2 with a degree of diversity of $3.8\times10^8$ elements contained only derivatives of MOR02715 and MOR02718. Here, the Fab molecules were combined into groups in each case according to their affinity and biological activity in the adhesion test.

The two libraries were kept separately during the selection procedure. In this case, two panning strategies were performed. Panning I was carried out with ED-B immobilized on maxisorb plates for three rounds, as previously indicated. With Panning II, a selection of biotinylated ED-B in solution was carried out. In this case, the phage-antigen complex was recovered by streptavidin-coated particles in the first round and on neutravidin plates in the two subsequent rounds. Stringent conditions were used within the scope of the selection procedure.

The screening on optimized Fab molecules was carried out by determining the $K_{off}$ values in the BIAcore system. Altogether, 11 derivatives of library I were characterized. The 5 derivatives with the highest affinity are indicated in Table 2. In this case, all improved clones are derivatives of MOR02619 with an increase in affinity of up to 7×. In clone MOR03075, an affinity of 2.4 nmol was found.

From library 2, two derivatives of MOR02715 were analyzed in detail. For clone MOR03062, a 15-fold affinity increase was found, so that a monomer affinity of 2.4 nm was obtained. The changes in the amino acid sequence of the L-CDR3 region are shown in Tables 2a and 2b.

TABLE 2a

| Panning Pool 1 | MOR0 | Initial Clone | LCDR3 | Kon [1/Ms] | Koff [1/s] | KD [nm] | x-Fold Improvement Relative to the Parent Clone Kon | Koff | KD |
|---|---|---|---|---|---|---|---|---|---|
| | AP 39-Biotin | | QQTGRI--PP | 6.6E+05 | 1.49E-003 | 2.4 ± 0.6 | | | |
| | 2619 | | QSWDGAS-TG | 7.8E+05 | 1.2E-02 | 15.4 ± 0.6 | | | |
| Solid | 3055 | 2619 | QAWTRAHRYP | 1.8E+06 | 5.1E-03 | 3.0 ± 0.5 | 2.2 | 2.6 | 5.4 |
| Dissolved | 3066 | 2619 | SSYD-TQVTR | 1.1E+06 | 4.7E-03 | 4.2 ± 0.6 | 1.4 | 2.8 | 3.8 |
| Dissolved | 3075 | 2619 | QSWDP-RSFT | 1.1E+06 | 2.6E-03 | 2.4 ± 0.3 | 1.4 | 5.0 | 6.8 |
| Dissolved | 3069 | 2619 | WTGM--SYHF | 1.2E+06 | 4.1E-03 | 3.3 ± 0.2 | 1.5 | 3.2 | 4.8 |
| Dissolved | 3071 | 2619 | LAYIQS-KGH | 1.9E+06 | 5.7E-03 | 3.1 ± 0.8 | 2.3 | 2.3 | 5.1 |

Key:
MOR02619 VL (SEQ ID NO:27)
MOR03055 VL (SEQ ID NO:49)
MOR03066 VL (SEQ ID NO:51)
MOR03075 VL (SEQ ID NO:53)
MOR03069 VL (SEQ ID NO:55)
MOR03071 VL (SEQ ID NO:57)

TABLE 2b

| Panning Pool 2 | MOR0 | Parent clone | LCDR3 | Kon [1/Ms] | Koff [1/s] | KD [nm] | x-Fold Improvement Relative to the Parent Clone Kon | Koff | KD |
|---|---|---|---|---|---|---|---|---|---|
| | AP 39-Biotin | | QQTGRI--PP | 6.75E+05 | 1.49E-03 | 2.4 ± 0.6 | | | |
| | 2715 | | QAWDNQGMKY | 9.9E+05 | 4.7E-02 | 53.7 ± 1.7 | | | |
| Solid | 3064 | 2715 | QSWDLLAPSV | 1.5E+06 | 1.4E-02 | 10 ± 3.5 | 1.7 | 3.5 | 5.3 |
| Solid | 3062 | 2715 | QSWDLSVHQV | 3.5E+0.6 | 1.1E-02 | 3.4 ± 0.8 | 4.0 | 4.2 | 15.8 |

Key:
MOR02715 VL (SEQ ID NO:35)
MOR03064 VL (SEQ ID NO:59)
MOR03062 VL (SEQ ID NO:61)

The specificity for ED-B (determined by ELISA, immunohistochemistry and cell adhesion test) of all derivatives from the first maturation round were unchanged.

The Fab molecules shown in Tables 2a and 2b were selected for a subsequent H-CDR2 maturation in two pools. In pool 1, five Fab molecules were subjected to a similar activity, but with different L-CDR3 regions of a diversification in H-CDR2 (library size of 7×10$^7$ elements). For pool 2 (library size of 8.5×10$^7$ elements), two Fab molecules were selected. The libraries were selected separately as described above. Binding molecules with increased affinity were concentrated by two panning rounds in solution under stringent conditions.

Three Fab molecules were selected from pool 1. For derivatives MOR03243 and MOR03245, affinities of about 0.7 nmol were found. For derivative MOR03246, an affinity of 0.6 nmol was found.

The H-CDR2 sequences of the corresponding clones and the affinity data are shown in Table 3a.

TABLE 3a

| MOR0 | Parental Clone | Sequenz HCDR2 | kon [1/Ms] | koff [1/s] | KD [nM] |
|---|---|---|---|---|---|
| MOR03243 | 3055 | EIHRGGYTQYNPSLKS | 2.9E+06 | 1.8E-03 | 0.7 ± 0.2 |
| MOR03245 | 3069 | VIHKWGFTNYNPSLKS | 3.5E+06 | 1.6E-03 | 0.7 ± 0.3 |
| MOR03246 | 3075 | YIHKYGWTKYNPSLKS | 4.8E+06 | 3.0E-03 | 0.6 ± 0.1 |

Key:
Sequenz = Sequence
MOR03243 VH (SEQ ID NO:63)
MOR03243 VH (SEQ ID NO:67)
MOR03246 VH (SEQ ID NO:71)

Derivatives with improved properties could also be selected from pool 2. In comparison to the parent clones, the affinities of the derivatives were improved by a factor of 26 up to 250×. The affinities of the clones MOR03255 and MOR03258 were determined with 30 pM or 40 pM.

In Table 3b, H-CDR2-amino acid sequences of the selected clones from pool 2 as well as the corresponding affinity data are shown.

TABLE 3b

| MORO | Parental Clone | Sequenz HCDR2 | kon [1/Ms] | koff [1/s] | KD ]nM] | STDEV |
|---|---|---|---|---|---|---|
| MOR03251 | 3062 | VISNMSYTIYYADSVKG | 3.3E+06 | 2.0E-04 | 0.07 | 0,04 |
| MOR03252 | 3062 | VISNYSWHIYYADSVKG | 3.1E+06 | 6.1E-05 | 0.03 | 0.03 |
| MOR03253 | 3062 Mut | VISNMGFEIYYADSVKG | 1.6E+06 | 2.0E-04 | 0.13 | 0.05 |
| MOR03255 | 3062 | VISNRSSYIYYADSVKG | 4.9E+06 | 8.6E-05 | 0.03 | 0.03 |
| MOR03257 | 3062 | VISNRGNYIYYADSVKG | 5.3E+06 | 3.0E-04 | 0.08 | 0.06 |
| MOR03258 | 3064 | VISNQSNYIYYADSVKG | 2.7E+06 | 8.8E-05 | 0.04 | 0.02 |

Key:
Sequenz = Sequence
MOR03251 VH (SEQ ID NO:75)
MOR03252 VH (SEQ ID NO:79)
MOR03253 VH (SEQ ID NO:81)
MOR03255 VH (SEQ ID NO:83)
MOR03257 VH (SEQ ID NO:85)
MOR03258 VH (SEQ ID NO:87)

2.4 Characterization of Highly Affine Function-Blocking ED-B-Antibodies

Figure 6:
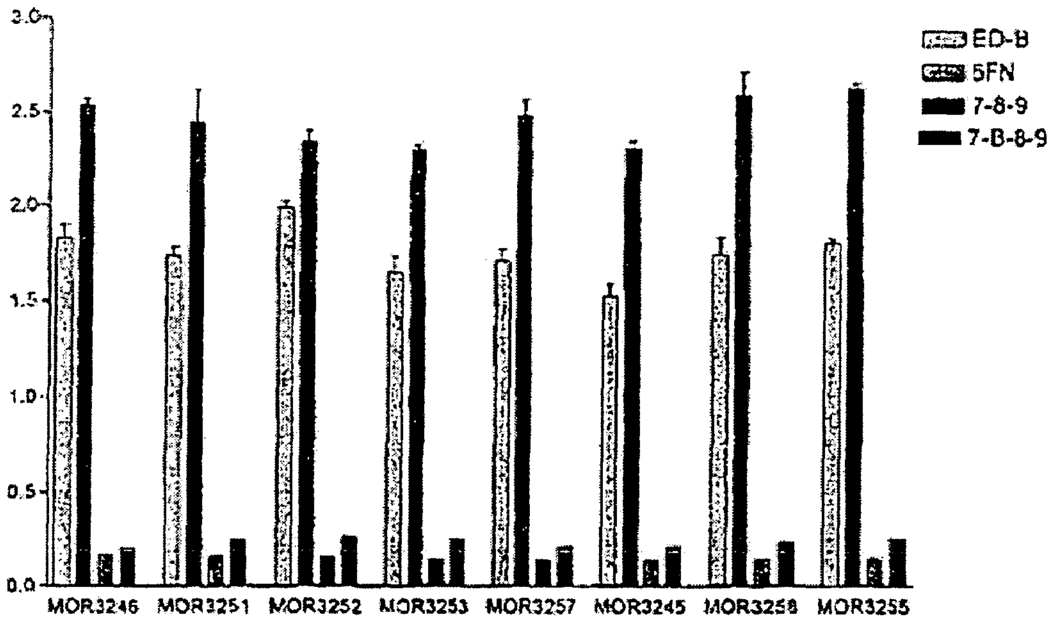
Figure 7:
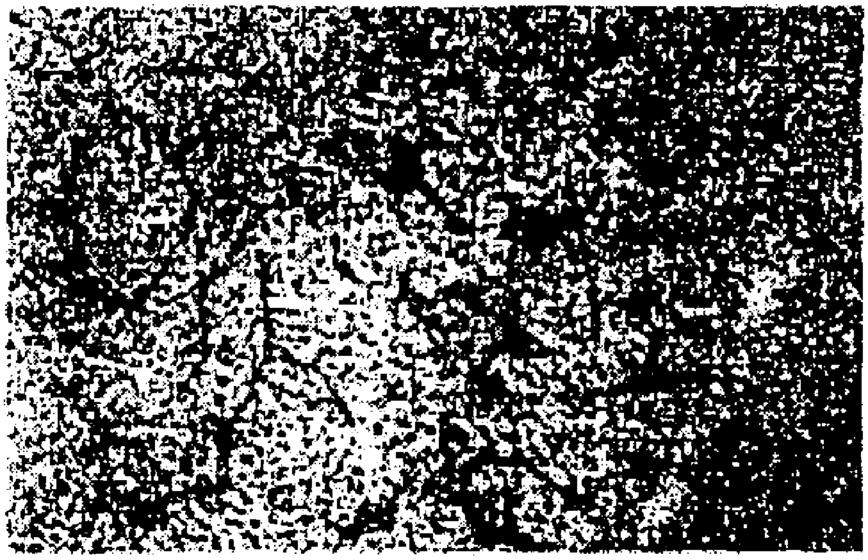
Figure 7:
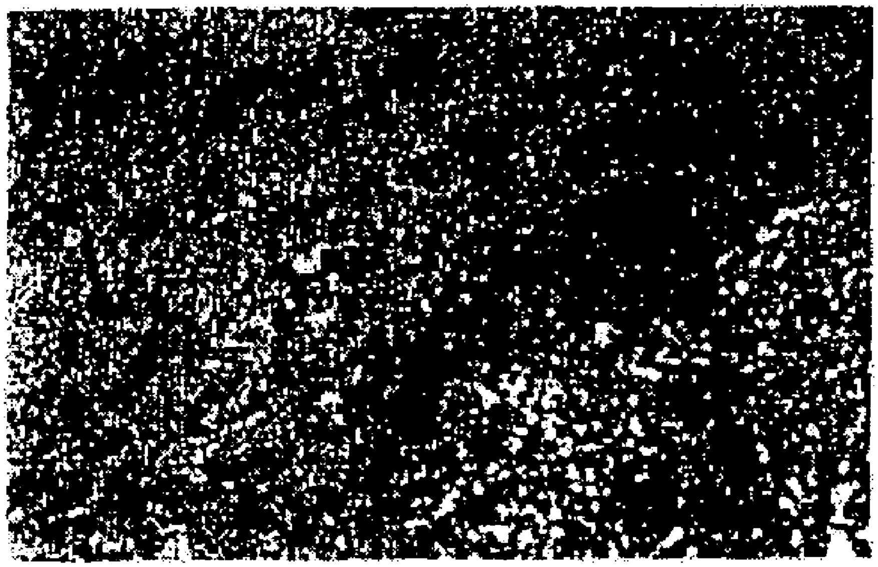
Figure 8:
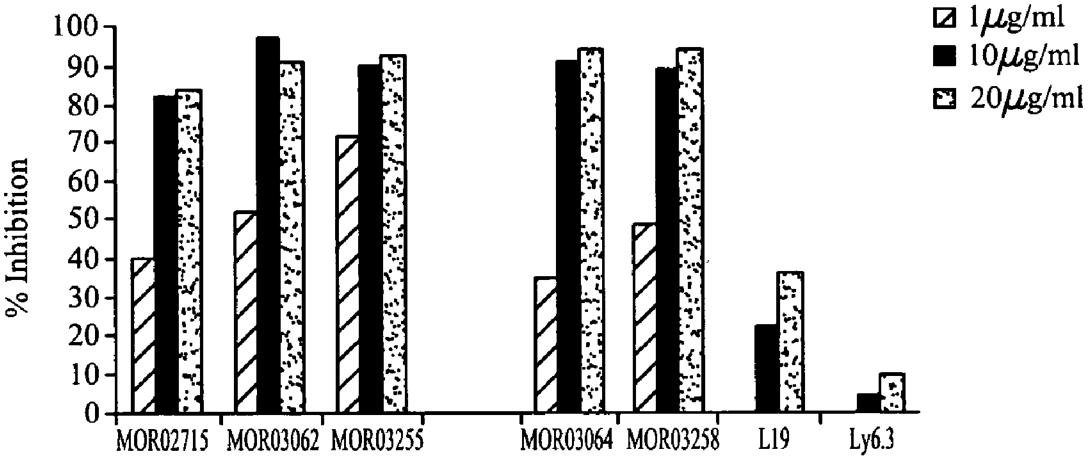

To test whether the antibodies that are obtained by affinity maturation are still always specific for ED-B, specificity tests in the ELISA format (FIG. 6), immunohistochemical studies (FIG. 7) and adhesion tests (FIG. 8) were performed. In all three tests, it was found that the specificity of the affinity-matured Fab molecules for ED-B remained unchanged. In addition, it is evident from FIG. 8 that both the parent clones, such as MOR 02715, and the clones that are produced by affinity maturation, such as MOR 03062, MOR 03255, MOR 03064 and MOR 03259, have a significantly higher biological activity (adhesion inhibition) than the known antibody L19.

Figure 9:
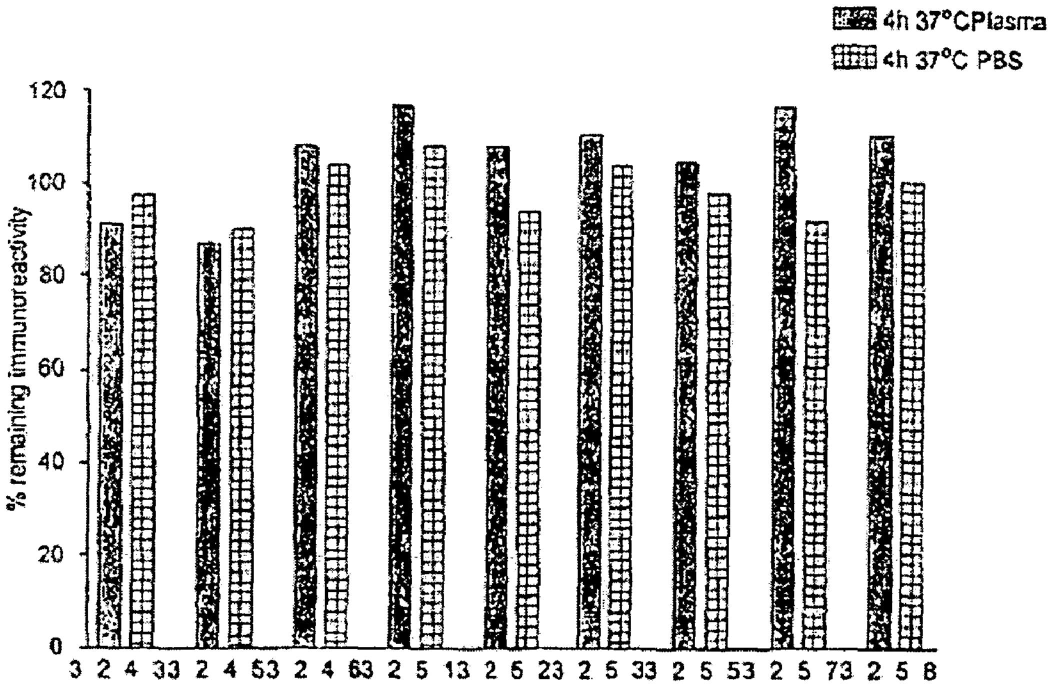

In addition, the thermal stability of the Fab molecules in human plasma was tested. To this end, the Fab molecules were incubated with human plasma for 4 hours at 37° C. without a significant loss in immune reactivity determined by ELISA (FIG. 9) being found.

All selected Fab molecules are able to block the interaction of a receptor with human microvascular endothelial cells on ED-B in a dose-dependent way, a property that known ED-B-antibody L19 does not have. Since the adhesion of HDMVEc to the extracellular matrix is one of the early steps in neoangiogenesis, the blocking of this process by the binding molecules according to the invention produces a therapeutic agent for inhibiting the formation of new vessels and for inhibiting tumor growth.

2.5 In Vivo Action

Figure 10:
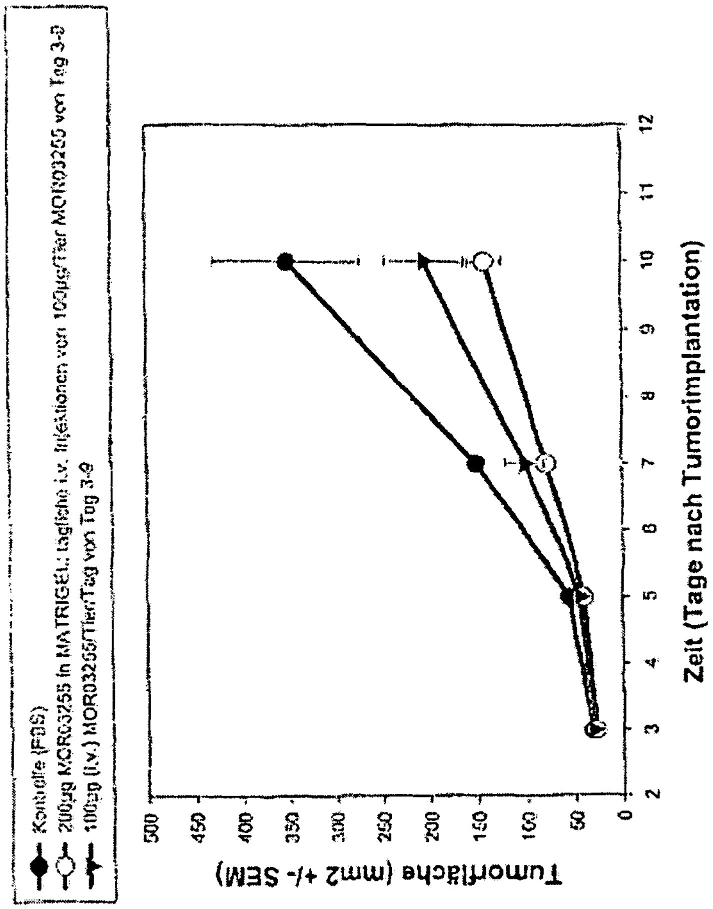
FIG. 10 shows the therapeutic effectiveness of anti-ED-B-function-blocking Fab-antibody fragments in the example of MOR 03255.

F9-Teratocarcinoma cells ($10^6$/mouse in Matrigel with/without 100 μg of Fab MOR 03255) were implanted s.c. in the flanks of hairless mice. After 3 days, the animals were treated for 7 successive days with, in each case, 100 μg of MOR03255/mouse. In comparison to the solvent control, both treatment groups show an inhibition in tumor growth in the range of 42-64%. A summary of test results is shown in FIG. 10.

Without further elaboration, it is believed that one skilled in the art can, using the preceding description, utilize the present invention to its fullest extent. The preceding preferred specific embodiments are, therefore, to be construed as merely illustrative, and not limitative of the remainder of the disclosure in any way whatsoever.

In the foregoing and in the examples, all temperatures are set forth uncorrected in degrees Celsius and, all parts and percentages are by weight, unless otherwise indicated.

The entire disclosures of all applications, patents and publications, cited herein and of corresponding German application No. 102004050101.7, filed Oct. 14, 2005 and U.S. Provisional Application Ser. No. 60/697,565, filed Jul. 11, 2005, are incorporated by reference herein.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

LITERATURE (1) Brown, L. F.; Guidi, A. J.; Schnitt, S. J.; Van De Water, L.; Iruela-Arispe, M. L.; Yeo, T.-K.; Tognazzi, K.; Dvorak, H. F. (1999) Clin. Cancer Res. 5: 1041-1056
(2) Folkman, J. (1995) Nature (Med.) 1: 27-31
(3) Risau, W. and Lemmon, V. (1988) Develop. Biol. 125: 441-450
(4) Van Den Hoff, A. (1988) Adv. Cancer Res. 50: 159-196
(5) Folkman, J. and Shing, Y. (1992) J. Biol. Chem. 267: 10931-10934
(6) George, E. L.; Baldwin, H. S.; Hynes, R. O. (1997) Blood 90: 3073-3081
(7) Bowersox, J. C. and Sorgente, N. (1982) Cancer Res. 42: 2547-2551
(8) Madri, J. A.; Pratt, B. M.; Tucker, A. M. (1988) J. Cell Biol. 106: 1375-1384
(9) Nicosia, R. F.; Bonnano, E.; Smith, M. (1993) J. Cell. Physiol. 154: 654-661
(10) Kornblihtt, A. R.; Vibe-Pedersen, K.; and Baralle, F. E., 1983. Isolation and Characterization of cDNA Clones for Human and Bovine Fibronectins. Proc. Natl. Acad. Sci. USA, 80, 3218-22
(11) Leahy, D. J.; Hendrickson, W. A.; Aukhil, I. and Erickson, H. P., 1992. Structure of Fibronectin Type III Domain from Tenascin Phased by MAS Analysis of the Selenomethionyl Protein. Science, 258, 987-91

(12) Hynes, R. O., 1987, Cell 48, 549-550
(13) Plow, E. F. et al. 2000, J. Biol. Chem., 275, 21785-21788
(14) Castellani, P.; Viale, G.; Dorcaratto, A.; Nicolo, G.; Kaczmarek, J.; Querze, G.; Zardi, L. (1994) Int. J. Cancer 59: 612-618
(15) Hashimoto-Uoshima, M.; Yan, Y. Z.; Schneider, G.; Aukhil, I. (1997) J. Cell Science 110: 227-2280
(16) Chen, W. and Culp, L. A. (1996) Exp. Cell Res. 223: 9-19
(17) Chen, W. and Culp, L. A. (1998) Clin. Exp. Metastasis 16: 30-42

We claim:

1. An antibody or an antigen-binding fragment thereof which comprises (a) a VH region which is encoded by the nucleic acid sequence SEQ ID NO: 63, SEQ ID NO: 67, SEQ ID NO: 75, SEQ ID NO: 79, SEQ ID NO: 81, SEQ ID NO: 83, SEQ ID NO: 85, SEQ ID NO: 87 or the H-CDR1-, H-CDR2- and H-CDR3 regions of one of these VH regions, and (b) a VL region which is encoded by the nucleic acid sequence SEQ ID NO: 65, SEQ ID NO: 69, SEQ ID NO: 77, SEQ ID NO: 59 or the L-CDR1-, L-CDR2- and L-CDR3-regions of one of these VL regions, wherein said antibody or antibody fragment specifically binds to the ED-B domain of fibronectin.

2. The antibody fragment according to claim 1, which binds to said EDB domain of fibronectin.

3. An antibody or antigen-binding fragment thereof according to claim 1, comprising the H-CDR1, H-CDR2, and H-CDR3 regions coded by SEQ ID NO: 63 and the L-CDR1, L-CDR2 and L-CDR3 regions coded by SEQ ID NO: 65.

4. An antibody or antigen-binding fragment thereof according to claim 1, comprising the H-CDR1, H-CDR2, and H-CDR3 regions coded by SEQ ID NO: 67 and the L-CDR1, L-CDR2 and L-CDR3 regions coded by SEQ ID NO: 69 .

5. An antibody or antigen-binding fragment thereof according to claim 1, comprising the H-CDR1, H-CDR2, and H-CDR3 regions coded by SEQ ID NO: 75 and the L-CDR1, L-CDR2 and L-CDR3 regions coded by SEQ ID NO: 77.

6. An antibody or antigen-binding fragment thereof according to claim 1, comprising the H-CDR1, H-CDR2, and H-CDR3 regions coded by SEQ ID NO: 79 and the L-CDR1, L-CDR2 and L-CDR3 regions coded by SEQ ID NO: 77.

7. An antibody or antigen-binding fragment thereof according to claim 1, comprising the H-CDR1, H-CDR2, and H-CDR3 regions coded by SEQ ID NO: 81 and the L-CDR1, L-CDR2 and L-CDR3 regions coded by SEQ ID NO: 77.

8. An antibody or antigen-binding fragment thereof according to claim 1, comprising the H-CDR1, H-CDR2, and H-CDR3 regions coded by SEQ ID NO: 83 and the L-CDR1, L-CDR2 and L-CDR3 regions coded by SEQ ID NO: 77.

9. An antibody or antigen-binding fragment thereof according to claim 1, comprising the H-CDR1, H-CDR2, and H-CDR3 regions coded by SEQ ID NO: 85 and the L-CDR1, L-CDR2 and L-CDR3 regions coded by SEQ ID NO: 77.

10. An antibody or antigen-binding fragment thereof according to claim 1, comprising the H-CDR1, H-CDR2, and H-CDR3 regions coded by SEQ ID NO:87 and the L-CDR1, L-CDR2 and L-CDR3 regions coded by SEQ ID NO: 59.

11. An antibody or antigen-binding fragment thereof according to claim 3, comprising the VH region that is coded by SEQ ID NO:63 and the VL region that is coded by SEQ ID NO:65.

12. An antibody or antigen-binding fragment thereof according to claim 4, comprising the VH region that is coded by SEQ ID NO:67 and the VL region that is coded by SEQ ID NO:69.

13. An antibody or antigen-binding fragment thereof according to claim 5, comprising the VH region that is coded by SEQ ID NO:75 and the VL region that is coded by SEQ ID NO:77.

14. An antibody or antigen-binding fragment thereof according to claim 6, comprising the VH region that is coded by SEQ ID NO:79 and the VL region that is coded by SEQ ID NO:77.

15. An antibody or antigen-binding fragment thereof according to claim 7, comprising the VH region that is coded by SEQ ID NO:81 and the VL region that is coded by SEQ ID NO:77.

16. An antibody or antigen-binding fragment thereof according to claim 8, comprising the VH region that is coded by SEQ ID NO:83 and the VL region that is coded by SEQ ID NO:77.

17. An antibody or antigen-binding fragment thereof according to claim 9, comprising the VH region is coded by SEQ ID NO: 85 and the VL region is coded by SEQ ID NO: 77 .

18. An antibody or antigen-binding fragment thereof according to claim 10, comprising the VH region that is coded by SEQ ID NO:87 and the VL region that is coded by SEQ ID NO: 59.

19. A conjugate which comprises a therapeutic active ingredient and the antibody of claim 1.

20. The conjugate according to claim 19, wherein the therapeutic active ingredient is a radio-therapeutic or a chemotherapeutic agent.

21. A fusion protein which comprises the antibody of claim 1.

22. The fusion protein according to claim 21 which comprises a cytokine or a bispecific antibody.

23. A conjugate which comprises a diagnostically detectable labeling group and the antibody of claim 1.

24. The conjugate according to claim 23, wherein the diagnostically detectable labeling group is a radio-labeling group, an NMR-labeling group, a dye, an enzyme or a fluorescence labeling group.

25. A pharmaceutical composition, comprising as active ingredient the antibody according to claim 1 and a pharmacologically acceptable vehicle, adjuvant or diluent.

26. A diagnostic composition, comprising as diagnostic reagent, the antibody according to claim 1.

* * * * *